US011274152B2

(12) United States Patent
Korman et al.

(10) Patent No.: US 11,274,152 B2
(45) Date of Patent: *Mar. 15, 2022

(54) COMBINATION OF ANTI-LAG-3 ANTIBODIES AND ANTI-PD-1 ANTIBODIES TO TREAT TUMORS

(71) Applicant: Bristol-Myers Squibb Company, Princeton, NJ (US)

(72) Inventors: Alan J. Korman, Piedmont, CA (US); Nils Lonberg, Woodside, CA (US); David J. Fontana, Clyde Hill, WA (US); Andres A. Gutierrez, Lawrenceville, NJ (US); Mark J. Selby, San Francisco, CA (US); Katherine Lewis, Lake Forest Park, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/018,241

(22) Filed: Sep. 11, 2020

(65) Prior Publication Data

US 2021/0009692 A1 Jan. 14, 2021

Related U.S. Application Data

(63) Continuation of application No. 16/376,394, filed on Apr. 5, 2019, which is a continuation of application No. 16/108,973, filed on Aug. 22, 2018, now abandoned, which is a continuation of application No. 15/021,102, filed as application No. PCT/US2014/056277 on Sep. 18, 2014, now Pat. No. 10,081,681.

(60) Provisional application No. 62/014,471, filed on Jun. 19, 2014, provisional application No. 61/880,606, filed on Sep. 20, 2013.

(51) Int. Cl.
| | |
|---|---|
| *C07K 16/00* | (2006.01) |
| *C07K 16/28* | (2006.01) |
| *A61P 35/00* | (2006.01) |
| *A61K 39/00* | (2006.01) |

(52) U.S. Cl.
CPC .......... *C07K 16/2818* (2013.01); *A61P 35/00* (2018.01); *C07K 16/2803* (2013.01); *A61K 2039/505* (2013.01); *A61K 2039/507* (2013.01); *A61K 2039/54* (2013.01); *A61K 2039/545* (2013.01); *C07K 2317/21* (2013.01); *C07K 2317/24* (2013.01); *C07K 2317/53* (2013.01); *C07K 2317/56* (2013.01); *C07K 2317/565* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,545,806 A | 8/1996 | Lonberg et al. |
| 5,773,578 A | 6/1998 | Hercend et al. |
| 5,811,097 A | 9/1998 | Allison et al. |
| 5,874,250 A | 2/1999 | Hercend et al. |
| 5,976,877 A | 11/1999 | Hercend et al. |
| 6,143,273 A | 11/2000 | Faure et al. |
| 6,197,524 B1 | 3/2001 | Romagnani |
| 6,207,156 B1 | 3/2001 | Kuchroo et al. |
| 6,482,925 B1 | 11/2002 | El Tayar et al. |
| 6,500,422 B2 | 12/2002 | Biffoni |
| RE38,313 E | 11/2003 | Faure et al. |
| 6,808,710 B1 | 10/2004 | Wood et al. |
| 7,138,501 B2 | 11/2006 | Ruben et al. |
| 7,306,906 B2 | 12/2007 | Maruyama et al. |
| 7,329,737 B2 | 2/2008 | Sexton et al. |
| 7,563,441 B2 | 7/2009 | Graus et al. |
| 7,595,048 B2 | 9/2009 | Honjo et al. |
| 7,605,238 B2 | 10/2009 | Korman et al. |
| 7,635,757 B2 | 12/2009 | Freeman et al. |
| 7,790,160 B2 | 9/2010 | Von Strandmann et al. |
| 7,850,965 B2 | 12/2010 | Jensen et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,217,149 B2 | 7/2012 | Irving et al. |
| 8,383,796 B2 | 2/2013 | Korman et al. |
| 8,409,577 B2 | 4/2013 | Thompson et al. |
| 8,476,419 B2 | 7/2013 | Thielemans |
| 8,551,481 B2 | 10/2013 | Pardoll et al. |
| 8,728,474 B2 | 5/2014 | Honjo et al. |
| 8,779,105 B2 | 7/2014 | Korman et al. |

(Continued)

FOREIGN PATENT DOCUMENTS

| | | |
|---|---|---|
| CN | 101490085 A1 | 7/2009 |
| WO | WO-9110682 A1 | 7/1991 |

(Continued)

OTHER PUBLICATIONS

Woo et al. (Cancer Res; 72(4); 917-27, Published online Dec. 2011) (Year: 2011).*

(Continued)

*Primary Examiner* — Meera Natarajan
(74) *Attorney, Agent, or Firm* — Sterne, Kessler, Goldstein & Fox P.L.L.C.

(57) ABSTRACT

Provided are methods for clinical treatment of tumors (e.g., advanced solid tumors) using an anti-LAG-3 antibody in combination with an anti-PD-1 antibody.

12 Claims, 4 Drawing Sheets

Specification includes a Sequence Listing.

(56) References Cited

U.S. PATENT DOCUMENTS

| | | |
|---|---|---|
| 9,005,629 B2 | 4/2015 | Pardoll et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,212,224 B2 | 12/2015 | Cogswell et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,580,505 B2 | 2/2017 | Korman et al. |
| 9,580,507 B2 | 2/2017 | Korman et al. |
| 9,856,320 B2 | 1/2018 | Cogswell |
| 10,072,082 B2 | 9/2018 | Cogswell |
| 10,081,681 B2 | 9/2018 | Korman et al. |
| 10,138,299 B2 | 11/2018 | Cogswell |
| 10,266,591 B2 | 4/2019 | Lonberg et al. |
| 10,266,594 B1 | 4/2019 | Cogswell |
| 10,266,595 B2 | 4/2019 | Cogswell |
| 10,266,596 B1 | 4/2019 | Cogswell |
| 10,308,714 B2 | 6/2019 | Cogswell |
| 10,316,090 B2 | 6/2019 | Cogswell |
| 10,316,091 B2 | 6/2019 | Cogswell |
| 10,323,092 B2 | 6/2019 | Cogswell |
| 10,323,093 B2 | 6/2019 | Cogswell |
| 10,344,089 B2 | 7/2019 | Thudium et al. |
| 10,358,495 B2 | 7/2019 | Ullman et al. |
| 10,377,824 B2 | 8/2019 | Lonberg et al. |
| 10,441,655 B2 | 10/2019 | Korman et al. |
| 10,577,423 B2 | 3/2020 | Cogswell et al. |
| 10,584,170 B2 | 3/2020 | Cogswell et al. |
| 10,604,575 B2 | 3/2020 | Cogswell et al. |
| 2002/0086014 A1 | 7/2002 | Korman et al. |
| 2002/0146753 A1 | 10/2002 | Ditzel et al. |
| 2003/0059937 A1 | 3/2003 | Ruben et al. |
| 2003/0129601 A1 | 7/2003 | Cole |
| 2004/0072164 A1 | 4/2004 | Maruyama et al. |
| 2004/0171551 A1 | 9/2004 | Triebel |
| 2005/0009136 A1 | 1/2005 | Nixon et al. |
| 2005/0226876 A1 | 10/2005 | Graus et al. |
| 2006/0083744 A1 | 4/2006 | Chen et al. |
| 2006/0110383 A1 | 5/2006 | Honjo et al. |
| 2006/0177442 A1 | 8/2006 | Von Strandmann et al. |
| 2006/0240024 A1 | 10/2006 | Pardoll et al. |
| 2007/0004910 A1 | 1/2007 | Sexton et al. |
| 2007/0160598 A1 | 7/2007 | Dennis et al. |
| 2008/0038264 A1 | 2/2008 | Bodary et al. |
| 2008/0069822 A1 | 3/2008 | Jensen et al. |
| 2008/0260641 A1 | 10/2008 | Teeling et al. |
| 2008/0279865 A1 | 11/2008 | Gomez-Navarro |
| 2009/0055944 A1 | 2/2009 | Korman et al. |
| 2009/0203538 A1 | 8/2009 | Sugioka et al. |
| 2009/0217401 A1 | 8/2009 | Korman et al. |
| 2009/0252741 A1 | 10/2009 | Liu |
| 2009/0297518 A1 | 12/2009 | Honjo et al. |
| 2009/0317368 A1 | 12/2009 | Chen |
| 2010/0055102 A1 | 3/2010 | Langermann et al. |
| 2010/0196394 A1 | 8/2010 | Pardoll et al. |
| 2010/0233183 A1 | 9/2010 | Triebel et al. |
| 2011/0007023 A1 | 1/2011 | Abrahamsson et al. |
| 2011/0081341 A1 | 4/2011 | Honjo et al. |
| 2011/0150892 A1 | 6/2011 | Thudium et al. |
| 2011/0209230 A1 | 8/2011 | Korman et al. |
| 2013/0122014 A1 | 5/2013 | Korman et al. |
| 2013/0133091 A1 | 5/2013 | Korman et al. |
| 2013/0309250 A1 | 11/2013 | Cogswell et al. |
| 2014/0093511 A1 | 4/2014 | Lonberg et al. |
| 2014/0212422 A1 | 7/2014 | Korman et al. |
| 2014/0271684 A1 | 9/2014 | Li |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0348743 A1 | 11/2014 | Korman et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2015/0307609 A1 | 10/2015 | Lonberg et al. |
| 2015/0337038 A1 | 11/2015 | Korman et al. |
| 2016/0075782 A1 | 3/2016 | Korman et al. |
| 2016/0090417 A1 | 3/2016 | Cogswell et al. |
| 2016/0108121 A1 | 4/2016 | Pardoll et al. |
| 2016/0158355 A1 | 6/2016 | Honjo et al. |
| 2016/0158356 A1 | 6/2016 | Honjo et al. |
| 2016/0222116 A1 | 8/2016 | Korman et al. |
| 2016/0326248 A1 | 11/2016 | Gutierrez et al. |
| 2016/0362495 A1 | 12/2016 | Korman et al. |
| 2017/0051060 A1 | 2/2017 | Honjo et al. |
| 2017/0088615 A1 | 3/2017 | Korman et al. |
| 2017/0137514 A1 | 5/2017 | Lonberg et al. |
| 2017/0143827 A1 | 5/2017 | Vikram et al. |
| 2017/0158767 A1 | 6/2017 | Korman et al. |
| 2018/0066054 A1 | 3/2018 | Thudium et al. |
| 2018/0282414 A1 | 6/2018 | Cogswell |
| 2018/0273624 A1 | 9/2018 | Cogswell |
| 2018/0282413 A1 | 10/2018 | Cogswell |
| 2018/0312590 A1 | 11/2018 | Cogswell |
| 2018/0319887 A1 | 11/2018 | Cogswell |
| 2018/0371087 A1 | 12/2018 | Lonberg et al. |
| 2019/0092863 A1 | 3/2019 | Cogswell |
| 2019/0100589 A1 | 4/2019 | Cogswell |
| 2019/0100590 A1 | 4/2019 | Cogswell |
| 2019/0112376 A1 | 4/2019 | Cogswell |
| 2019/0112377 A1 | 4/2019 | Cogswell |
| 2019/0135920 A1 | 5/2019 | Cogswell |
| 2019/0153099 A1 | 5/2019 | Cogswell |
| 2019/0256594 A1 | 8/2019 | Lonberg et al. |
| 2019/0276538 A1 | 9/2019 | Thudium et al. |
| 2019/0276539 A1 | 9/2019 | Thudium et al. |
| 2020/0062845 A1 | 2/2020 | Korman et al. |
| 2020/0062846 A1 | 2/2020 | Honjo et al. |
| 2020/0062848 A1 | 2/2020 | Korman et al. |
| 2020/0138945 A1 | 5/2020 | Korman et al. |
| 2020/0231671 A1 | 7/2020 | Thudium et al. |
| 2020/0308282 A1 | 10/2020 | Cogswell et al. |
| 2020/0385466 A1 | 12/2020 | Thudium et al. |
| 2020/0385467 A1 | 12/2020 | Thudium et al. |
| 2021/0238287 A1 | 8/2021 | Srivastava et al. |
| 2021/0261666 A1 | 8/2021 | Novotny, Jr. et al. |
| 2021/0283251 A1 | 9/2021 | Burton et al. |
| 2021/0338813 A1 | 11/2021 | Maurer et al. |
| 2021/0340250 A1 | 11/2021 | Korman et al. |

FOREIGN PATENT DOCUMENTS

| | | |
|---|---|---|
| WO | WO-9530750 A2 | 11/1995 |
| WO | WO-9703695 A1 | 2/1997 |
| WO | WO-9713852 A1 | 4/1997 |
| WO | WO-9732733 A1 | 9/1997 |
| WO | WO-9842752 A1 | 10/1998 |
| WO | WO-9858059 A1 | 12/1998 |
| WO | WO-0037504 A2 | 6/2000 |
| WO | WO-0069914 A2 | 11/2000 |
| WO | WO-0114424 A2 | 3/2001 |
| WO | WO-200243478 A2 | 6/2002 |
| WO | WO-03088808 A2 | 10/2003 |
| WO | WO-03099196 A2 | 12/2003 |
| WO | WO-2004004771 A1 | 1/2004 |
| WO | WO-2004039956 A2 | 5/2004 |
| WO | WO-2004078928 A1 | 9/2004 |
| WO | WO-2005034733 A2 | 4/2005 |
| WO | WO-2005059106 A2 | 6/2005 |
| WO | WO-2005067620 A2 | 7/2005 |
| WO | WO-2006007850 A1 | 1/2006 |
| WO | WO-2006121168 A1 | 11/2006 |
| WO | WO-2007005874 A2 | 1/2007 |
| WO | WO-2008007648 A1 | 1/2008 |
| WO | WO-2008073160 A2 | 6/2008 |
| WO | WO-2008121615 A2 | 10/2008 |

(56) References Cited

FOREIGN PATENT DOCUMENTS

| | | |
|---|---|---|
| WO | WO-2008121616 A2 | 10/2008 |
| WO | WO-2008132601 A1 | 11/2008 |
| WO | WO-2008156712 A1 | 12/2008 |
| WO | WO-2009014708 A2 | 1/2009 |
| WO | WO-2009114335 A2 | 9/2009 |
| WO | WO-2010019570 A2 | 2/2010 |
| WO | WO-2011008092 A2 | 1/2011 |
| WO | WO-2011066389 A1 | 6/2011 |
| WO | WO-2011161699 A2 | 12/2011 |
| WO | WO-2012009442 A2 | 1/2012 |
| WO | WO-2012054438 A1 | 4/2012 |
| WO | WO-2012059858 A1 | 5/2012 |
| WO | WO-2012145493 A1 | 10/2012 |
| WO | WO-2013063186 A2 | 5/2013 |
| WO | WO-2013173223 A1 | 11/2013 |
| WO | WO-2016168716 A1 | 11/2013 |
| WO | WO2014/008218 * | 1/2014 |
| WO | WO-2014140180 A1 | 9/2014 |
| WO | WO-2015016718 A1 | 2/2015 |
| WO | WO-2015042246 A1 | 3/2015 |
| WO | WO-2015116539 A1 | 8/2015 |

OTHER PUBLICATIONS

Turnis et al. (OncoImmunology 1:7, 1172-1174; Oct. 2012). (Year: 2012).*

Anonymous: "History of Changes for Study: NCT00730639, A Phase 1b Study of MDX-1106 in Subjects With Advanced or Recurrent Malignancies (MDX1106-03)," ClinicalTrials.gov Archive, accessed at https://clinicaltrials.gov/ct2/history/NCT00730639?V_8=View, accessed on Feb. 5, 2021, 10 pages.

Agata, Y., et al., "Expression of the PD-1 Antigen on the Surface of Stimulated Mouse T and B lymphocytes," International Immunology 8(5):765-772, Oxford University Press, England (May 1996).

Agrawal, S., et al., "Clinical Pharmacokinetics (PK) of BMS-936558, a Fully Human Anti-pd-1 Monoclonal Antibody," Journal of Clinical Oncology 30(15):1 (2012), ASCO Annual Meeting Website, [retrieved on Jan. 13, 2015]. Retrieved from the Internet : URL:http://www.meetinglibrary.asco.org/content/98623-114.

Baixeras, E., et al., "Characterization of the Lymphocyte Activation Gene 3-encoded Protein. A New Ligand for Human Leukocyte Antigen Class II Antigens," The Journal of Experimental Medicine 176(2):327-337, Rockefeller University Press, United States (Aug. 1992).

Bennett, F., et al., "Program Death-1 Engagement Upon TCR Activation has Distinct Effects on Costimulation and Cytokine-driven Proliferation: Attenuation of ICOS, IL-4, and IL-21, but not CD28, IL-7, and IL-15 responses," The Journal of Immunology 170(2):711-718, The American Association of Immunologists, United States (Jan. 2003).

Bettini, M., et al., "Cutting Edge: Accelerated Autoimmune Diabetes in the Absence of LAG-3," Journal of Immunology 187(7):3493-3498, American Association of Immunologists, United States (Oct. 2011 ).

Blackburn, S.D., et al., "Coregulation of CD8+ T cell exhaustion by multiple inhibitory receptors during chronic viral infection," Nature immunology 10(1):29-37, Nature America Inc., United States (Jan. 2009).

Blank, C., et al., "Interaction of PD-L1 on Tumor Cells with PD-1 on Tumor-specific T Cells as a Mechanism of Immune Evasion: Implications for Tumor Immunotherapy," Cancer Immunology Immunotherapy 54(4):307-314, Springer-Verlag, Germany (Apr. 2005).

Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).

Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).

Brown, J.A., et al., "Blockade of Programmed Death-1 Ligands on Dendritic Cells Enhances T Cell Activation and Cytokine Production," The Journal of Immunology 170(3):1257-1266, The American Association of Immunologists, United States (Feb. 2003).

Camisaschi, C., et al., "LAG-3 Expression Defines a Subset of CD4(+)CD25(High)Foxp3(+) Regulatory T Cells That Are Expanded at Tumor Sites," Journal of Immunology 184(11):6545-6551, American Association of Immunologists, United states (Jun. 2010).

Carter, L.L., et al., "PD-1:PD-L Inhibitory Pathway Affects both CD4(+) and CD8(+) T Cells and is Overcome by IL-2," European Journal of Immunology 32(3):634-643, WILEY-VCH Verlag GmbH, German (Mar. 2002).

Casati, C., et al., "Soluble Human LAG-3 Molecule Amplifies the in Vitro Generation of Type 1 Tumor-specific Immunity," Cancer Research 66(8):4450-4460, American Association for Cancer Research, United States (Apr. 2006).

Chelius, D., et al., "Identification and Characterization of Deamidation Sites in the Conserved Regions of Human Immunoglobulin Gamma Antibodies," Analytical Chemistry 77(18):6004-6011, American Chemical Society, United States (2005).

Cleland, J,L., et al., "The Development of Stable Protein Formulations: A Close Look at Protein Aggregation, Deamidation, and Oxidation," Critical Reviews in Therapeutic Drug Carrier Systems 10(4):307-377, CRC Press, United States (1993).

Clinicaltrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.

ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_06_20, last accessed on Jan. 13, 2015, 4 pages.

Correia, I,R., et al., "Stability of IgG Isotypes in Serum," mAbs 2(3):221-232, Taylor & Francis, United States (May-Jun. 2010).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

Dong, H. and Chen, L., "B7-H1 Pathway and its Role in the Evasion of Tumor Immunity," Journal of Molecular Medicine 81(5):281-287, Springer, Germany (May 2003).

Dong, H., et al., "B7-H1, a Third Member of the B7 Family, Co-stimulates T-cell Proliferation and Interleukin-10 Secretion," Nature Medicine 5(12):1365-1369, Nature America, United States (Dec. 1999).

Dong, H., et al., "Tumor-associated B7-H1 Promotes T-cell Apoptosis: A Potential Mechanism of Immune Evasion," Nature Medicine 8(8):793-800, Nature Publishing Company, United States (Aug. 2002).

Drake, C.G., et al., "Blocking the Regulatory T Cell Molecule LAG-3 Augments in Vivo Anti-tumor Immunity in an Autochthonous Model of Prostate Cancer," Journal of Clinical Oncology 24(18):2573 (Jun. 2006).

Drake, C.G., et al., "Breathing New Life into Immunotherapy: Review of Melanoma, Lung and Kidney Cancer," Nature Reviews Clinical Oncology 11(1):24-37, Nature Pub. Group, England (Jan. 2014).

El Mir, S. and Triebel, F., "A Soluble Lymphocyte Activation Gene-3 Molecule Used as a Vaccine Adjuvant Elicits Greater Humoral and Cellular Immune Responses to Both Particulate and Soluble Antigens," Journal of Immunology 164(11):5583-5589, American Association of Immunologists, United States (Jun. 2000).

Extended European Search Report dated Feb. 23, 2017 in EP Patent Application No. 16197459.7, European Patent Office, Munich, Germany, 15 pages.

Fishwild, D.M., et al., "High-Avidity Human IgG Kappa Monoclonal Antibodies from a Novel Strain of Minilocus Transgenic Mice," Nature Biotechnology 14(7):845-851, Nature America Publishing, United States (1996).

(56) References Cited

OTHER PUBLICATIONS

Freeman, G.J., et al., "Engagement of the PD-1 Immunoinhibitory Receptor by a Novel B7 Family Member Leads to Negative Regulation of Lymphocyte Activation," The Journal of Experimental Medicine 192(7):1027-1034, The Rockefeller University Press, United States (Oct. 2000).

Gillam, W.A., et al., "A phase I study of IMP321 and Gemcitabine as the Front-Line Therapy in Patients with Advanced Pancreatic Adenocarcinoma," Investigational New Drugs 31(3):707-713, Springer, United States (Jun. 2013).

Goding, S,R., et al., "Combination of Adoptive Cell Transfer, Anti-PD-L1 and Anti-LAG-3 Antibodies for the Treatment of Recurrent Tumors," OncoImmunology 2(8), 4 pages (May 2013).

Goding, S,R., et al., "Restoring Immune Function of Tumor-specific CD4+ T Cells During Recurrence of Melanoma," Journal of Immunology 190(9):4899-4909, American Association of Immunologists, United states (May 2013 ).

Goldberg, M.V., et al., "LAG-3 in Cancer Immunotherapy," Current Topics in Microbiology and Immunology 344:269-278, Springer Verlag, Germany (2011).

Grosso, J.F., et al., "LAG-3 Regulates CD8+ T Cell Accumulation and Effector Function in Murine Self- and Tumor-tolerance Systems," The Journal of Clinical Investigation 117(11):3383-3392, American Society for Clinical Investigation, United States (Nov. 2007).

Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).

Hansen, J.A., et al., "Monoclonal Antibodies Identifying a Novel T-cell Antigen and la Antigens of Human Lymphocytes," Immunogenetics 10:247-260, Springer-Verlag (Feb. 1980).

Harris, R.J., et al., "Identification of Multiple Sources of Charge Heterogeneity in a Recombinant Antibody," Journal of chromatography. B, Biomedical Sciences and Applications 752(2):233-245, Elsevier, Netherlands (2001).

Haycock,G,B., et al., "Geometric Method for Measuring Body Surface Area: a Height-weight Formula Validated in Infants, Children, and Adults," The Journal of Pediatrics 93(1):62-66, Mosby, United states (Jul. 1978 ).

Hemon, P., et al., "MHC Class II Engagement by its Ligand LAG-3 (CD223) Contributes to Melanoma Resistance to Apoptosis," Journal of Immunology 86(9):5173-5183, American Association of Immunologists, United States (May 2011).

Huang, C,T., et al., "Role of LAG-3 in Regulatory T Cells," Immunity 21(4):503-513, Cell Press, United States (Oct. 2004).

Huard, B., et al., "Characterization of the Major Histocompatibility Complex Class II Binding Site on LAG-3 Protein," Proceedings of the National Academy of Sciences of the United States of America 94(11):5744-5749, National Academy of Sciences, United States (May 1997).

Huard, B., et al., "Cellular expression and tissue distribution of the humanLAG-3-encoded protein, an MHC class II ligand," Immunogenetics 39:213-217, Springer-Verlag, Germany (1994).

Huard, B., et al., "Lymphocyte-activation Gene 3/major Histocompatibility Complex Class II Interaction Modulates the Antigenic Response of CD4+ T Lymphocytes," European Journal of Immunology 24(12):3216-3221, Wiley-VCH, Germany (Dec. 1994).

Huard, B., et al., "T Cell Major Histocompatibility Complex Class II Molecules Down-regulate CD4+ T Cell Clone Responses Following LAG-3 Binding," European Journal of Immunology 26(5):1180-1186, Wiley-VCH, Germany (May 1996).

Hutloff, A., et al., "ICOS is an Inducible T-cell Co-stimulator Structurally and Functionally Related to CD28," Nature 397(6716):263-266, Nature Publishing Group, England (Jan. 1999).

International Preliminary Report on Patentability for Application No. PCT/US2009/053405, dated Feb. 15, 2011, 10 pages.

International Preliminary Report on Patentability for Application Serial No. PCT/US2014/056277, dated Mar. 22, 2016, 10 pages.

International Search Report and written opinion for International Application No. PCT/US2009/053405, ISA/US Alexandria, Virginia, dated Mar. 31, 2010, 15 pages.

International Search Report and Written Opinion for International Application No. PCT/US2013/48999, European patent office, Rijswijk, dated Sep. 23, 2013, 11 pages.

International Search Report and Written Opinion for International Application No. PCT/US2014/056277, European patent office, Rijswijk, dated Feb. 4, 2015, 15 pages.

International Search Report and Written Opinion for International Application No. PCT/US2015/012916, European patent office, Rijswijk, dated Jun. 23, 2015, 12 pages.

Iouzalen, N., et al., "LAP, A Lymphocyte Activation Gene-3 (LAG-3)-associated Protein That Binds to a Repeated EP Motif in the Intracellular Region of LAG-3, May Participate in the Downregulation of the CD3/TCR Activation Pathway," European Journal of Immunology 31(10):2885-2891, Wiley-VCH, Germany (Oct. 2001).

Ishida, Y., et al., "Induced Expression of PD-1, a Novel Member of the Immunoglobulin Gene Superfamily, Upon Programmed Cell Death," The EMBO Journal 11(11):3887-3895, Oxford University Press, England (Nov. 1992).

Iwai, Y., et al., "Involvement of PD-L1 on Tumor Cells in the Escape from Host Immune System and Tumor Immunotherapy by PD-L1 Blockade," Proceedings of the National Academy of Sciences 99(19):12293-12297, The National Academy of Sciences of the United States (Sep. 2002).

Keir, M,E., et al., "PD-1 and Its Ligands in Tolerance and Immunity," Annual Review of Immunology 26:677-704, Annual Reviews Inc, United states (2008).

Kocak, E., et al., "Combination Therapy with Anti-CTL Antigen-4 and Anti-4-1BB Antibodies Enhances Cancer Immunity and Reduces Autoimmunity," Cancer Research 66(14):7276-7284, American Association for Cancer Research, United States (Jul. 2006).

Konishi, J., et al., "B7-H1 Expression on Non-small Cell Lung Cancer Cells and its Relationship with Tumor-infiltrating Lymphocytes and their PD-1 Expression," Clinical Cancer Research 10(15):5094-5100, American Association for Cancer Research, United States (Aug. 2004).

Kosky, A,A., et al., "Multivariate Analysis of the Sequence Dependence of Asparagine Deamidation Rates in Peptides," Pharmaceutical Research 26(11):2417-2428, Kluwer Academic/Plenum Publishers, United states (Nov. 2009).

Kroon, D,J., et al., "Identification of Sites of Degradation in a Therapeutic Monoclonal Antibody by Peptide Mapping," Pharmaceutical Research 9(11):1386-1393, Kluwer Academic/Plenum Publishers, United states (Nov. 1992).

Latchman, Y., et al., "PD-L2 is a Second Ligand for PD-1 and Inhibits T Cell Activation," Nature Immunology 2(3):261-268, Nature Publishing Group, United States (Mar. 2001).

Lipson, E.J., et al., "Durable Cancer Regression Off-treatment and Effective Reinduction Therapy with an Anti-PD-1 Antibody," Clinical Cancer Research 19(2):462-468, The Association, United States (Jan. 2013).

Lonberg, N., et al., "Antigen-specific Human Antibodies from Mice Comprising Four Distinct Genetic Modifications," Nature 368(6474):856-859, Nature Publishing Group, United States (Apr. 1994).

Lyford-Pike, S., et al., "Evidence for a Role of the PD-1:PD-L1 Pathway in Immune Resistance of HPV-associated Head and Neck Squamous Cell Carcinoma," Cancer Research 73(6):1733-1741, American Association for Cancer Research, United States (Mar. 2013).

Maccallum, R.M., et al., "Antibody-antigen Interactions: Contact Analysis and Binding Site Topography," Journal of Molecular Biology 262(5):732-745, Academic Press, England (Oct. 1996).

Macon-Lemaitre, L. and Triebel, F., "The Negative Regulatory Function of the Lymphocyte-activation Gene-3 Co-receptor (CD223) on Human T Cells," Immunology 115(2):170-178, Blackwell Scientific Publications, England (Jun. 2005).

Matsuzaki, J., et al., "Tumor-infiltrating NY-ESO-1-specific CD8+ T Cells Are Negatively Regulated by LAG-3 and PD-1 in Human Ovarian Cancer," Proceedings of the National Academy of Sciences

(56) References Cited

OTHER PUBLICATIONS of the United States of America 107(17):7875-7880, National Academy of Sciences, United states (Apr. 2010 ).
Nielsen, C., et al., "A putative regulatory polymorphism in PD-1 is associated with nephropathy in a population-based cohort of systemic lupus erythematosus patients," Lupus 13(7):510-516, SAGE, England (2004).
Nishimura, H., et al., "Autoimmune Dilated Cardiomyopathy in PD-1 Receptor-deficient Mice," Science 291(5502):319-322, American Association for the Advancement of Science, United States (Jan. 2001).
Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).
Okazaki, T., et al., "New Regulatory Co-receptors: Inducible co-stimulator and PD-1," Current Opinion in Immunology 14(6):779-782, Elsevier, England (Dec. 2002).
Okazaki, T., et al., "PD-1 and LAG-3 Inhibitory Co-receptors Act Synergistically to Prevent Autoimmunity in Mice," The Journal of Experimental Medicine 208(2):395-407, Rockefeller University Press, United states (Feb. 2011 ).
Okazaki, T., et al., "PD-1 immunoreceptor Inhibits B Cell Receptor-mediated Signaling by Recruiting src Homology 2-domain-containing Tyrosine Phosphatase 2 to Phosphotyrosine," Proceedings of the National Academy of Sciences 98(24):13866-13871, National Academy of Sciences, United States (Nov. 2001).
Ono Pharmaceutical Co., Ltd, "A full human anti-PD-1 antibody "ONO-4538/BMS-936558", Results from Phase 1 Study in Cancer Patients Published in New England Journal of Medicine (NEJM) and Presented at Annual Meeting of the American Society of Clinical Oncology (ASCO)," Jun. 4, 2012, [retrieved on May 24, 2018], Retrieved from the Internet: (URL:https://www.ono.co.jp/jpnw/PDF/n12_0604.pdf), Jun. 12, 2018, with translator certification statement, 9 pages.
Pardoll, D., "Chapter 14-Dendritic Cells and Coregulatory Signals: Immune Checkpoint Blockade to Stimulate Immunotherapy," Cancer Immunotherapy Immune Suppression and Tumor Growth, pp. 257-275, Elsevier Inc., United States (2007).
Pardoll, D.M., "The Blockade of Immune Checkpoints in Cancer Immunotherapy," Nature Reviews Cancer 12(4):252-264, Nature Publishing Group, England (Mar. 2012).
Prigent, P., et al., "Lymphocyte Activation Gene-3 Induces Tumor Regression and Antitumor Immune Responses," European Journal of Immunology 29(12):3867-3876, Wiley-VCH, Germany (Dec. 1999).
Prokunina, L. and Alarcon-Riquelme, M., "The Genetic Basis of Systemic Lupus Erythematosus—knowledge of Today and Thoughts for Tomorrow," Human Molecular Genetics 13(1):R143-R148, Oxford University Press, England (Apr. 2004).
Reply to Communication from the Examining Division dated Nov. 25, 2016 in European Application No. 13737946.7 filed on Jul. 2, 2013, pp. 115-119.
Robinson, N,E. and Robinson, A,B., "Molecular Clocks," Proceedings of the National Academy of Sciences of the United States of America 98(3):944-949, National Academy of Sciences, United states (Jan. 2001 ).
Rosenberg, S.A., et al., "Cancer Immunotherapy in Cancer: Principles & Practice of Oncology", 332-344, Lippincott Williams & Wilkins (2011).
Salama, A.D., et al., "Critical Role of the Programmed Death-1 (PD-1) Pathway in Regulation of Experimental Autoimmune Encephalomyelitis," The Journal of Experimental Medicine 198(1):71-78, The Rockefeller University Press, United States (Jul. 2003).
Sierro et al., "Expert Opinion on Therapeutic Targets",2010, vol. 15, pp. 91-101.
Subramanyam, M., et al., "Soluble Human Lymphocyte Activation Gene-3 Modulates Allospecific T Cell Responses," International Immunology 10(5):679-689, University Press, England (May 1998).

Supplementary European Search Report for EP Application No. 09807162.4, European Patent Office, Munich, Germany, dated Dec. 21, 2012, 9 pages.
Third Party Observation dated Oct. 7, 2016 for European Application No. 13737946.7 filed on Jul. 2, 2013, 17 pages.
Thomas, M.L., "Of ITAMs and ITIMs: Turning on and off the B Cell Antigen Receptor," The Journal of Experimental Medicine 181(6):1953-1956, The Rockefeller University Press, United States (Jun. 1995).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Triebel, F., et al., "LAG-3, A Novel Lymphocyte Activation Gene Closely Related to CD4," The Journal of Experimental Medicine 171(5):1393-1405, Rockefeller University Press, United States (May 1990).
Triebel, F., "LAG-3: A Regulator of T-cell and DC Responses and its Use in Therapeutic Vaccination," Trends in Immunology 24(12):619-622, Elsevier Science Ltd., England (Dec. 2003).
Tsai, P,K., et al., "Origin of the Isoelectric Heterogeneity of Monoclonal Immunoglobulin h1B4," Pharmaceutical Research 10(11):1580-1586, Kluwer Academic/Plenum Publishers, United states (Nov. 1993).
Vivier, E. and Daeron, M., "Immunoreceptor Tyrosine-based Inhibition Motifs," Immunology Today 18(6):286-291, Elsevier, England (Jun. 1997).
Vlasak, J., et al., "Identification and Characterization of Asparagine Deamidation in the Light Chain CDR1of a Humanized IgG1 Antibody," Analytical Biochemistry 392(2):145-154, Academic Press, United states (Sep. 2009 ).
Wolchok, J.D., et al., "Guidelines for the Evaluation of Immune Therapy Activity in Solid Tumors: Immune-related Response Criteria," Clinical Cancer Research 15(23):7412-7420, The Association, United States (2009).
Wolchok, J.D., et al., "Nivolumab Plus Ipilimumab in Advanced Melanoma," The New England Journal of Medicine 369(2):122-133, Massachusetts Medical Society, United States (Jul. 2013).
Workman, C.J. and Vignali, D.A., "Negative Regulation of T Cell Homeostasis by Lymphocyte Activation Gene-3 (CD223)," Journal of Immunology 174(2):688-695, American Association of Immunologists, United States (Jan. 2005).
Workman, C,J., et al., "LAG-3 Regulates Plasmacytoid Dendritic Cell Homeostasis," Journal of Immunology 182(4):1885-1891, American Association of Immunologists, United states (Feb. 2009).
Workman, C.J., et al., "Phenotypic Analysis of the Murine Cd4-related Glycoprotein, CD223 (LAG-3)," European Journal of Immunology 32(8):2255-2263, Wiley-VCH, Germany (Aug. 2002).
Torres, M and Casadevall, A., "The Immunoglobulin Constant Region Contributes to Affinity and Specificity," Trends in Immunology, 29(2):91-97, Elsevier Science Ltd, England (Feb. 2008).
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_01_23, 5 pages.
Co-Pending U.S. Appl. No. 16/108,973, inventor KORMAN; Alan. J., filed Aug. 22, 2018 (Unpublished).
Edwards, B.M., et al., "The Remarkable Flexibility of the Human Antibody Repertoire; Isolation of Over One Thousand Different Antibodies to a Single Protein, BLyS, " Journal of Molecular Biology, 334(1):103-118, Elsevier, England (Nov. 2003).
Khan, T and Salunke, D.M, "Adjustable Locks and Flexible Keys: Plasticity of Epitope-paratope Interactions in Germline Antibodies," Journal of Immunology 192(11):5398-5405, American Association of Immunologists, United States (Jun. 2014).
Poosarla, V.G., et al., "Computational De Novo Design of Antibodies Binding to a Peptide With High Affinity," Biotechnology and Bioengineering 114(6):1331-1342, Wiley, United States (Jun. 2017).
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_05_07, last accessed on Feb. 10, 2021, 4 pages.

(56) References Cited

OTHER PUBLICATIONS

Adib-Conquy, M., et al., "Effect of Amino Acid Substitutions in the Heavy Chain CDR3 of an Autoantibody on Its Reactivity," International Immunology 10(3):341-346, Oxford University Press, England (1998).

Beers, R., et al., "Immunotoxins With Increased Activity Against Epidermal Growth Factor Receptor vIII-expressing Cells Produced by Antibody Phage Display," Clinical Cancer Research 6(7):2835-2843, The Association, United States (2000).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Camacho, L.H., et al., "Phase I clinical trial of anti-CTLA4 human monoclonal antibody CP-675,206 in patients (pts) with advanced solid malignancies," Journal of Clinical Oncology 22(14S):Abstract 2505, 2004 ASCO Annual Meeting Proceedings (Post-Meeting Edition), 40$^{th}$ Annual Meeting, Jun. 5-8, New Orleans, LA, American Society of Clinical Oncology, United States (2004).

De Wildt, R.M.T., et al. , "Heavy Chain CDR3 Optimization of a Germline Encoded Recombinant Antibody Fragment Predisposed to Bind the U1A Protein," Protein Engineering 10(7):835-841, Oxford University Press, England (1997).

Greenberg, P.D. and Riddell, S.R., "Deficient Cellular Immunity-Finding and Fixing the Defects," Science 285(5427):546-551, American Association for the Advancement of Science, United States (1999).

Grosso, J.F., et al., "Functionally Distinct LAG-3 and PD-1 Subsets on Activated and Chronically Stimulated CD8 T Cells," The Journal of Immunology 182(11):6659-6669, The American Association of Immunologists, Inc., United States (Jun. 2009).

Hahne, M., et al., "Melanoma Cell Expression of Fas(Apo-1/CD95) Ligand: Implications for Tumor Immune Escape," Science 274(5291):1363-1366, American Association for the Advancement of Science, United States (1996).

Hall, B.L., et al., "A Single Amino Acid Mutation in CDR3 of the 3-14-9 L Chain Abolished Expression of the IDA 10-defined Idiotope and Antigen Binding," Journal of Immunology 149(5):1605-1612, American Association of Immunologists, United States (1992).

He, Y-F., et al., "Blocking Programmed Death-1 Ligand-PD-1 Interactions by Local Gene Therapy Results in Enhancement of Antitumor Effect of Secondary Lymphoid Tissue Chemokine," The Journal of Immunology 173(8):4919-4928, The American Association of Immunologists, United States (2004).

Holliger, P., et al., "'Diabodies': Small Bivalent and Bispecific Antibody Fragments," Proceedings of the National Academy of Sciences USA 90(14):6444-6448, National Academy of Sciences, United States (1993).

Howard, M. and Ogarra, A., "Biological Properties of Interleukin 10," Immunology Today 13(6):198-200, Elsevier Science Publishers, England (1992).

Hurwitz, A.A., et al., "CTLA-4 Blockade Synergizes With Tumor-derived Granulocyte-macrophage Colony-stimulating Factor for Treatment of an Experimental Mammary Carcinoma," Proceedings of the National Academy of Sciences of the United States of America 95(17):10067-10071, National Academy of Sciences, United States (1998).

Ito, D., et al., "Effective Priming of Cytotoxic T Lymphocyte Precursors by Subcutaneous Administration of Peptide Antigens in Liposomes Accompanied by Anti-CD40 and Anti-CTLA-4 Antibodies," Immunobiology 201(5):527-540, Elsevier, Netherlands (2000).

Kehrl, J.H., et al., "Production of Transforming Growth Factor β by Human T Lymphocytes and Its Potential Role in the Regulation of T Cell Growth," The Journal of Experimental Medicine 163(5):1037-1050, Rockefeller University Press, United States (1986).

Kelley, R.F. and O'Connell, M.P., "Thermodynamic Analysis of an Antibody Functional Epitope," Biochemistry 32(27):6828-6835, American Chemical Society, United States (1993).

Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870, American Society for Biochemistry and Molecular Biology, United States (1997).

Melero, I., et al., "Monoclonal Antibodies Against the 4-1BB T-cell Activation Molecule Eradicate Established Tumors," Nature Medicine 3(6):682-685, Nature Publishing Company, United States (1997).

Mokyr, M.B., et al., "Realization of the Therapeutic Potential of CTLA-4 Blockade in Low-dose Chemotherapy-treated Tumor-bearing Mice," Cancer Research 58(23):5301-5304, American Association for Cancer Research, United States (1998).

Poljak, R.J., "Production and Structure of Diabodies," Structure 2(12):1121-1123, Cell Press, United States (1994).

Ridge J.P., et al., "A Conditioned Dendritic Cell Can Be a Temporal Bridge Between a CD4+ T-helper and a T-killer Cell," Nature 393(6684):474-478, Nature Publishing Group, England (1998).

Weinberg, A.D., et al., "Engagement of the OX-40 Receptor in Vivo Enhances Antitumor Immunity," Journal of Immunology 164(4):2160-2169, American Association of Immunologists, United States (2000).

Office Action dated Jan. 8, 2018 in U.S. Appl. No. 15/021,102, filed Mar. 10, 2016, inventor Korman, A.J., et al., 12 pages.

Poirier, N., et al., "Antibody-mediated depletion of lymphocyte-activation gene-3 (LAG-3+)-activated T lymphocytes prevents delayed-type hypersensitivity in non-human primates" Clinical and Experimental Immunology 164(2):265-274, British Society for Immunology (2011).

Kallewaard, N.L., et al., "Functional Maturation of the Human Antibody Response to Rotavirus," Journal of Immunology 180(6):3980-3989, American Association of Immunologists, United States (Mar. 2008).

Wiens, G.D., et al., "Somatic Mutation in VH complementarity-determining Region 2 and Framework Region 2: Differential Effects on Antigen Binding and Ig selection," Journal of Immunology 159(3):1293-1302, American Association of Immunologists, United States (1997).

Barber, D.L., et al., "Restoring function in exhausted CD8 T cells during chronic viral infection," Nature 439:682-687, Nature Publishing Group, United Kingdom (2006).

Declaration of Jeanette L. Fairhurst in Grounds of Opposition mailed Aug. 20, 2020 in EP Application No. 1516647.8, European Patent Office, Germany, 12 pages.

Dyrberg, T., et al., "Peptides as antigens. Importance of orientation," The Journal of Experimental Medicine 164(4):1344-1349, Rockefeller University Press, United States (1986).

Exhibit 1 in Grounds of Opposition mailed Aug. 20, 2020, in EP Application No. 15156647.8, European Patent Office, Germany, 1 page.

Extended European Search Report dated Jul. 13, 2015, in EP Application No. 15156647.8, European Patent Office, Germany, 9 pages.

Grounds of Opposition mailed Aug. 20, 2020, in EP Application No. 1516647.8, European Patent Office, Germany, 86 pages.

Hong, S., et al., "Progress and Application of Humanization of Monoclonal Antibodies," Chinese Journal of Biologicals 21(1):70-73, Changchun Institute of Biological Products, China (2008).

Hoogenboom, H.R., et al., "Designing and optimizing library selection strategies for generating high-affinity antibodies," TibTech Library 15:62-70, Elsevier, Netherlands (1997).

Huard, B., et al., "CD4/major histocompatibility complex class II interaction analyzed with CD4- and lymphocyte activation gene-3 (LAG-3)-Ig fusion proteins," Eur. J. Immunol.25:2718-2721, Wiley-VCH, Germany (1995).

Huard, B., et al., "LAG-3 does not define a specific mode of natural killing in human," Immunology Letters 61:109-112, Elsevier, Netherlands (1998).

Imakiire, T., et al., "Generation, immunologic characterization and antitumor effects of human monoclonal antibodies for carcinoembryonic antigen," Int J Cancer 108(4):564-570, Wiley Online Publishing, United States (2004).

Jespers, L.S., et al., "Guiding the Selection of Human Antibodies from Phage Display Reperotires to a Single Epitope of an Antigen," Biotechnology 12:899-903, Nature Publishing Group, United Kingdom (1994).

(56) References Cited

OTHER PUBLICATIONS

Kaufmann, D.E., et al., "Upregulation of CTLA-4 by HIV-specific CD4+ T cells correlates with disease progression and defines a reversible immune dysfunction," Nature Immunology 8(11):1246-1254, Nature Publishing Group, United Kingdom (2007).
Response to communication in European Patent Application No. 15156647.8, dated Feb. 9, 2016, European Patent Office, Germany, 3 pages.
Response to communication in European Patent Application No. 15156647.8, dated Mar. 29, 2018, European Patent Office, Germany, 3 pages.
Perez De La Lastra, J.M., et al., "Epitope mapping of 10 monoclonal antibodies against the pig analogue of human membrane cofactor protein (MCP)," Immunology 96:663-670, Blackwell Science Ltd., United States (1999).
Shapira, M., et al., "Immunity and protection against influenza virus by synthetic peptide corresponding to antigenic sites of hemagglutinin," PNAS 81(8): 2461-2465, United States National Academy of Sciences, United States (1984).
Tanaka, T., et al., "Efficient generation of antibodies to oncoproteins by using synthetic peptide antigens," PNAS 82(10):3400-3404, United States National Academy of Sciences, United States (1985).
Workman, C.J., et al., "The CD4-related molecule, LAG-3 (CD223), regulates the expansion of activated T cells," Eur J. Immunol. 33(4):970-979, Wiley Online Library, United States (2003).
Cashion, M.P. and Long, T.E., "Biomimetic Design and Performance of Polymerizable Lipids," Accounts of Chemical Research 42(8):1016-1025, American Chemical Society, United States (Aug. 2009).
ATCC Product Data Sheet," A3.4H2 (ATCC® HB-12319™),"American Type Culture Collections, 2013. 2 pages.
ATCC Product Data Sheet," A3.6B10 (ATCC® HB-12318™),"American Type Culture Collections, 2013. 2 pages.
Anonymous: "A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas and Multiple Myeloma," ClinicaiTrials. gov Archive Identifier NCT02061761, accessed at https://clinicaltrials.gov/archive/NCT02061761/2014_11_20, accessed on Jun. 16, 2015, 5 pages.
Nivolumab, "Guide to Pharmacology," accessed at http://www.guidetopharmacology.org/GRAC/liganddisplayforward?ligandId=7335, last accessed Sep. 28, 2018, 1 page.
Office Action dated Apr. 28, 2020 in CN 201710463804.9, State Intellectual Property Office of People's Republic of China, China, 8 pages.
International Preliminary Report on Patentability and Written Opinion for Application Serial No. PCT/US2013/48999, dated Jan. 6, 2015, 7 pages.
Extended European Search Report for EP Application No. 17177885, Hague, Netherlands, dated Nov. 17, 2017.
Extended European Search Report for EP Application No. 09807162.4, European Patent Office, Munich, Germany, dated Dec. 21, 2012, 9 pages.
Office Action dated Nov. 26, 2021 in U.S. Appl. No. 16/376,394, filed Apr. 5, 2019, inventor Korman, A.J., et al., 16 pages.

\* cited by examiner

COMBINATION OF ANTI-LAG-3 ANTIBODIES AND ANTI-PD-1 ANTIBODIES TO TREAT TUMORS

RELATED APPLICATIONS

This application claims priority to U.S. Provisional Application No. 61/880,606, filed Sep. 20, 2013 and U.S. Provisional Application No. 62/014,471, filed Jun. 19, 2014. The contents of any patents, patent applications, and references cited throughout this specification are hereby incorporated by reference in their entireties.

BACKGROUND

Lymphocyte activation gene-3 (LAG-3; CD223) is a type I transmembrane protein that is expressed on the cell surface of activated CD4$^+$ and CD8$^+$ T cells and subsets of NK and dendritic cells (Triebel F, et al., *J. Exp. Med.* 1990; 171: 1393-1405; Workman C J, et al., *J. Immunol.* 2009; 182(4): 1885-91). LAG-3 is closely related to CD4, which is a co-receptor for T helper cell activation. Both molecules have 4 extracellular Ig-like domains and require binding to their ligand, major histocompatibility complex (MHC) class II, for their functional activity. In contrast to CD4, LAG-3 is only expressed on the cell surface of activated T cells and its cleavage from the cell surface terminates LAG-3 signaling. LAG-3 can also be found as a soluble protein but it does not bind to MHC class II and its function is unknown.

It has been reported that LAG-3 plays an important role in promoting regulatory T cell (Treg) activity and in negatively regulating T cell activation and proliferation (Workman C J, et al., *J. Immunol.* 2005; 174:688-695). Both natural and induced Treg express increased LAG-3, which is required for their maximal suppressive function (Camisaschi C, et al., *J. Immunol.* 2010; 184:6545-6551 and Huang C T, et al., *Immunity.* 2004; 21:503-513). Furthermore, ectopic expression of LAG-3 on CD4$^+$ effector T cells reduced their proliferative capacity and conferred on them regulatory potential against third party T cells (Huang C T, et al., *Immunity.* 2004; 21:503-513). Recent studies have also shown that high LAG-3 expression on exhausted lymphocytic choriomeningitis virus (LCMV)-specific CD8$^-$ T cells contributes to their unresponsive state and limits CD8$^-$ T cell antitumor responses (Blackburn S D, et al., *Nat. Immunol.* 2009; 10:29-37 and Grosso J F, et al., *J. Clin. Invest.* 2007; 117:3383-3392). In fact, LAG-3 maintained tolerance to self and tumor antigens via direct effects on CD8$^-$ T cells in 2 murine models (Grosso J F, et al., *J. Clin. Invest.* 2007; 117:3383-3392).

Immune tolerance observed in the setting of tumor development and tumor recurrence, however, seems to be mediated by the co-expression of various T cell negative regulatory receptors, not solely from LAG-3. Data from chronic viral infection models (Blackburn S D, et al., *Nat. Immunol.* 2009; 10:29-37, Grosso J F, et al., *J. Clin. Invest.* 2007; 117:3383-3392, and Lyford-Pike S, et al., *Cancer Res.* 2013; 73(6):1733-41), knock-out mice (Woo S R, et al., *Cancer Res.* 2012; 72:917-927; Okazaki T, et al., *J. Exp Med.* 2011; 208:395-407, and Bettini M. et al., *J. Immunol.* 2011; 187:3493-3498), tumor recurrence models (Goding S R, et al., *J. Immunol.* 2013; 190(9):4899-4909) and, to a more limited extent, human cancer patients (Goding S R, et al., *J. Immunol.* 2013; 190(9):4899-4909, Matsuzaki J, et al., *Proc. Natl. Acad. Sci., USA.* 2010; 107:7875-7880, and Gandhi M K, et al., *Blood.* 2006; 108:2280-2289) support a model wherein T cells that are continuously exposed to antigen become progressively inactivated through a process termed "exhaustion." Exhausted T cells are characterized by the expression of T cell negative regulatory receptors, predominantly CTLA-4, PD-1, and LAG-3, whose action is to limit the cell's ability to proliferate, produce cytokines, and kill target cells and/or to increase Treg activity. However, the timing and sequence of expression of these molecules in the development and recurrence of tumors have not been fully characterized.

Programmed Cell Death 1 (PD-1) is a cell surface signaling receptor that plays a critical role in the regulation of T cell activation and tolerance (Keir M E, et al., *Annu Rev Immunol* 2008; 26:677-704). It is a type I transmembrane protein and together with BTLA, CTLA-4, ICOS and CD28, comprise the CD28 family of T cell co-stimulatory receptors. PD-1 is primarily expressed on activated T cells, B cells, and myeloid cells (Dong H, et al., *Nat Med.* 1999; 5:1365-1369). It is also expressed on natural killer (NK) cells (Terme M, et al., *Cancer Res* 2011; 71:5393-5399). Binding of PD-1 by its ligands, PD-L1 and PD-L2, results in phosphorylation of the tyrosine residue in the proximal intracellular immune receptor tyrosine inhibitory domain, followed by recruitment of the phosphatase SHP-2, eventually resulting in down-regulation of T cell activation. One important role of PD-1 is to limit the activity of T cells in peripheral tissues at the time of an inflammatory response to infection, thus limiting the development of autoimmunity (Pardoll D M., *Nat Rev Cancer* 2012; 12:252-264). Evidence of this negative regulatory role comes from the finding that PD-1-deficient mice develop lupus-like autoimmune diseases including arthritis and nephritis, along with cardiomyopathy (Nishimura H, et al., *Immunity,* 1999; 11:141-151; and Nishimura H, et al., *Science,* 2001; 291: 319-322). In the tumor setting, the consequence is the development of immune resistance within the tumor microenvironment. PD-1 is highly expressed on tumor-infiltrating lymphocytes, and its ligands are up-regulated on the cell surface of many different tumors (Dong H, et al., *Nat Med* 2002; 8:793-800). Multiple murine cancer models have demonstrated that binding of ligand to PD-1 results in immune evasion. In addition, blockade of this interaction results in anti-tumor activity (Topalian S L, et al. *NEJM* 2012; 366(26):2443-2454; Hamid O, et al., *NEJM* 2013; 369:134-144). Moreover, it has been shown that inhibition of the PD-1/PD-L1 interaction mediates potent antitumor activity in preclinical models (U.S. Pat. Nos. 8,008,449 and 7,943,743).

Patients with metastatic or refractory solid tumors have very poor prognosis (Rosenberg S A, et al., *Cancer immunotherapy in Cancer: Principles & Practice of Oncology* (Eds DeVita V T, Lawrence T S and Rosenberg S A) 2011; 332-344 (Lippincott Williams & Wilkins, Philadelphia Pa.)). Despite advances in multimodal therapy, increases in overall survival in this patient population have been limited. Accordingly, it is an object of the present invention to provide improved methods for treating subjects with such tumors (e.g., advanced refractory solid tumors).

SUMMARY

Provided herein are methods for treating tumors in a human patient, particularly solid tumors (e.g., advanced refractory solid tumors), comprising administering to the patient a combination of an anti-LAG-3 antibody and an anti-PD-1 antibody, wherein the combination is administered (or is for administration) according to a particular clinical dosage regimen (i.e., at a particular dose amount and according to a specific dosing schedule). In one embodiment, the human patient suffers from melanoma, non-small cell lung cancer (NSCLC), virally-related cancer, head and neck cancer (HNC) or gastric adenocarcinoma.

An exemplary anti-LAG-3 antibody is BMS-986016 comprising heavy and light chains comprising the sequences shown in SEQ ID NOs:1 and 2, respectively, or antigen binding fragments and variants thereof. In other embodiments, the antibody comprises the heavy and light chain complementarity determining regions (CDRs) or variable regions (VRs) of BMS-986016. Accordingly, in one embodiment, the antibody comprises CDR1, CDR2, and CDR3 domains of the heavy chain variable (VH) region of BMS-986016 having the sequence shown in SEQ ID NO:3, and CDR1, CDR2 and CDR3 domains of the light chain variable (VL) region of BMS-986016 having the sequence shown in SEQ ID NO:5. In another embodiment, the antibody comprises CDR1, CDR2 and CDR3 heavy chain sequences set forth in SEQ ID NOs:7, 8, and 9, respectively, and CDR1, CDR2 and CDR3 light chain sequences as set forth in SEQ ID NOs:10, 11, and 12, respectively. In another embodiment, the antibody has VH and/or VL regions comprising the amino acid sequences set forth in SEQ ID NO:3 and/or SEQ ID NO:5, respectively. In another embodiment, the antibody comprises the VH and/or VL regions encoded by the nucleic acid sequences set forth in SEQ ID NO:4 and/or SEQ ID NO:6, respectively. In another embodiment, the antibody competes for binding with, and/or binds to the same epitope on LAG-3 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

An exemplary anti-PD-1 antibody is Nivolumab (also referred to as "5C4" in WO 2006/121168; and known as BMS-936558, MDX-1106 and ONO-4538) comprising heavy and light chains comprising the sequences shown in SEQ ID NOs:17 and 18, respectively, or antigen binding fragments and variants thereof. In other embodiments, the antibody comprises the heavy and light chain CDRs or VRs of BMS-936558. Accordingly, in one embodiment, the antibody comprises CDR1, CDR2, and CDR3 domains of the VH region of BMS-936558 having the sequence shown in SEQ ID NO:19, and CDR1, CDR2 and CDR3 domains of the VL region of BMS-936558 having the sequence shown in SEQ ID NO:21. In another embodiment, the antibody comprises heavy chain CDR1, CDR2 and CDR3 domains comprising the sequences set forth in SEQ ID NOs:23, 24, and 25, respectively, and light chain CDR1, CDR2 and CDR3 domains comprising the sequences set forth in SEQ ID NOs: 26, 27, and 28, respectively. In another embodiment, the antibody comprises VH and/or VL regions comprising the amino acid sequences set forth in SEQ ID NO: 19 and/or SEQ ID NO:21, respectively. In another embodiment, the antibody comprises the heavy chain variable (VH) and/or light chain variable (VL) regions encoded by the nucleic acid sequences set forth in SEQ ID NO:20 and/or SEQ ID NO:22, respectively. In another embodiment, the antibody competes for binding with, and/or binds to the same epitope on PD-1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:19 or SEQ ID NO:21).

Accordingly, in one aspect, methods of treating solid tumors (e.g., advanced refractory solid tumors) in a human patient are provided, the methods comprising administering to the patient, an effective amount of each of:

(a) an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5, (b) an anti-PD-1 antibody comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21, wherein the method comprises at least one administration cycle, wherein the cycle is a period of eight weeks, wherein for each of the at least one cycles, four doses of the anti-LAG-3 antibody are administered at a dose of 3, 20, 80, or 240 mg and four doses of the anti-PD-1 antibody are administered at a dose of 80 or 240 mg. In another embodiment, four doses of the anti-LAG-3 antibody are administered at a dose of about 0.03, 0.25, 1, or 3 mg/kg body weight and four doses of the anti-PD-1 antibody are administered at a dose of 1 or 3 mg/kg body weight.

In one embodiment, the anti-LAG-3 antibody and anti-PD-1 antibody are administered at the following doses:

(a) 3 mg anti-LAG-3 antibody and 80 mg of anti-PD-1 antibody;

(b) 3 mg anti-LAG-3 antibody and 240 mg of anti-PD-1 antibody;

(c) 20 mg anti-LAG-3 antibody and 240 mg of anti-PD-1 antibody;

(d) 80 mg anti-LAG-3 antibody and 240 mg of anti-PD-1 antibody; or (e) 240 mg anti-LAG-3 antibody and 240 mg of anti-PD-1 antibody.

In another embodiment, the anti-LAG-3 antibody and anti-PD-1 antibody are administered at the following doses:

(a) 0.03 mg/kg anti-LAG-3 antibody and 1 mg/kg of anti-PD-1 antibody;

(b) 0.03 mg/kg anti-LAG-3 antibody and 3 mg/kg of anti-PD-1 antibody;

(c) 0.25 mg/kg anti-LAG-3 antibody and 3 mg/kg of anti-PD-1 antibody;

(d) 1 mg/kg anti-LAG-3 antibody and 3 mg/kg of anti-PD-1 antibody; or (e) 3 mg/kg anti-LAG-3 antibody and 3 mg/kg of anti-PD-1 antibody.

In one embodiment, the dose of the anti-LAG-3 and/or anti-PD-1 antibody is calculated per mg/kg body weight. In another embodiment, the dose of the anti-LAG-3 and/or anti-PD-1 antibody is a flat-fixed dose. In another embodiment, an intermediate dose of LAG-3 and/or PD-1 is used. For example, LAG-3 could be administered at 0.4 mg/kg and PD-1 could be administered at 90 mg/kg. In another embodiment, dosage regimens are adjusted to provide the optimum desired response (e.g., an effective response).

In another embodiment, the anti-PD-1 antibody is administered on Days 1, 15, 29, and 43 of each cycle. In another embodiment, the anti-LAG-3 antibody is administered on Days 1, 15, 29, and 43 of each cycle. In another embodiment, the anti-PD-1 antibody is administered prior to administration of the anti-LAG-3 antibody. In another embodiment, the anti-PD-1 antibody is administered after administration of the anti-LAG-3 antibody. In another embodiment, the treatment consists of up to 12 cycles.

In one embodiment, the anti-PD-1 antibody and anti-LAG-3 antibody are administered as a first ("front") line of treatment (e.g., the initial or first treatment). In another embodiment, the anti-PD-1 antibody and anti-LAG-3 antibody are administered as a second line of treatment (e.g., after initial treatment with the same or a different therapeutic, including after relapse and/or where the first treatment has failed). The anti-LAG-3 and anti-PD-1 antibodies can be administered to a subject by any suitable means. In one embodiment, the antibodies are formulated for intravenous administration. In another embodiment, the antibodies are administered simultaneously (e.g., formulated together in a single formulation or concurrently as separate formulations). Alternatively, in another embodiment, the antibodies are administered sequentially (e.g., as separate formulations). In another embodiment the anti-LAG-3 antibody is administered within about 30 minutes (e.g., within about 29, 28, 27, 26, 25, 24, 23, 22, 21, 20, or less minutes) prior to administration of the anti-PD-1 antibody.

The efficacy of the treatment methods provided herein can be assessed using any suitable means. In one embodiment, the treatment produces at least one therapeutic effect selected from the group consisting of reduction in size of a tumor, reduction in number of metastatic lesions over time, complete response, partial response, and stable disease.

Also provided are kits that include a pharmaceutical composition containing an anti-LAG-3 antibody, such as BMS-986016, and an anti-PD-1 antibody, such as BMS-936558, and a pharmaceutically-acceptable carrier, in a therapeutically effective amount adapted for use in the methods described herein. In one embodiment, the kit comprises:

(a) a dose of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5;

(b) a dose of an anti-PD-1 antibody comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21; and (c) instructions for using the anti-LAG-3 antibody and anti-PD-1 antibody in a method of the invention.

In another aspect, an anti-LAG-3 antibody is provided, the anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5, for co-administration with an anti-PD-1 antibody comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21, in at least one cycle, wherein for each cycle four doses of the anti-LAG-3 antibody are administered at a dose of 3, 20, 80, or 240 mg and four doses of the anti-PD-1 antibody are administered at a dose of 80 or 240 mg. In another embodiment, four doses of the anti-LAG-3 antibody are administered at a dose of 0.03, 0.25, 1, or 3 mg/kg body weight and four doses of the anti-PD-1 antibody are administered at a dose of 1 or 3 mg/kg body weight.

In another aspect of the invention, the anti-PD-1 antibody in any of the aforementioned embodiments is replaced by, or combined with, an anti-PD-L1 or anti-PD-L2 antibody. Accordingly, the invention also features methods, compositions and kits for treating tumors in human patients using the above-described clinically effective dosages of an anti-LAG-3 antibody combined with the above-described clinically effective dosages of an anti-PD-1 antibody, wherein the dosage of the PD-1 antibody is replaced with the same dosage of an anti-PD-L1 or anti-PD-L2 antibody.

DETAILED DESCRIPTION

I. Definitions

Figure 1:
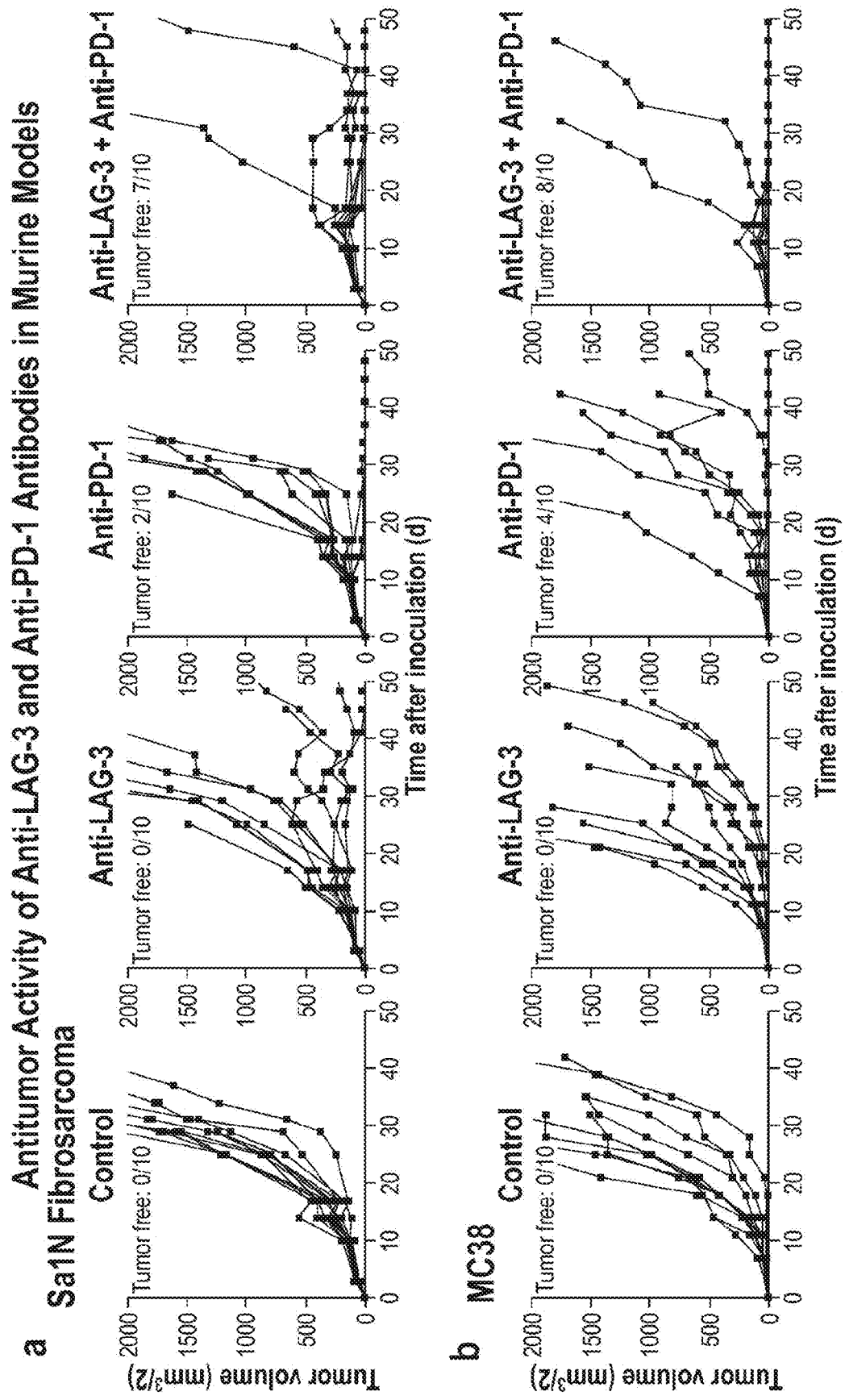
FIG. 1 shows inhibition of tumor growth in vivo using a combination treatment of an anti-LAG-3 antibody and an anti-PD-1 antibody in a murine tumor model.

As used herein, the term "subject" or "patient" is a human cancer patient (e.g., a patient having an advanced solid tumor, such as an advanced refractory solid tumor).

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of solid tumor. Effective treatment may refer to alleviation of at least one symptom of a solid tumor. Such effective treatment may, e.g., reduce patient pain, reduce the size and/or number of lesions, may reduce or prevent metastasis of a tumor, and/or may slow tumor growth.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of anti-LAG-3 antibody and the amount of anti-PD-1 antibody, in combination, clinically proven to affect a significant decrease in cancer or slowing of progression of cancer, such as an advanced solid tumor. As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent (e.g., the anti-LAG-3 antibody and/or anti-PD-1 antibody).

As used herein, a "body surface area (BSA)-based dose" refers to a dose (e.g., of the anti-LAG-3 antibody and/or anti-PD-1 antibody) that is adjusted to the body-surface area (BSA) of the individual patient. A BSA-based dose may be provided as mg/kg body weight. Various calculations have been published to arrive at the BSA without direct measurement, the most widely used of which is the Du Bois formula (see Du Bois D, Du Bois E F (June 1916) *Archives of Internal Medicine* 17 (6): 863-71; and Verbraecken, J. et al. (April 2006). *Metabolism—Clinical and Experimental* 55 (4): 515-24). Other exemplary BSA formulas include the Mosteller formula (Mosteller R D. *N Engl J Med.*, 1987; 317:1098), the Haycock formula (Haycock G B, et al., *J Pediatr* 1978, 93:62-66), the Gehan and George formula (Gehan E A, George S L, *Cancer Chemother Rep* 1970, 54:225-235), the Boyd formula (Current, J D (1998), *The Internet Journal of Anesthesiology* 2 (2); and Boyd, Edith (1935), University of Minnesota. The Institute of Child Welfare, Monograph Series, No. x. London: Oxford University Press), the Fujimoto formula (Fujimoto S, et al., Nippon Eiseigaku Zasshi 1968; 5:443-50), the Takahira formula (Fujimoto S, et al., Nippon Eiseigaku Zasshi 1968; 5:443-50), and the Schlich formula (Schlich E, et al., Ernährungs Umschau 2010; 57:178-183).

The term "antibody" describes polypeptides comprising at least one antibody-derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

The term "LAG-3" refers to Lymphocyte Activation Gene-3. The term "LAG-3" includes variants, isoforms, homologs, orthologs and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species, but not all other species (e.g., cross-react with monkey LAG-3 but not mouse LAG-3). The term "human LAG-3" refers to human sequence LAG-3, such as the complete amino acid sequence of human LAG-3 having Genbank Accession No. NP_002277 (SEQ ID NO:13). The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

The term "monkey LAG-3" is intended to encompass LAG-3 proteins expressed by Old World and New World monkeys, including but not limited to cynomolgus monkey LAG-3 and rhesus monkey LAG-3. A representative amino acid sequence for monkey LAG-3 is the rhesus monkey LAG-3 amino acid sequence which is also deposited as Genbank Accession No. XM_001108923. Another representative amino acid sequence for monkey LAG-3 is the alternative rhesus monkey sequence of clone pa23-5 as described in US 2011/0150892 A1. This alternative rhesus sequence exhibits a single amino acid difference, at position 419, as compared to the Genbank-deposited sequence.

A particular human LAG-3 sequence will generally be at least 90% identical in amino acid sequence to human LAG-3 of Genbank Accession No. NP_002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of Genbank Accession No. NP_002277. In certain embodiments, a human LAG-3 sequence will display no more than 10 amino acid differences from the LAG-3 sequence of Genbank Accession No. NP_002277. In certain embodiments, the human LAG-3 can display no more than 5, or even no more than 4, 3, 2, or 1 amino acid difference from the LAG-3 sequence of Genbank Accession No. NP_002277. Percent identity can be determined as described herein.

As used herein, the terms "Programmed Death 1," "Programmed Cell Death 1," "Protein PD-1," "PD-1," PD1," "PDCD1," "hPD-1" and "hPD-1" are used interchangeably, and include variants, isoforms, species homologs of human PD-1, and analogs having at least one common epitope with PD-1. The complete PD-1 sequence can be found under GenBank Accession No. U64863 (SEQ ID NO:29).

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) *Curr. Opin. Immunol.* 14: 391779-82; Bennett et al. (2003) *J Immunol* 170:711-8). The initial members of the family, CD28 and ICOS, were discovered by functional effects on augmenting T cell proliferation following the addition of monoclonal antibodies (Hutloff et al. *Nature* (1999); 397:263-266; Hansen et al. *Immunogenics* (1980); 10:247-260). PD-1 was discovered through screening for differential expression in apototic cells (Ishida et al. *EMBO J* (1992); 11:3887-95). The other members of the family, CTLA-4 and BTLA, were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) *Int Immunol* 8:765-72). PD-1 contains a membrane proximal immunoreceptor tyrosine inhibitory motif (ITIM) and a membrane distal tyrosine-based switch motif (ITSM) (Thomas, M. L. (1995) *J Exp Med* 181:1953-6; Vivier, E and Daeron, M (1997) *Immunol Today* 18:286-91). Although structurally similar to CTLA-4, PD-1 lacks the MYPPPY motif that is critical for B7-1 and B7-2 binding. Two ligands for PD-1 have been identified, PD-L1 and PD-L2, that have been shown to downregulate T cell activation upon binding to PD-1 (Freeman et al. (2000) *J Exp Med* 192:1027-34; Latchman et al. (2001) *Nat Immunol* 2:261-8; Carter et al. (2002) *Eur J Immunol* 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1, and the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

Consistent with PD-1 being an inhibitory member of the CD28 family, PD-1 deficient animals develop various autoimmune phenotypes, including autoimmune cardiomyopathy and a lupus-like syndrome with arthritis and nephritis (Nishimura et al. (1999) *Immunity* 11:141-51; Nishimura et al. (2001) *Science* 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003). *J Exp Med* 198:71-78; Prokunina and Alarcon-Riquelme (2004) *Hum Mol Genet* 13:R143; Nielsen et al. (2004) *Lupus* 13:510). In a murine B cell tumor line, the ITSM of PD-1 was shown to be essential to block BCR-mediated $Ca^{2+}$-flux and tyrosine phosphorylation of downstream effector molecules (Okazaki et al. (2001) *PNAS* 98:13866-71).

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and 5 analogs having at least one common epitope with hPD-L1. The complete hPD-L1 sequence can be found under GenBank Accession No. Q9NZQ7.

IIa. Anti-LAG-3 Antibodies

Anti-human-LAG-3 antibodies (or VH/VL domains derived therefrom) suitable for use in the invention can be generated using methods well known in the art. Alternatively, art recognized anti-LAG-3 antibodies can be used. For example, the anti-human LAG-3 antibody described in US2011/0150892 A1, the teachings of which are hereby incorporated by reference, and referred to as monoclonal antibody 25F7 (also known as "25F7" and "LAG3.1) can be used. Other art recognized anti-LAG-3 antibodies that can be used include IMP731 described in US 2011/007023, the teachings of which also are hereby incorporated by reference.

Antibodies that compete with any of the above-referenced art-recognized antibodies for binding to LAG-3 also can be used.

An exemplary anti-LAG-3 antibody is BMS-986016 comprising heavy and light chains comprising the sequences shown in SEQ ID NOs:1 and 2, respectively, or antigen binding fragments and variants thereof, as described in PCT/US13/48999, the teachings of which are hereby incorporated by reference.

In other embodiments, the antibody has the heavy and light chain CDRs or variable regions of BMS-986016. Accordingly, in one embodiment, the antibody comprises CDR1, CDR2, and CDR3 domains of the VH region of BMS-986016 having the sequence set forth in SEQ ID NO:3, and CDR1, CDR2 and CDR3 domains of the VL region of BMS-986016 having the sequence set forth in SEQ ID NO:5. In another embodiment, the antibody comprises CDR1, CDR2 and CDR3 domains comprising the sequences set forth in SEQ ID NOs:7, 8, and 9, respectively, and CDR1, CDR2 and CDR3 domains comprising the sequences set forth in SEQ ID NOs:10, 11, and 12, respectively. In another embodiment, the antibody comprises VH and/or VL regions comprising the amino acid sequences set forth in SEQ ID NO:3 and/or SEQ ID NO: 5, respectively. In another embodiment, the antibody comprises heavy chain variable (VH) and/or light chain variable (VL) regions encoded by the nucleic acid sequences set forth in SEQ ID NO:4 and/or SEQ ID NO:6, respectively. In another embodiment, the antibody competes for binding with and/or binds to the same epitope on LAG-3 as the above-mentioned antibodies. In another embodiment, the antibody binds an epitope of human LAG-3 comprising the amino acid sequence PGHPLAPG (SEQ ID NO:14). In another embodiment, the antibody binds an epitope of human LAG-3 comprising the amino acid sequence HPAAPSSW (SEQ ID NO:15) or PAAPSSWG (SEQ ID NO:16).

In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

IIb. Anti-PD-1 Antibodies

Anti-human-PD-1 antibodies (or VH and/or VL domains derived therefrom) suitable for use in the invention can be generated using methods well known in the art. Alternatively, art recognized anti-PD-1 antibodies can be used. For example, monoclonal antibodies 5C4 (referred to herein as Nivolumab or BMS-936558), 17D8, 2D3, 4H1, 4A11, 7D3, and 5F4, described in WO 2006/121168, the teachings of which are hereby incorporated by reference, can be used. Other known PD-1 antibodies include Lambrolizumab (MK-3475) described in WO 2008/156712, and AMP-514 described in WO 2012/145493, the teachings of which are hereby incorporated by reference. Further known PD-1 antibodies and other PD-1 inhibitors include those described in WO 2009/014708, WO 03/099196, WO 2009/114335 and WO 2011/161699, the teachings of which are hereby incorporated by reference. Antibodies that compete with any of these art-recognized antibodies or inhibitors for binding to PD-1 also can be used.

An exemplary anti-PD-1 antibody is BMS-936558 comprising heavy and light chains comprising the sequences shown in SEQ ID NOs:17 and 18, respectively, or antigen binding fragments and variants thereof.

In other embodiments, the antibody has heavy and light chain CDRs or variable regions of BMS-936558. Accordingly, in one embodiment, the antibody comprises CDR1, CDR2, and CDR3 domains of the VH of BMS-936558 having the sequence set forth in SEQ ID NO:19, and CDR1, CDR2 and CDR3 domains of the VL of BMS-936558 having the sequence set forth in SEQ ID NO:21. In another embodiment, the antibody comprises CDR1, CDR2 and CDR3 domains comprising the sequences set forth in SEQ ID NOs:23, 24, and 25, respectively, and CDR1, CDR2 and CDR3 domains comprising the sequences set forth in SEQ ID NOs:26, 27, and 28, respectively. In another embodiment, the antibody comprises VH and/or VL regions comprising the amino acid sequences set forth in SEQ ID NO: 19 and/or SEQ ID NO: 21, respectively. In another embodiment, the antibody comprises heavy chain variable (VH) and/or light chain variable (VL) regions encoded by the nucleic acid sequences set forth in SEQ ID NO:20 and/or SEQ ID NO:22, respectively. In another embodiment, the antibody competes for binding with and/or binds to the same epitope on PD-1 as the above-mentioned antibodies. In another embodiment, the antibody has at least about 90% variable region amino acid sequence identity with the above-mentioned antibodies (e.g., at least about 90%, 95% or 99% variable region identity with SEQ ID NO:19 or SEQ ID NO:21).

IIc. Anti-PD-L1 Antibodies

Anti-human-PD-L1 antibodies (or VH and/or VL domains derived therefrom) suitable for use in the invention can be generated using methods well known in the art. Alternatively, art recognized anti-PD-L1 antibodies can be used. For example, human anti-PD-L1 antibodies disclosed in U.S. Pat. No. 7,943,743, the contents of which are hereby incorporated by reference, can be used. Such anti-PD-L1 antibodies include 3G10, 12A4 (also referred to as BMS-936559), 10A5, 5F8, 10H10, 1B12, 7H1, 11E6, 12B7, and 13G4. Other art recognized anti-PD-L1 antibodies which can be used include those described in, for example, U.S. Pat. Nos. 7,635,757 and 8,217,149, U.S. Publication No. 2009/0317368, and PCT Publication Nos. WO 2011/066389 and WO 2012/145493, the teachings of which also are hereby incorporated by reference. Antibodies that compete with any of these art-recognized antibodies or inhibitors for binding to PD-L1 also can be used.

III. Pharmaceutical Compositions

Pharmaceutical compositions suitable for administration to human patients are typically formulated for parenteral administration, e.g., in a liquid carrier, or suitable for reconstitution into liquid solution or suspension for intravenous administration.

In general, such compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions (e.g., comprising an anti-LAG-3 or anti-PD-1 antibody). Liquid compositions for parenteral administration can be formulated for administration by injection or continuous infusion. Routes of administration by injection or infusion include intravenous, intraperitoneal, intramuscular, intrathecal and subcutaneous. In one embodiment, the anti-LAG-3 and/or anti-PD-1 antibodies are administered intravenously (e.g., in separate formulations or together (in the same formulation or in separate formulations)).

IV. Patient Populations

Provided herein are clinical methods for treating solid tumors cancer (e.g., advanced refractory solid tumors) in human patients using a combination of an anti-LAG-3 antibody and an anti-PD-1 antibody.

Examples of cancers that may be treated using the methods of the invention, include liver cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular 20 cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of 25 childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies 30 including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers.

In one embodiment, the human patient suffers from non-small cell lung cancer (NSCLC) or a virally-related cancer (e.g., a human papilloma virus (HPV)-related tumor) or gastric adenocarcinoma. In a particular embodiment, the HPV-related tumor is HPV+ head and neck cancer (HNC). In another particular embodiment, the gastric adenocarcinoma is associated with Epstein-Barr virus (EBV) infection.

Patients can be tested or selected for one or more of the above described clinical attributes prior to, during or after treatment.

V. Combination Therapy

Combination therapies provided herein involve administration of an anti-LAG-3 antibody and another antibody that blocks an inhibitory immune receptor (e.g., a receptor, which upon binding to its natural ligand, inhibits/neutralizes activity, such as cytotoxic activity), particularly an anti- PD-1 antibody, to treat subjects having solid tumors (e.g., advanced refractory solid tumors).

In one embodiment, the invention provides an anti-LAG-3 antibody and an anti-PD-1 antibody in combination according to a defined clinical dosage regimen, to treat subjects having a solid tumor (e.g., an advanced refractory solid tumor). In a particular embodiment, the anti-LAG-3 antibody is BMS-986016. In another embodiment, the anti-PD-1 antibody is BMS-936558. In another embodiment, dosage regimens are adjusted to provide the optimum desired response (e.g., an effective response).

As used herein, adjunctive or combined administration (coadministration) includes simultaneous administration of the compounds in the same or different dosage form, or separate administration of the compounds (e.g., sequential administration). Thus, the anti-LAG-3 and anti-PD-1 antibodies can be simultaneously administered in a single formulation. Alternatively, the anti-LAG-3 and anti-PD-1 antibodies can be formulated for separate administration and are administered concurrently or sequentially (e.g., one antibody is administered within about 30 minutes prior to administration of the second antibody).

For example, the anti-PD1 antibody can be administered first followed by (e.g., immediately followed by) the administration of the anti-LAG-3 antibody, or vice versa. In one embodiment, the anti-PD-1 antibody is administered prior to administration of the anti-LAG-3 antibody. In another embodiment, the anti-PD-1 antibody is administered after administration of the anti-LAG-3 antibody. In another embodiment, the anti-LAG-3 antibody and anti-PD-1 antibody are administered concurrently. Such concurrent or sequential administration preferably results in both antibodies being simultaneously present in treated patients.

VI. Treatment Protocols

Suitable treatment protocols for treating a solid tumor in a human patient include, for example, administering to the patient an effective amount of each of:

(a) an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5, (b) an anti-PD-1 antibody comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21, wherein the method comprises at least one administration cycle, wherein the cycle is a period of eight weeks, wherein for each of the at least one cycles, at least four doses of the anti-LAG-3 antibody are administered at a flat dose of about 1, 3, 10, 20, 50, 80, 100, 130, 150, 180, 200, 240 or 280 mg and at least four doses of the anti-PD-1 antibody are administered at flat dose of about 50, 80, 100, 130, 150, 180, 200, 240 or 280 mg. In another embodiment, four doses of the anti-LAG-3 antibody are administered at a dose of 0.01, 0.03, 0.25, 0.1, 0.3, 1 or 3, 5, 8 or 10 mg/kg body weight and four doses of the anti-PD-1 antibody are administered at a dose of 0.1, 0.3, 1, 3, 5, 8 or 10 mg/kg body weight.

In one embodiment, the anti-LAG-3 antibody and anti-PD-1 antibody are administered at the following doses:

(a) 3 mg anti-LAG-3 antibody and 80 mg of anti-PD-1 antibody;

(b) 3 mg anti-LAG-3 antibody and 240 mg of anti-PD-1 antibody;

(c) 20 mg anti-LAG-3 antibody and 240 mg of anti-PD-1 antibody;

(d) 80 mg anti-LAG-3 antibody and 240 mg of anti-PD-1 antibody; or (e) 240 mg anti-LAG-3 antibody and 240 mg of anti-PD-1 antibody.

In another embodiment, the anti-LAG-3 antibody and anti-PD-1 antibody are administered at the following doses:

(a) 0.3 mg/kg anti-LAG-3 antibody and 1 mg/kg of anti-PD-1 antibody;

(b) 0.3 mg/kg anti-LAG-3 antibody and 3 mg/kg of anti-PD-1 antibody;

(c) 0.25 mg/kg anti-LAG-3 antibody and 3 mg/kg of anti-PD-1 antibody;

(d) 1 mg/kg anti-LAG-3 antibody and 3 mg/kg of anti-PD-1 antibody; or (e) 3 mg/kg anti-LAG-3 antibody and 3 mg/kg of anti-PD-1 antibody.

In one embodiment, the dose of the anti-LAG-3 and/or anti-PD-1 antibody is calculated per body weight, e.g., mg/kg body weight. In another embodiment, the dose of the anti-LAG-3 and/or anti-PD-1 antibody is a flat-fixed dose. In another embodiment, the dose of the anti-LAG-3 and/or anti-PD-1 antibody is varied over time. For example, the anti-LAG-3 antibody and/or anti-PD-1 antibody may be initially administered at a high dose and may be lowered over time. In another embodiment, the anti-LAG-3 antibody and/or anti-PD-1 antibody is initially administered at a low dose and increased over time.

In another embodiment, the amount of the anti-LAG-3 and/or anti-PD-1 antibodies administered is constant for each dose. In another embodiment, the amount of antibody administered varies with each dose. For example, the maintenance (or follow-on) dose of the antibody can be higher or the same as the loading dose which is first administered. In another embodiment, the maintenance dose of the antibody can be lower or the same as the loading dose.

In another embodiment, the anti-LAG-3 and/or anti-PD-1 antibodies are formulated for intravenous administration. In one embodiment, the anti-PD-1 antibody is administered on Days 1, 15, 29, and 43 of each cycle. In another embodiment, the anti-LAG-3 antibody is administered on Days 1, 15, 29, and 43 of each cycle.

In other embodiments, the anti-LAG-3 and/or anti-PD-1 antibodies are administered once per week, once every or three two weeks, once per month or as long as a clinical benefit is observed or until there is a complete response, confirmed progressive disease or unmanageable toxicity.

In another embodiment, a cycle of administration is eight weeks, which can be repeated, as necessary. In another embodiment, the treatment consists of up to 12 cycles.

In another embodiment, 4 doses of the anti-PD-1 antibody are administered per eight week cycle. In another embodiment, 4 doses of the anti-LAG-3 antibody are administered per eight week cycle.

In another embodiment, the anti-PD-1 antibody and anti-LAG-3 antibody are administered as a first line of treatment (e.g., the initial or first treatment). In another embodiment, the anti-PD-1 antibody and anti-LAG-3 antibody are administered as a second line of treatment (e.g., after the initial or first treatment, including after relapse and/or where the first treatment has failed).

In another aspect, the invention features any of the aforementioned embodiments, wherein the anti-PD-1 antibody is replaced by, or combined with, an anti-PD-L1 or anti-PD-L2 antibody.

VII. Outcomes

With respect to target lesions, responses to therapy may include:

| | |
|---|---|
| Complete Response (CR) (RECIST V1.1) | Disappearance of all target lesions. Any pathological lymph nodes (whether target or non-target) must have reduction in short axis to <10 mm. |
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (ie Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (ie the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (ie the sum of the diameters at nadir of target lesions and any new measurable lesions increases by the required amount). Non-target lesions are not considered in the definition of Stable Disease and Partial Response. |

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, administration of effective amounts of the anti-LAG-3 antibody and anti-PD-1 antibody according to any of the methods provided herein produces at least one therapeutic effect selected from the group consisting of reduction in size of a tumor, reduction in number of metastatic lesions appearing over time, complete remission, partial remission, or stable disease. In still other embodiments, the methods of treatment produce a comparable clinical benefit rate (CBR=CR+PR+SD≥6 months) better than that achieved by an anti-LAG-3 antibody or anti-PD-1 antibody alone. In other embodiments, the improvement of clinical benefit rate is about 20% 20%, 30%, 40%, 50%, 60%, 70%, 80% or more compared to an anti-LAG-3 antibody or anti-PD-1 antibody alone.

VIII. Kits and Unit Dosage Forms

Also provided herein are kits which include a pharmaceutical composition containing an anti-LAG-3 antibody, such as BMS-986016, and an anti-PD-1 antibody, such as BMS-936558, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the anti-LAG-3 or anti-PD-1 antibody for a single administration in accordance with the methods provided above. Instruments or devices necessary for administering the pharmaceutical composition(s) also may be included in the kits. For instance, a kit may provide one or more pre-filled syringes containing an amount of the anti-LAG-3 or anti-PD-1 antibody.

In one embodiment, the present invention provides a kit for treating a solid tumor in a human patient, the kit comprising:

(a) a dose of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5;

(b) a dose of an anti-PD-1 antibody comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21; and (c) instructions for using the anti-LAG-3 antibody and anti-PD-1 antibody in the methods described herein.

The following examples are merely illustrative and should not be construed as limiting the scope of this disclosure in any way as many variations and equivalents will become apparent to those skilled in the art upon reading the present disclosure.

The contents of all references, GenBank entries, patents and published patent applications cited throughout this application are expressly incorporated herein by reference.

EXAMPLES

Example 1: Pre-Clinical Pharmacology of Anti-PD-1 Antibody (BMS-936558)

BMS-936558 is a fully human, IgG4 (kappa) isotype monoclonal antibody that binds to PD-1 with nanomolar affinity as measured by surface plasmon resonance using a Biacore® biosensor system and a high degree of specificity, thus precluding binding to its ligands PD-L1 and PD-L2. BMS-936558 does not bind other related family members, such as BTLA, CTLA-4, ICOS or CD28. Pre-clinical testing of BMS-936558 demonstrated that binding to PD-1 results in enhanced T cell proliferation and release of interferon-gamma (IFN-gamma) in vitro. The heavy and light chain amino acid sequences of BMS-936558 are provided in SEQ ID NOs: 1 and 2, respectively.

Example 2: In Vivo Toxicity of Anti-PD-1 Antibody Novolumab (BMS-936558)

Toxicology studies in cynomolgus monkeys confirmed that BMS-936558 was well tolerated at doses up to 50 mg/kg given twice weekly for 27 doses. Drug-related findings were limited to a reversible decrease in triiodothyronine (T3) by 28%, without concomitant abnormalities in other markers of thyroid function (data not shown).

Example 3: Clinical Pharmacology and Safety of Anti-PD-1 Antibody (BMS-936558)

The overall safety experience with BMS-936558, as a monotherapy or in combination with other therapeutics, is based on experience in approximately 1500 subjects treated to date. In general for monotherapy, the safety profile is similar across tumor types. The one exception is pulmonary inflammation adverse events (AEs) which may be numerically greater in subjects with NSCLC because in some cases, it can be difficult to distinguish between BMS-936558-related and unrelated causes of pulmonary symptoms and radiographic changes. The safety profile is generally consistent across completed and ongoing clinical trials with no maximum tolerated dose reached at any dose tested up to 10 mg/kg. There was no pattern in the incidence, severity, or causality of adverse events to BMS-936558 dose level.

Study CA209003 has contributed to most of the clinical experience with BMS-936558 in subjects with NSCLC and other solid malignancies to date. CA209003 was a Phase 1 multi-dose escalation study in subjects with previously treated advanced or metastatic melanoma, RCC, NSCLC, colorectal cancer, or hormone-refractory prostate cancer. In CA209003, subjects were administered BMS-936558 intravenously every 2 weeks with doses of 0.1, 0.3, 1, 3, or 10 mg/kg. No maximum tolerated dose was identified in CA209003. The maximum dose level evaluated was 10 mg/kg. The incidence, severity, and relationship of adverse events were generally similar across dose levels and tumor types.

As of 3 Jul. 2012, 296 (97.4%) out of 304 subjects treated with BMS-936558 had at least 1 reported adverse event regardless of causality. There was no pattern in the incidence, severity, or relationship of adverse events to the BMS-936558 dose level. Treatment-related adverse events of any grade occurred in 220 (72.4%) of subjects. The most frequent drug-related adverse events occurring in >5% of subjects included fatigue (25.7%), rash (13.5%), diarrhea (11.8%), pruritus (10.2%), nausea (7.9%), decreased appetite (7.9%), hemoglobin decreased (5.9%), and pyrexia (5.3%). Most treatment-related adverse events were low grade (Grade 1 or 2). Treatment-related high-grade (Grade 3 or 4) adverse events were reported in 45 (14.8%) of subjects, with the most common being fatigue (1.6%), decreased appetite (1.0%), and diarrhea (1.0%). At least one serious adverse event (SAE) was reported for 150 (49.3%) of the 304 subjects at all dose levels. Grade 3-4 SAEs were reported for 23 subjects (7.6%). Drug-related SAEs of any grade occurred in 11.5% of subjects. Grade 3-4 drug-related SAEs reported in at least 2 subjects included diarrhea (3 subjects [1.0%]), pneumonitis (3 subjects [1.0%]), pneumonia (2 subjects [0.7%]), and lipase increased (2 subjects [0.7%]). Similar to the overall adverse event profile, there was no apparent relationship in the incidence or severity of drug-related adverse events to BMS-936558 dose level. There were no apparent differences in the frequency of adverse events based on subjects' tumor type.

Selected treatment-related adverse events have occurred with low frequency (<5%), but are considered clinically meaningful because they require greater vigilance for early recognition and prompt intervention. These adverse events include alanine aminotransferase (ALT) increased (4.3%), aspartate aminotransferase (AST) increased (3.6%), pneumonitis (3.3%), hypothyroidism (3.0%), hyperthyroidism (1.3%), adrenal insufficiency (0.7%), and colitis (0.7%). Grade 3-4 events of pneumonitis were reported in 3 subjects (1.0%) as described above (1 event was Grade 4). Grade 3 events of colitis, ALT increased, and AST increased were reported in 2 subjects (0.7%) each. Grade 3 events of adrenal insufficiency, hyperthyroidism, and hypothyroidism were reported in 1 subject (0.3%) each. Because of the potential for clinically meaningful BMS-936558-related adverse events requiring early recognition and prompt intervention, management algorithms have been developed for suspected pulmonary toxicity, diarrhea or suspected colitis, hepatotoxicity, endocrinopathy, and nephrotoxicity.

Treatment-related adverse events leading to discontinuation were reported in 18 (5.9%) of the 304 treated subjects on CA209003. The only events reported in more than 1 subject were pneumonitis (4 subjects [1.3%]) and hepatitis (2 subjects [0.7%]). There were 3 (1.0%) drug-related deaths; each occurred after the development of pneumonitis. The safety of BMS-936558 in combination with other therapeutics is being explored in several ongoing clinical trials.

Example 4: Pharmacokinetics of Anti-PD-1 Antibody (BMS-936558)

Single-dose pharmacokinetics (PK) of BMS-936558 were evaluated in 39 subjects with multiple tumor types in CA209001 in the dose range of 0.3 to 10 mg/kg. The median Tmax across dose levels ranged from 1.6 to 3.1 hours with individual values ranging from 0.9 to 7 hours. The PK of BMS-936558 was linear in the range of 0.3 to 10 mg/kg with dose-proportional increase in Cmax and AUC(INF) and low to moderate intersubject variability was observed at each dose level (i.e., coefficient of variation [CV] ranging from 16 to 45%). Geometric mean clearance (CLT) after a single IV dose ranged from 0.13 to 0.19 mL/h/kg, while mean volume of distribution (Vz) varied between 83 to 113 mL/kg across doses. The mean terminal T-HALF of BMS-936558 was 17 to 25 days, consistent with half-life of endogenous IgG4, indicating that the elimination mechanism of BMS-936558 may be similar to IgG4. Both elimination and distribution of BMS-936558 appeared to be independent of dose within the dose range studied. In a multiple dose study of multiple tumor types (CA209003), available data from 128 subjects, mean T-HALF was 21-24 hours and median T-max ranged from 0.6 to 3.3 across dose levels, which aligns with the single dose data.

Example 5: Phase I Clinical Trial with Anti-PD-1 Antibody (BMS-936558)

BMS-936558 has demonstrated clinical activity in a completed Phase 1 single-dose study and 2 ongoing multiple-dose escalation studies (Phase 1 monotherapy: CA209003 and Phase 1b combination therapy with ipilimumab) in subjects with NSCLC, melanoma, RCC, and other malignancies. Tumor response was determined by modified Response Evaluation Criteria in Solid Tumors (RECIST) established by the NCI. The evaluable population consists of 294 subjects with a variety of solid tumor malignancies (melanoma, n=138; NSCLC, n=122; RCC, n=34) who are currently being treated with nivolumab.

In CA209003, an objective response rate (ORR) of 31.1% (33 of 106 response-evaluable subjects) was reported in subjects with melanoma treated with BMS-936558 monotherapy every 2 weeks (Q2W) at doses ranging from 0.1 to 10 mg/kg. The majority of responses were durable and exceeded 6 months.

In the most active dose range (3 to 10 mg/kg), an ORR of 13.5% to 27.8% was reported among subjects with NSCLC with a 24-week progression-free survival rate (PFSR) of 23% to 51%. Durable responses were observed in both squamous and non-squamous subtypes.

Of the 34 response-evaluable RCC subjects in CA209003, responses were reported in both the 1-mg/kg (5 of 18 subjects, 27.8%) and 10-mg/kg (5 of 16 subjects, 31.3%) treatment groups. Estimated progression-free survival rate (PFSR) at 24 weeks was 50% in the 1-mg/kg and 67% in the 10-mg/kg BMS-936558 treatment groups.

Preliminary results from the Phase 1b study of combination therapy with BMS-936558 and ipilimumab suggest an advantage in combining two T cell-targeted therapies for subjects with melanoma. In the 0.3 mg/kg BMS-936558+3 mg/kg ipilimumab treatment group, responses were observed in 5 out of 14 evaluable subjects (35.7%, 1 complete response and 2 partial responses by conventional modified World Health Organization [mWHO] criteria, and 2 partial responses by immune-related mWHO criteria). In the 1 mg/kg BMS-936558+3 mg/kg ipilimumab treatment group, responses were observed in 9 out of 15 evaluable subjects (60%, 3 CRs and 6 PRs; all by conventional mWHO criteria). In the 3 mg/kg BMS-936558+3 mg/kg ipilimumab treatment group, objective responses were observed in 4 out of 6 evaluable subjects (66.7%, 3 partial responses by conventional mWHO criteria and 1 partial response by immune-related mWHO criteria). Further details are provided by Wolchok et al. (2013) NEJM 369 (2):122-33, and/or PCT/US2013/040764.

Example 6: Pre-Clinical Pharmacology of Anti-LAG-3 Antibody (BMS-986016)

BMS-986016 is a fully human antibody specific for human LAG-3 that was isolated from immunized transgenic mice expressing human immunoglobulin genes. It is expressed as an IgG4 isotype antibody that includes a stabilizing hinge mutation (S228P) for attenuated Fc receptor binding in order to reduce or eliminate the possibility of antibody- or complement-mediated target cell killing. The heavy and light chain amino acid sequences of BMS-986016 are provided in SEQ ID NOs:17 and 18, respectively.

The ability of BMS-986016 to bind recombinant human LAG-3 antigen was determined using Biacore and enzyme-linked immunosorbent assay (ELISA). Binding to human and primate LAG-3+ transfectants and to activated human or primate T cells was measured using flow cytometric and Scatchard analyses. BMS-986016 binds to human LAG-3 with high affinity ($K_D$=0.12-0.5 nM), and inhibits the binding of LAG-3 to cells expressing its ligand, MHC class II (IC50, 0.67 nM). BMS-986016 binds to cynomolgus LAG-3 on transfected CHO cells and on activated cynomolgus T cells with a lower affinity (EC50, 21.5-34.3 nM) than to activated human T cells. A high concentration of BMS-986016, in the absence of secondary co-stimulation, elicits no measurable cytokine response from cultured human peripheral blood cells nor does the drug mediate measurable antibody-dependent or complement-dependent killing of target cells. BMS-986016 promotes the activation of an antigen-specific mouse T cell hybridoma expressing human LAG-3 in co-culture with an MHC class II-positive antigen-presenting cell. In addition, BMS-986016 enhances activation of human T cells in superantigen stimulation assays when added alone or in combination with BMS-936558 (anti-PD-1 antibody).

Example 7: Toxicity of Anti-LAG-3 Antibody (BMS-986016) Alone or in Combination with Anti-PD-1 Antibody (BMS-936558)

The following preclinical toxicology studies were performed:

A. Four-Week Intermittent (QW) Intravenous Exploratory Combination Pharmacodynamic and Toxicity Study in Cynomolgus Monkeys with Anti-LAG3.1 Antibody (a Precursor of BMS-986016) and BMS-936558

The key results were as follows. Anti-LAG3.1 administered at 50 mg/kg/week, alone or in combination with 50 mg/kg/week BMS-936558, did not result in any adverse changes. No-observed-adverse-effect level (NOAEL) for single-agent anti-LAG3.1 was considered to be 50 mg/kg/week (AUC[0-168 h]=231,000 μg·h/mL), and NOAEL for anti-LAG3.1 in combination with 50 mg/kg/week BMS-936558 was considered to be 50 mg/kg/week (mean anti-LAG3.1 AUC[0-168 h]=210,000 μg·h/mL; mean BMS-936558AUC[0-168h]=159,500 μg·h/mL).

B. GLP-Compliant Four-Week Intravenous Combination Toxicity Study in Cynomolgus Monkeys with a 6-Week Recovery with BMS-986016 and BMS-936558

The key results were as follows. Single-agent BMS-986016 administered at up to 100 mg/kg/week did not result in adverse changes. Single-agent BMS-936558 administered at 50 mg/kg/week resulted in slight to minimal non-reversible lymphoplasmacytic inflammation of the choroid plexus of the brain, which was considered non-adverse given the lower severity and incidence of the lymphoplasmacytic inflammation compared to combination treatment with BMS-986016 and BMS-936558, lack of vasculitis or tissue destruction, and absence of clinical manifestations during the course of treatment. Combined administration of BMS-986016 and BMS-936558 (100 and 50 mg/kg/week, respectively) resulted in moribundity of 1 male out of 9 monkeys on study Day 29. From Days 26 to 29, this monkey presented with elevated body temperature, shivers, red or clear nasal discharge, fecal changes (unformed, scant or absent feces), decreased feeding behavior, mild dehydration, sneezing, decreased activity, and hunched posture. After 2 days of veterinary care and antibiotic treatment, this animal did not show any improvement and was euthanized on Day 29 for poor clinical condition.

There were no remarkable gross necropsy findings. Histopathological findings in this monkey included: slight lymphoplasmacytic inflammation of the choroid plexus; minimal to moderate lymphohistocytic inflammation of the vasculature of the brain parenchyma, meninges, spinal cord (cervical and lumbar); and minimal to moderate mixed cell inflammation of the epididymes, seminal vesicles and testes. Clinical pathology changes indicated decreases in red blood cell count, hemoglobin concentration and hematocrit whose cause was unclear, and an increase in fibrinogen correlating with the inflammation observed in the central nervous system (CNS) and male reproductive tract.

Additional histopathological findings upon combination administration of BMS-986016 and BMS-936558 (100 and 50 mg/kg/week, respectively) were limited to minimal to slight non-reversible lymphoplasmacytic inflammation of the choroid plexus in the brain in 7 of 8 remaining monkeys, and minimal lymphohistocytic inflammation of the vasculature of the brain parenchyma in 1 of 8 remaining monkeys, whose reversibility could not be assessed.

NOAEL for single-agent BMS-986016 was considered to be 100 mg/kg/week (mean AUC[0-168h]=474,000 μg·h/mL); NOAEL for single-agent BMS-936558 was considered to be 50 mg/kg/week (mean AUC[0-168h]=193,000 μg·h/mL); NOAEL for combination of BMS-986016 and BMS-936558 was not determined. However, the combination therapy was generally well tolerated and clinical signs of toxicity were observed in only 1 of 9 monkeys (approximately 10%). Therefore, 100/50 mg/kg/week BMS-986016/nivolumab (mean BMS-986016 AUC[0-168h]=514,000 μg·h/mL; mean nivolumab AUC[0-168h]=182,000 μg·h/mL) was considered the STD10.

The doses administered (100 mg/kg BMS-986016 and 50 mg/kg BMS-936558) are ≥10 times higher than the maximum doses proposed for the current study. The starting dose of 20 mg (0.25 mg/kg) for BMS-986016 monotherapy (Part A) is less than ¹/₁₀ of the human equivalent of the cynomolgus monkey NOAEL (636 mg; 8.0 mg/kg), and is below the HED after a linear adjustment of the NOAEL target exposure for the highest affinity difference estimate of 265-fold (24 mg; 0.30 mg/kg). The calculated safety multiple for exposures at the 20 mg (0.25 mg/kg) starting dose is 315-fold based on the cynomolgus monkey NOAEL of 100 mg/kg/week without accounting for affinity differences.

The starting dose of 3 mg (0.03 mg/kg) for BMS-986016 for the combination therapy (Part B) is based on a linear adjustment of the cynomolgus monkey STD10 for the 265-fold highest affinity difference estimate with an added 10-fold safety factor. The maximum recommended starting dose (MRSD) for BMS-986016 based on a 100 mg/kg/week STD10 is 0.03 mg/kg in humans. The starting dose of 80 mg (1 mg/kg) for BMS-936558 for the combination therapy (Part B) is based on known human BMS-936558 PK parameters with an added 10-fold safety factor. The MRSD for BMS-936558 based on the 50 mg/kg/week cynomolgus monkey STD10 is 4.3 mg/kg in humans, and has been further reduced to identify a dose with acceptable levels of adverse events.

C. GLP-Compliant Tissue Cross Reactivity Study in Human and Select Cynomolgus Monkey Tissues with BMS-986016.

Positive staining with BMS-986016-FITC was observed in the plasma membrane or plasma membrane granules following human tissues: mononuclear leukocytes of the urinary bladder, blood cells, colon—large intestine, eye, esophagus, small intestine, stomach, kidney, lung, lymph node, placenta, salivary gland, skin, spleen, thymus, tonsil, uterus-cervix, and uterus-endometrium; and hematopoetic cells of the bone marrow. In addition, staining with BMS-986016-FITC was observed in the cytoplasm of the human pituitary endocrine cell epithelium. Within the limited panel of cynomolgus monkey tissues evaluated, staining with BMS-986016-FITC was observed in the plasma membrane or plasma membrane granules of the mononuclear leukocytes of the spleen. With scientific reports of LAG-3-expressing cells in germinal centers and interfollicular T-cell areas of normal human lymphoid tissues (lymph node, tonsil, spleen, thymus, bone marrow and mucosal-associated lymphoid tissue) and having the morphology and distribution of lymphocytes, the staining of mononuclear leukocytes and hematopoietic cells with BMS-986016-FITC in this study (in the human and cynomolgus monkey tissues) was anticipated. Given that LAG-3 mRNA is expressed in the human pituitary and LAG3.1-G4P-FITC staining was observed in adenohypophysis of the human pituitary in a pilot tissue cross reactivity study, BMS-986016-FITC staining of human pituitary endocrine cell epithelium cytoplasm and cytoplasmic granules was also anticipated. Although BMS-986016 is not expected to have access to the cytoplasmic compartment in vivo and the repeat-dose toxicology studies in monkeys showed no effects on the pituitary gland, these findings may be of clinical significance.

D. In Vitro Cytokine Release and Lymphocyte Activation Assessment with BMS-986016 Using Human Peripheral Blood Mononuclear Cells.

BMS-986016 did not induce cytokine release when presented to human PBMCs regardless of concentration, donor, or incubation time. The levels of cytokines observed were either at or near the assay lower limits of quantification with no evidence of dose-dependence or pattern across donors (IL-1β, IL-2, IL-5, IL-10, IL-12p70, and IFN-γ) or were generally overlapping with cytokine levels from PBMCs incubated with negative controls (IL-6, IL-8, TNF-α).

Consistent with the lack of cytokine release, there was no evidence that BMS-986016 induced T or NK cell activation, as measured by surface expression of CD25 and CD69. Expression levels of these markers on T and NK cells following stimulation with BMS-986016 were similar to those observed upon stimulation with negative controls.

Overall, these data indicate that BMS-986016 does not possess agonistic potential to induce either T or NK cellular activation or cytokine release.

Example 8: Preclinical Pharmacokinetics of Anti-LAG-3 Antibody (BMS-986016)

In accordance with regulatory guidelines for biotechnology-derived pharmaceuticals (ICH Harmonised Tripartite Guideline, S6(R1) Preclinical Safety Evaluation of Biotechnology-Derived Pharmaceuticals. International Conference on Harmonisation, 2011), no metabolism studies with BMS-986016 have been conducted in animals. The expected in vivo degradation of monoclonal antibodies (mAbs) is to small peptides and amino acids via biochemical pathways that are independent of cytochrome P450 enzymes.

BMS-986016 demonstrated favorable pharmacokinetic (PK) properties in cynomolgus monkeys. From both single-dose and repeat-dose IV PK studies, BMS-986016 decayed bi-exponentially and the exposure was approximately dose-proportional. The systemic clearance (CLTp) ranges from 0.12 to 0.22 mL/h/kg and a terminal half-life (T-HALF) 133 to 414 hours. The volume of distribution at steady state (Vss) was 62 to 72 mL/kg, suggesting limited distribution outside the plasma. Anti-BMS-986016 antibodies were detected in some monkeys but the presence of anti-BMS-986016 antibodies appeared to have no impact on BMS-986016 exposure.

Example 9: Inhibition of Tumor Growth In Vivo by Combination Treatment with Anti-LAG-3 Antibody and Anti-PD-1 Antibody An experiment was conducted in a murine tumor model to test the hypothesis that the combination of anti-LAG-3 and anti-PD-1 would potentiate anti-tumor efficacy. These studies evaluated tumor growth inhibition in syngeneic tumor models (Sa1N fibrosarcoma and MC38 colon adenocarcinoma) and monitored acceleration of autoimmunity in the non-obese diabetic (NOD) model. Anti-LAG-3 antibody administration resulted in both overall tumor growth inhibition and an increase in the number of tumor-free (TF) mice in those treatment groups, as shown in FIG. 1. Anti-LAG-3 antibody administered in combination with anti-PD-1 antibody provided enhanced anti-tumor activity above the activity of either agent alone. For example, in multiple Sa1N tumor models, anti-LAG-3 antibody resulted in 20%-30% TF mice compared to control and anti-PD-1 antibody-treated mice (0%-10% TF mice), while the combination of anti-LAG-3 and anti-PD-1 antibodies resulted in 60%-90% TF mice. In the MC38 model, anti-LAG-3 antibody showed modest tumor growth inhibition alone, but when administered in combination with anti-PD-1 antibody, resulted in enhanced antitumor activity above that observed for anti-PD-1 antibody alone (80% vs. 40% TF mice, respectively).

Example 10: Phase 1 Trial in Patients Having Solid Tumors

A phase 1 trial of anti-LAG-3 antibody (BMS-986016) and anti-PD-1 antibody (BMS-936558) is conducted in patients having advanced solid tumors to demonstrate the efficacy of administering BMS-986016 and BMS-936558 as a combination treatment.

1. Objectives

The primary objective of the study is to assess the safety and tolerability of BMS-986016 given in combination with BMS-936558 and to identify dose limiting toxicities (DLTs) and the maximally tolerated dose (MTD) of the combination, in subjects with advanced solid tumors.

Secondary objectives include assessing the preliminary anti-tumor activity of the combination of BMS-986016 and BMS-936558 in subjects with advanced solid tumors, characterizing the pharmacokinetics (PK) of BMS-986016 and BMS-936558 when co-administered, monitoring immunogenicity of BMS-986016 and BMS-936558 administered as combination therapy, and assessing the effect of BMS-986016 and BMS-936558 on corrected QT ("QTc"). Additional exploratory objectives include assessing the pharmacodynamic effects of BMS-986016 and BMS-936558 combination therapy based on select biomarkers in the peripheral blood and tumor biopsy specimens, characterizing T cell function during BMS-986016 and BMS-936558 combination therapy, assessing the 2-year landmark overall survival in subjects treated with BMS-986016 and BMS-936558, exploring preliminary antitumor activity of BMS-986016 and BMS-936558 combination therapy in subjects with advanced solid tumors, characterizing pharmacokinetics and exposure-response relationships in subjects treated with BMS-986016 and BMS-936558, and investigating the relationship between clinical efficacy and selected peripheral and tumor biomarkers.

2. Study Design and Duration

Figure 2A:
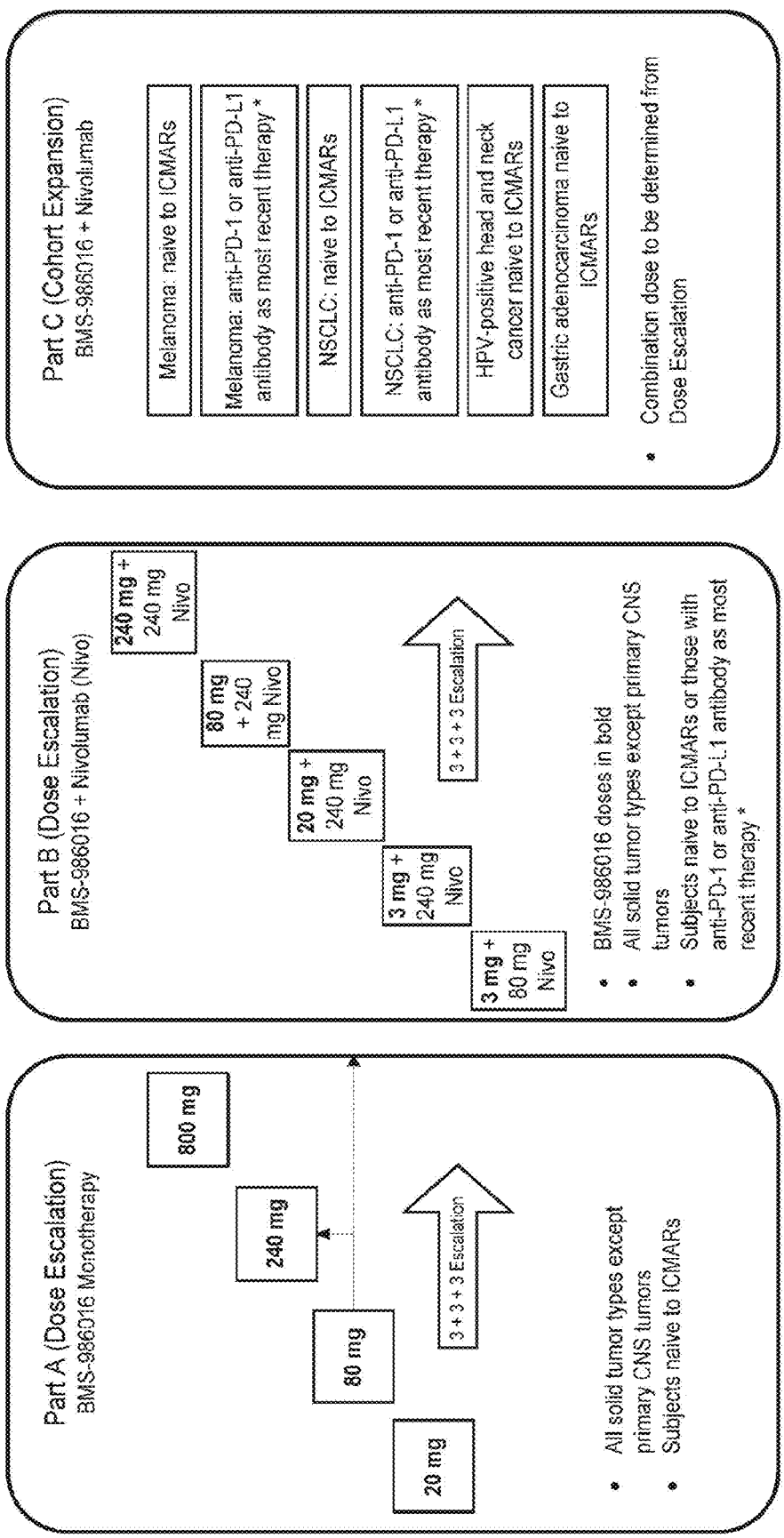
FIGS. 2A and 2B are schematics illustrating the parts of a phase I clinical trial.
Figure 2B:
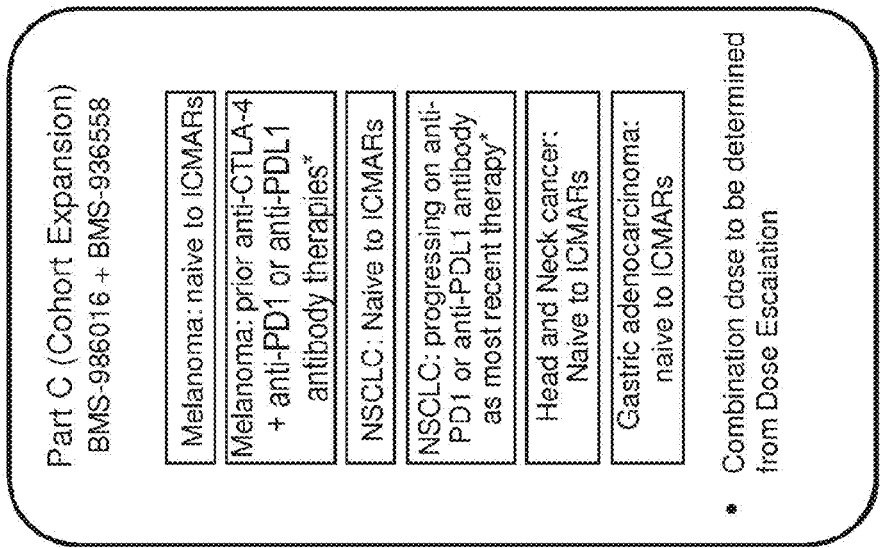
Figure 2B:
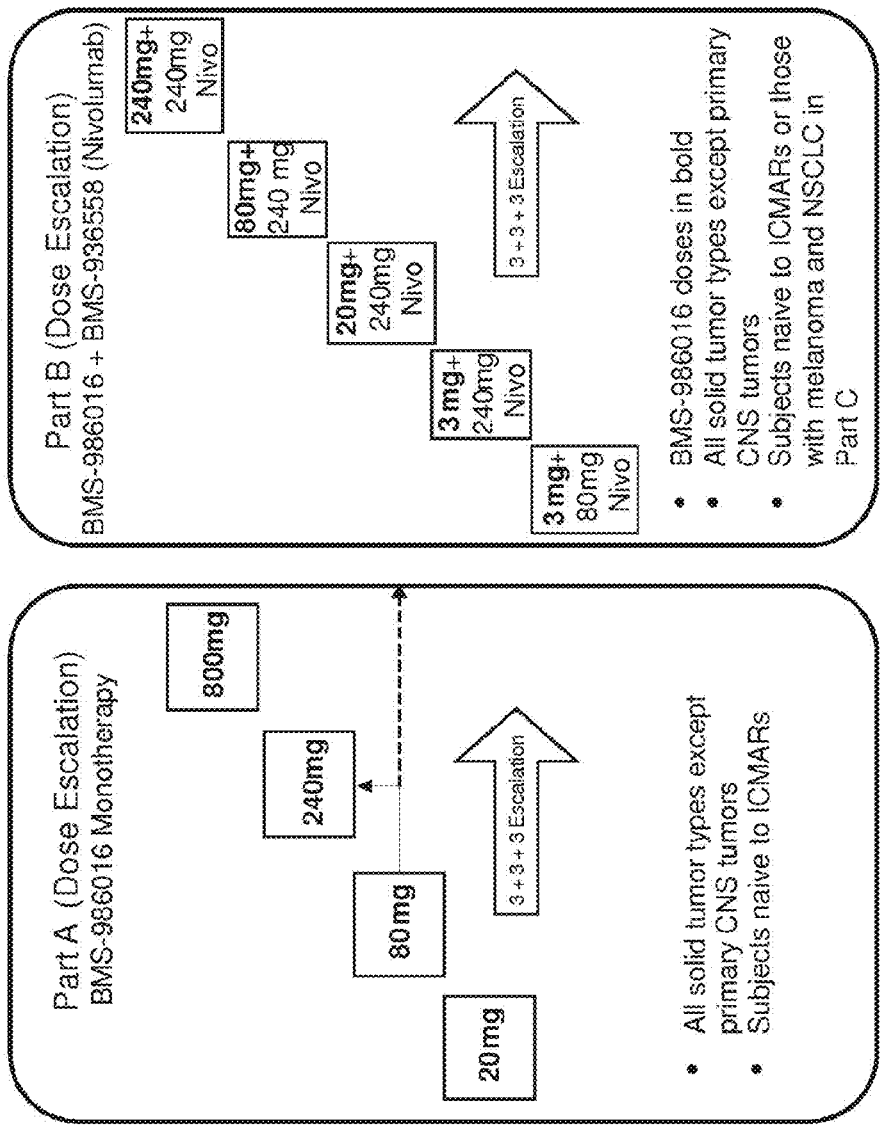

This is a Phase 1, open-label study of BMS-986016 administered as a single agent and in combination with BMS-936558 (nivolumab) to subjects with advanced solid tumors. The study is conducted in 3 parts. Part A and Part B consist of a 3+3+3 dose escalation design with BMS-986016 administered as a single agent (Part A) or in combination with BMS-936558 (Part B) in subjects with advanced solid tumors. Treatment in Part B is initiated upon the decision to escalate to the third dose cohort in Part A (in accordance with dose escalation rules). Subsequently, escalation in the 2 parts proceeds in parallel. At no point does the dose of BMS-986016 administered in combination with BMS-936558 (Part B) exceed doses of BMS-986016 that have been demonstrated previously to be safe on the monotherapy dose escalation arm (Part A). Part C consists of cohort expansion in 6 disease-restricted populations of approximately 16 subjects each, with BMS-986016 administered in combination with BMS-936558. Treatment in Part C is initiated when the maximum tolerated dose (MTD) (or maximum administered dose (MAD) if no MTD is determined) for Part B has been determined. The doses selected for Part C do not exceed the Part B MTD or MAD, but dose determination may incorporate assessment of other data, including toxicities and PK and pharmacodynamic data from Parts A and B. A schematic of the study is provided in FIG. 2.

Subjects complete up to 4 periods of the study as follows: Screening (up to 28 days), Treatment (up to a maximum of twelve 8-week cycles of study therapy), Clinical Follow-up (135 days), and Survival Follow-up (up to 2 years following the first dose of study drug; a longer follow-up period could be considered in selected cases if an efficacy signal is apparent). During this period, diagnostic imaging may be performed every 12 weeks until progression in subjects who discontinue due to CR, and in subjects with PR at the end of Cycle 12.

The Treatment Period consists of up to twelve 8-week treatment cycles. Each treatment cycle is comprised of 4 doses of either BMS-986016 alone (Part A) or in combination with BMS-936558 (Parts B and C), administered on Days 1, 15, 29, and 43 of each treatment cycle. In Parts B and C when both antibodies are administered in combination, nivolumab will be given first followed by BMS-986016 within 30 minutes of completing the infusion of nivolumab. Tumor response is evaluated using RECIST v1.1. Subjects are allowed to continue study therapy until the occurrence of either: (1) confirmed complete response (CR), (2) completion of the maximum number of twelve 8-week cycles, (3) progressive disease (PD), (4) clinical deterioration, and/or (5) meeting other criteria for discontinuation. Treatment beyond progression is allowed in select subjects with initial RECIST v1.1-defined PD who are receiving clinical benefit and tolerating treatment. Subjects who discontinue treatment enter a 135-day Clinical Follow-up period.

Figure 3:
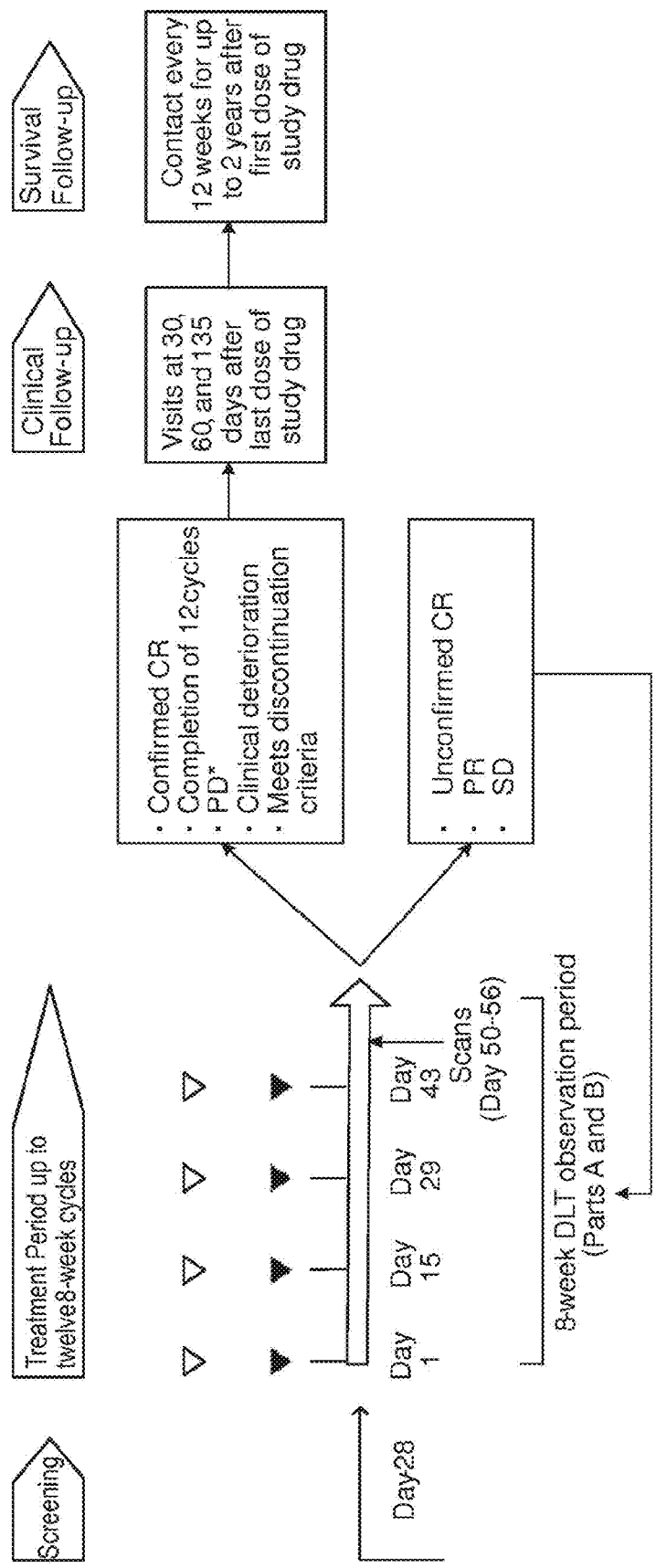
FIG. 3 is a schematic illustrating the Screening, Treatment, Clinical Follow-up, and Survival Follow-up phases of the clinical trial.

After completion of the Clinical Follow-up period, subjects enter the Survival Follow-up period. During this period, clinic visits or telephone contact every 12 weeks are performed to assess survival status. The duration of this period is up to 2 years following the first dose of study drug, although a longer follow-up period is considered in selected cases if an efficacy signal is apparent. Subjects in the Survival Follow-up period who have disease progression are allowed to receive tumor-directed therapy as required. A study schematic is depicted in FIG. 3.

Assessments, including physical examinations, vital sign measurements, 12-lead ECG, and clinical laboratory evaluations are performed at selected times throughout the dosing interval. Subjects are closely monitored for adverse events throughout the study. Blood samples are collected for up to 4 hours following the start of study drug administration for pharmacokinetic analysis.

Subjects are allowed to continue on therapy for up to twelve 8-week cycles or until confirmed complete response, progressive disease, clinical deterioration, or meeting criteria for discontinuation. Subjects may be on study for a total of up to approximately 2.3 years, including a 28-day screening period, up to twelve 8-week cycles of treatment, a 135-day clinical follow-up period, and up to 2 years of follow-up for survival (beginning from the first dose of study drug). The total duration of the study is expected to be approximately 5 years from the time of the first visit of the first subject to the required survival follow-up of the last subject enrolled.

3. Dose Escalation

Part A

In Part A, a 3+3+3 design is used to assess the safety of BMS-986016 given as single agent. A fourth subject may be enrolled at the beginning of a dose escalation cohort, if subject is able to start the first day of dosing within approximately one week of the third subject in the same dose escalation cohort. The dosages during dose escalation are provided in FIGS. 2A and 2B and Table 1 (set forth below). Three subjects (or 4, if applicable) are initially treated in each dose cohort. In Dose Cohort 1, each of the first 3 subjects (or 4, if applicable) is designated as sentinel subjects and begin a treatment at least 5 days apart. Subjects in subsequent cohorts are not required to observe the 5-day interval between treatment start dates. Dose escalation in Part A proceeds as follows:

If 0 of the first 3 subjects (or 4, if applicable) experience a dose-limiting toxicity (DLT) within the DLT evaluation interval, a new cohort of 3 subjects (or 4, if applicable) is treated at the next higher dose level.

If 1 of 3 subjects (or 4, if applicable) experience a DLT within the DLT evaluation interval, that cohort is expanded to 6 subjects.

If 2 of 6 subjects experience a DLT within the DLT evaluation interval, that cohort is expanded to 9 subjects.

If ≥2 of 3 (or 4, if applicable), ≥3 of 6, or ≥3 of 9 subjects experience DLTs within a dose cohort during the DLT evaluation interval, then that dose level is determined to have exceeded the MTD.

TABLE 1

Dose Escalation Schedule for Part A - BMS-986016 Monotherapy

| Dose Cohort Number | Total Subjects | BMS-986016 Dose (IV; mg) |
|---|---|---|
| 1 | n = approximately 3-9 | 20 |
| 2 | n = approximately 3-9 | 80 |
| 3 | n = approximately 3-9 | 240 |
| 4 | n = approximately 3-9 | 800 |
| Total | N = approximately 12-36 | |

Prior to declaring the MTD (or MAD), any cohort previously established to be safe is expanded to obtain additional experience or to investigate dose levels intermediate to those defined in the protocol. Dose escalation rules (cohort size, DLT evaluation interval, cohort expansion criteria, etc.) apply to these expanded or additional cohorts. A maximum of 9 subjects are enrolled in any additional or expanded dose cohorts.

No within-subject dose escalations are permitted. If a dose level is found to exceed the MTD, subjects enrolled in that dose level are treated at a lower dose.

Part B

Treatment in Part B is initiated after the decision is made to escalate to the third dose cohort in Part A (in accordance with dose escalation rules). Subsequently, escalation in the 2 parts proceeds in parallel. At no point does the dose of BMS-986016 administered in combination with BMS-936558 (Part B) exceed doses of BMS-986016 that have been demonstrated previously to be safe on the monotherapy dose escalation arm (Part A). Treatment assignments for subjects eligible for both Part A and Part B alternates between the 2 parts, with consecutively treated subjects assigned to different parts through interactive voice response system (IVRS) whenever possible. If there are no openings available in the part to which the subject is assigned by this algorithm, the subject is assigned to the next open cohort or part. As in Part A, a 3+3+3 design is also be used in Part B to assess the safety of BMS-986016 given in combination with nivolumab. A fourth subject may be enrolled at the beginning of a dose escalation cohort, if subject is able to start the first day of dosing within approximately one week of the third subject in the same dose escalation cohort. The dosages evaluated during dose escalation are provided in FIGS. 2A and 2B and Table B (set forth below). As in Part A, each of the first 3 subjects (or 4, if applicable) in the first dose cohort in Part B will be designated as sentinel subjects and will begin treatment at least 5 days apart.

TABLE 2

Dose Escalation Schedule for Part B - BMS-986016 in Combination with BMS-936558

| Dose Cohort Number | Total Subjects | BMS-986016 Dose (IV; mg) | BMS-936558 Dose (IV; mg) |
|---|---|---|---|
| 1 | n = approximately 3-9 | 3 | 80 |
| 2 | n = approximately 3-9 | 3 | 240 |
| 3 | n = approximately 3-9 | 20 | 240 |
| 4 | n = approximately 3-9 | 80 | 240 |
| 5 | n = approximately 3-9 | 240 | 240 |
| Total | N = approximately 15-45 | | |

Three subjects are treated initially in each dose cohort. In Dose Cohort 1, each of the first 3 subjects, designated as sentinel subjects, begins treatment at least 5 days apart. Subjects in subsequent cohorts are not be required to observe the 5-day interval between treatment start dates.

Dose escalation in Part B proceeds as described for Part A. If the MTD is exceeded in Dose Cohort 2, the subsequent cohort is treated with 20 mg of BMS-986016 and 80 mg of BMS-936558. If this dose combination is found to be safe, escalation proceeds at the previously defined BMS-986016 doses, maintaining the BMS-936558 dose at 80 mg.

If no MTD is reached through Dose Cohort 5, then additional cohorts of BMS-986016 given in combination with BMS-936558 are considered based on the aggregate safety experience during dose escalation.

Prior to declaring the MTD (or MAD), any cohort previously established to be safe is expanded in order to obtain additional experience or to investigate dose levels intermediate to those defined in the protocol. Dose escalation rules (cohort size, DLT evaluation interval, cohort expansion criteria, etc.) apply to these expanded or additional cohorts. A maximum of 9 subjects are enrolled in any additional or expanded dose cohorts.

No within-subject dose escalations are permitted. If a dose level is found to exceed the MTD, subjects enrolled in that dose level are reduced to a lower dose.

4. Cohort Expansion

The purpose of cohort expansion is to gather additional safety, tolerability, preliminary efficacy, pharmacokinetic, and pharmacodynamic information regarding the combination of BMS-986016 and BMS-936558. The doses selected for Part C do not exceed the MTD (or MAD if no MTD is determined) in Part B, but may incorporate assessment of other data including toxicities and PK and pharmacodynamic data from Parts A and B. Doses include doses intermediate to those evaluated in Part B. Modeling is used to help inform the selection of the combination dose level to carry forward in Part C if a dose below the MTD is chosen. Six expansion cohorts are restricted to the tumor types listed below in Tables 3A and 3B. Continuous evaluation of toxicity events in the cohort expansions is performed throughout enrollment in the expansion cohorts. If, at any time, the aggregate rate of treatment-related toxicities meeting DLT criteria exceeds 33% across all subjects treated in the Part C cohort expansion, further enrollment is interrupted. Depending on the nature and grade of the toxicity and after assessing the risk:benefit ratio, a new dose(s) for all cohorts is initiated at a previously tested lower dose level or at a dose level intermediate to previously tested lower dose levels.

Upon determination of the MTD (or MAD if no MTD is determined) in Part A, a BMS-986016 monotherapy cohort is evaluated in cohort expansion. This expansion cohort is restricted to the tumor type(s) found to be responsive to BMS-986016 monotherapy. The dose selected for monotherapy expansion does not exceed the Part A MTD (or MAD if no MTD is determined) and incorporates assessment of other data, including toxicities and PK and pharmacodynamic data from Part A. The dose selected is intermediate to those tested in Part A. Modeling is used to help inform the selection of the dose level to carry forward in Part C if a dose below the MTD is chosen.

TABLE 3A

Tumor Types Eligible For Part C - Cohort Expansion Combination Therapy

| Tumor Type | Total Subjects |
|---|---|
| Melanoma: naive to ICMARs[a] | approximately 16 |
| Melanoma: anti-PD-1 or anti-PD-L1 antibody as most recent therapy[b] | approximately 16 |
| NSCLC[c]: naive to ICMARs[a] | approximately 16 |
| NSCLC[c]: anti-PD-1 or anti-PD-L1 antibody as most recent therapy[b] | approximately 16 |
| HPV[d]-positive head and neck cancer naive to ICMARs[a] | approximately 16 |
| Gastric adenocarcinoma naive to ICMARs[a] | approximately 16 |
| Total | approximately 96 |

[a]ICMARs: immune cell-modulating antibody regimens (such as, but not limited to, ipilimumab, tremelimumab, anti-PD-1, anti-PD-L1, anti-PD-L2, anti-KIR, anti-CD137, and/or anti-OX40 antibodies)
[b]Subjects with anti-PD-1 or anti-PD-L1 antibody as most recent therapy are nonresponsive subjects with progression within 16 weeks of starting therapy. Subjects must provide informed consent within 60 days after the last dose of anti-PD-1 or anti-PD-L1 antibody and should not have discontinued antibody therapy due to serious and/or life-threatening toxicity (e.g., dose-limiting toxicity in prior study). Subjects with anti-PD-1 or anti-PD-L1 antibody as most recent therapy cannot have had prior exposure to any other ICMARs.
[c]NSCLC: non-small cell lung cancer
[d]HPV: human papilloma virus

TABLE 3B

Tumor Types Eligible For Part C - Cohort Expansion Combination Therapy

| Tumor Type | Total Subjects |
|---|---|
| Melanoma: naive to ICMARs[a] | approximately 16 |
| Melanoma: prior anti-CTLA-4 and anti-PD-1 or anti-PD-L1 antibody therapy[f] | approximately 16 |
| NSCLC[g]: naive to ICMARs[a] | approximately 16 |
| NSCLC[c]: anti-PD-1 or anti-PD-L1 antibody as most recent therapy[b] | approximately 16 |
| Head and neck cancer naive to ICMARs[a] | approximately 16 |
| Gastric adenocarcinoma naive to ICMARs[a] | approximately 16 |
| Total | approximately 96 |

[a]ICMARs: immune cell-modulating antibody regimens (such as, but not limited to, anti-CTLA-4, and anti-PD-1 or anti-PD-L1, anti-PD-L2, anti-KIR, anti-CD137, and/or anti-OX40 antibodies)
[b]Melanoma subjects progressing while-on or after receiving anti-CTLA-4 and anti-PD-1 or anti-PD-L1 antibody therapies (in sequential or combination regimens), are eligible. Non-eligible melanoma subjects in this group include those with: 1) last does of anti-CTLA-4 antibody therapy received within 100 days of first dose of study medication; 2) prior exposure to ICMARs other than anti-CTLA-4, anti-PD-1 or anti-PD-L1 antibody therapy regimens; 3)discontinuation from anti-CTLA-4, anti-PD-1 or anti-PD-L1 antibody therapy due to serious and/or life-threatening toxicity (e.g., dose-limiting toxicity in prior exposure).
[c]NSCLC: non-small cell lung cancer
d NSCLC subjects whose disease progresses while-on or after therapy with anti-PD-1 or anti-PD-L1 antibody as most recent therapy. Subject should not have discontinued antibody therapy due to serious and/or life-threatening toxicity (e.g., dose-limiting toxicity in prior study). Subjects with anti-PD-1 or anti-PD-L1 antibody as most recent therapy cannot have had prior exposure to any other ICMARs.

5. Dose Limiting Toxicities

BMS-986016 has the potential to augment the frequency and severity of previously described adverse events associated with BMS-936558, or to produce new toxicities. For the purpose of guiding decisions regarding dose escalation in Part A and Part B, dose-limiting toxicity (DLT) is determined based on the incidence, intensity, and duration of adverse events that are related to study drug and that occur within 56 days (8 weeks) of initiation of study drug (i.e., the DLT evaluation interval, through the completion of Cycle 1). The severity of adverse events is graded according to National Cancer Institute (NCI) Common Terminology Criteria for Adverse Events (CTCAE) v4.0. For the purpose of subject management, DLTs that occur at any time, whether during dose escalation (Part A and Part B) or cohort expansion (Part C) result in all study drug(s) being held, pending evaluation of the event's relatedness to study drug. Subjects must meet criteria for re-treatment prior to re-initiation of study treatment.

Subjects who withdraw from the study during the DLT evaluation interval for reasons other than a DLT may be replaced at the same dose level. In the case that an infusion cannot be administered at a scheduled visit during the DLT evaluation interval, it must be administered as soon as possible. If the delay is between 1 and 7 days, the procedures at the original scheduled visit should be performed and subjects will be considered evaluable for DLT determination. If the delay is more than 7 days, the dose will be considered missed and will not be replaced. For the purpose of making decisions on dose escalation from a safety perspective, subjects will be considered evaluable if they have received 3 out of the 4 scheduled BMS-986016 doses in Part A (or 3 out of 4 schedules BMS-986016 and nivolumab doses in Part B) through the 8 week observation period, only if the one missed dose was secondary to progressive disease or non-medical reasons. Unevaluable subjects may be replaced at the same dose level.

Hepatic, non-hematologic, and hematologic DLTs are defined separately as outlined below.

Hepatic DLT

Any of the following drug-related events are considered a hepatic DLT:

ALT or AST >8×ULN, regardless of duration, or

ALT or AST >5× and ≤8×ULN, that fails to return to Grade 1 within 2 weeks despite medical intervention, or Total bilirubin >5×ULN, or ALT or AST >3×ULN and concurrent total bilirubin >2×ULN Non-Hematologic DLT Any of the following drug-related events are considered a non-hematologic DLT:

Grade 2 immune related-eye pain or reduction in visual acuity that requires systemic treatment, or Grade 2 eye pain or reduction in visual acuity that does not respond to topical therapy and that does not improve to Grade 1 within 2 weeks of initiation of topical therapy, or ≥Grade 3 non-hepatic or non-hematologic toxicity with the exceptions noted below.

The following Grade 3 non-hematologic events are not considered DLTs:

Grade 3 electrolyte abnormality that lasts <72 hours, is not clinically complicated, and resolves spontaneously or responds to conventional medical intervention Grade 3 increase in amylase or lipase that persists for <3 weeks and is not associated with clinical or radiographic evidence of pancreatitis Grade 3 nausea or vomiting that lasts <48 hours, and resolves to Grade 1 either spontaneously or with conventional medical intervention Grade 3 fever that lasts <72 hours, and is not associated with hemodynamic compromise (including hypotension, or clinical or laboratory evidence of end organ perfusion impairment)

Grade 3 endocrinopathy that is well controlled by hormone replacement

Grade 3 tumor flare (defined as pain, irritation, or rash that localizes to sites of known or suspected tumor)

Grade 3 fatigue for less than 7 days

Hematologic DLT

Any of the following drug-related events are considered a hematologic DLT:

Grade 4 febrile neutropenia of any duration

Grade 4 neutropenia that lasts >5 days

Grade 4 thrombocytopenia

Grade 4 anemia

Grade 3 thrombocytopenia associated with clinically significant bleeding

Grade 3 febrile neutropenia that lasts >48 hours

Grade 3 hemolysis

6. Inclusion Criteria

Signed Written Informed Consent

The subject must sign and date the IRB/IEC approved written informed consent form prior to the performance of any study-related procedures that are not considered part of standard of care.

Consent for tumor biopsy samples for Part A or Part B Dose Escalation: Subject must consent to allow the acquisition of existing formalin-fixed paraffin-embedded (FFPE) tumor tissue, either a block or unstained slides, for performance of correlative studies. If an archived sample is not available, subject must consent to allow a pre-treatment tumor biopsy. In either case, study personnel must ensure that the tissue block or slides physically exist prior to initiating therapy. Subjects unable to provide an archived tumor sample and who either do not consent to a pre-treatment tumor biopsy or do not have accessible lesions are not eligible. (However, subjects whose pre-treatment biopsy yields inadequate tissue quantity or quality are not ineligible on this basis alone.)

Consent for tumor biopsy samples for Part C Cohort Expansion: Subjects with melanoma or head and neck tumors: All subjects in the 2 melanoma cohorts and all subjects in the head and neck tumor cohort are required to undergo pre-treatment and on-treatment biopsies; therefore, subjects must have a lesion located such that the specimen can be obtained at acceptable clinical risk as judged by the Investigator. Biopsy sites for any subjects must be distinct from evaluable lesions. Subjects in the melanoma and head and neck cancer cohorts who do not meet these criteria are not eligible; however, subjects whose screening biopsy yields inadequate tissue quantity or quality are not be ineligible on this basis alone. Subjects in the remaining cohorts (NSCLC or gastric adenocarcinoma): Subject must consent to allow the acquisition of existing formalin-fixed paraffin-embedded (FFPE) tumor tissue, either a block or unstained slides, for performance of correlative studies. If an archived sample is not available, subject must consent to allow a pre-treatment tumor biopsy. In either case, study personnel must ensure that the tissue block or slides physically exist prior to initiating therapy. Subjects unable to provide an archived tumor sample and who either do not consent to a pre-treatment tumor biopsy or do not have accessible lesions are not eligible. (However, subjects whose pre-treatment biopsy yields inadequate tissue quantity or quality are not ineligible on this basis alone.) Biopsies cannot be collected in subjects with a single measurable lesion, even if accessible.

Target Population
a) Subjects must have histologic or cytologic confirmation of an incurable solid malignancy that is advanced (metastatic and/or unresectable):
  i) Part A Dose Escalation: BMS-986016 monotherapy
    (1) All solid tumor histologies are permitted except for subjects with primary CNS tumors
    (2) Only subjects without prior exposure to immune cell-modulating antibody regimens (ICMARs) such as, but not limited to, CTLA-4, ipilimumab, tremelimumab, anti-PD-1, anti-PD-L1, anti-PD-L2, anti-KIR, anti-CD137, or anti-OX40 antibodies, are allowed;
    (3) Subjects must have received, and then progressed or been intolerant to, at least one standard treatment regimen in the advanced or metastatic setting, if such a therapy exists.
  ii) Part B Dose Escalation: BMS-986016+BMS-936558
    (1) All solid tumor histologies are permitted except for subjects with primary CNS tumors. Subjects with or without prior anti-PD-1 or anti-PD-L1 antibody therapy are eligible. Alternatively, all solid tumor histologies naive to ICMARs such as, but not limited to, anti-CTLA-4, anti-PD-1, anti-PD-L1, anti-PD-L2, anti-KIR, anti-CD137, or anti-OX40 antibodies, will be permitted except for subjects with primary CNS tumors.
    (2) Subjects without prior anti-PD-1 or anti-PD-L1 antibody therapy cannot have had prior exposure to any other ICMARs such as, but not limited to, ipilimumab, tremelimumab, anti-PD-L2, anti-KIR, anti-CD137, or anti-OX40 antibodies. Alternatively, Subjects without prior anti-PD-1 or anti-PD-L1 antibody therapy cannot have had prior exposure to any other ICMARs such as, but not limited to, ipilimumab, tremelimumab, anti-PD-L2, anti-KIR, anti-CD137, or anti-OX40 antibodies.
    (3) NSCLC subjects whose disease progresses while-on or after therapy with anti-PD-1 or anti-PD-L1 antibody as most recent therapy. Alternatively, subjects with prior anti-PD-1 or anti-PD-L1 antibody as most recent therapy:
      (a) Disease is nonresponsive while on anti-PD-1 or anti-PD-L1 antibody therapy and presents with PD (per RECIST) within 16 weeks of starting therapy.
      (b) Cannot have had therapy discontinued due to serious and/or life-threatening anti-PD-1 or anti-PD-L1 antibody-related toxicity (e.g., dose-limiting toxicity in prior study).
      (c) Must provide informed consent within 60 days after the last dose of anti-PD-1 or anti-PD-L1 antibody therapy.
      (d) Cannot have had prior exposure to ICMARs such as, but not limited to, anti-CTLA-4 antibody therapy, ipilimumab, tremelimumab, anti-PD-L2, anti-KIR, anti-CD137, or anti-OX40 antibodies.
    (4) Melanoma subjects whose disease is progressing while-on or after receiving anti-CTLA-4 and anti-PD-1 or anti-PD-L1 antibody therapies (a) Anti-CTLA-4 and anti-PD-1 or anti-PD-L1 antibody therapies could have been received in sequential or combination regimens (b) Last dose of anti-CTLA-4 antibody therapy must have been received >100 days of first dose of study medication (c) Cannot have had therapy discontinued due to serious and/or life-threatening antibody-related toxicity (e.g., dose-limiting toxicity in prior study) (d) Cannot have had prior exposure to any ICMARs other than anti-CTLA-4 and anti-PD-1 or anti-PD-L1 antibody therapy.
    (5) Subjects must have received, and then progressed or been intolerant to at least one standard treatment regimen.
  iii) Part C Cohort Expansion
    (1) The following groups are enrolled:
      (a) Melanoma—subjects naive to ICMARs
      (b) Melanoma—subjects whose disease is nonresponsive while on anti-PD-1 or anti-PD-L1 antibody therapy as most recent therapy and presents with PD (per RECIST) within 16 weeks of starting therapy. Subject must provide informed consent within 60 days after last dose of anti-PD-1 or anti-PD-L1 antibody therapy and should have not discontinued antibody therapy due to serious and/or life-threatening toxicity (e.g., dose-limiting toxicity in prior study). These subjects cannot have had prior exposure to any other ICMARs such as, but not limited to, ipilimumab, tremelimumab, anti-PD-L2, anti-KIR, anti-CD137, or anti-OX40 antibodies. Alternatively, subjects whose disease is progressing while on or after receiving anti-CTLA-4 and anti-PD-1 or anti-PD-L1 antibody therapy (in sequential or combination regimens), are eligible. Last dose of anti-CTLA-4 antibody therapy must have been received >100 days of first dose of study medication. Subjects should have not discontinued antibody therapy due to serious and/or life-threatening toxicity (e.g., dose-limiting toxicity in prior study). These subjects cannot have had prior exposure to any ICMARs other than anti-CTLA-4 and PD-1 or anti-PD-L1 antibody therapy.
      (c) Non-small cell lung cancer (NSCLC)—subjects naive to ICMARs
      (d) NSCLC—subjects whose disease is nonresponsive while on anti-PD-1 or anti-PD-L1 antibody therapy as most recent therapy and presents with PD (per RECIST) within 16 weeks of starting therapy. Subject must provide informed consent within 60 days after last dose of anti-PD-1 or anti-PD-L1 antibody therapy and should have not discontinued antibody therapy due to serious and/or life-threatening toxicity (e.g., dose-limiting toxicity in prior study). These subjects cannot have had prior exposure to any other ICMARs such as, but not limited to, ipilimumab, tremelimumab, anti-PD-L2, anti-KIR, anti-CD137, or anti-OX40 antibodies. Alternatively, NSCLC subjects whose disease progresses while-on or after therapy with anti-PD-1 or anti-PD-L1 antibody as most recent therapy. Subject should have not discontinued antibody therapy due to serious and/or life-threatening toxicity (e.g., dose-limiting toxicity in prior study). These subjects cannot have had prior exposure to any other ICMARs such as, but not limited to, anti-CTLA-4, anti-PD-L2, anti-KIR, anti-CD137, or anti-OX40 antibodies.
      (e) HPV-associated head and neck tumors—subjects naive to ICMARs and with HPV positivity as defined by p16 immunohistochemistry (IHC)-positive and/or HPV-16 in situ hybridization (ISH)-positive
        (i) Histology restricted to squamous cell carcinoma. Alternatively, subjects with advanced/ metastatic head and neck tumors naïve to ICMARs (i) Histology restricted to squamous cell carcinoma.
(f) Gastric adenocarcinoma subjects naive to ICMARs
  (i) HER2(+) and HER2(−) subjects are allowed
b) Subjects must have received, and then progressed or been intolerant to, at least one standard treatment regimen in the advanced or metastatic setting, if such a therapy exists.
c) Subjects with any prior treatment regimens are eligible. The following are not considered separate lines of treatment: addition of a compound to an ongoing regimen, restarting the same regimen after a drug holiday, or switching from IV to oral therapy.
d) Presence of at least one lesion with measurable disease as defined by RECIST v1.1 criteria for response assessment. Subjects with lesions in a previously irradiated field as the sole site of measurable disease are permitted to enroll provided that the lesion(s) have demonstrated clear progression prior to the time of informed consent and can be measured accurately.
e) ECOG status of 0 or 1.
f) Life expectancy of ≥12 weeks at the time of informed consent.
g) Adequate organ function as defined by the following:
  i) White blood cells (WBCs) ≥2000/μL (stable off any growth factor within 4 weeks of first study drug administration)
  ii) Neutrophils ≥1500/μL (stable off any growth factor within 4 weeks of first study drug administration)
  iii) Platelets ≥100×10³/μL (transfusion to achieve this level is not permitted within 2 weeks of first study drug administration)
  iv) Hemoglobin ≥8.5 g/dL (transfusion to achieve this level is not permitted within 2 weeks of first study drug administration)
  v) Creatinine <1.5×ULN or creatinine clearance ≥40 mL/min (Cockcroft-Gault formula)
  vi) ALT and AST ≤3×ULN
  vii) Lipase and amylase <1.5×ULN
  viii) Total bilirubin ≤1.5×ULN (except subjects with Gilbert's Syndrome who must have normal direct bilirubin)
h) Normal thyroid function, or stable on hormone supplementation
i) Ability to comply with treatment, PK, and pharmacodynamic sample collection and required study follow-up.
j) Subject re-enrollment: This study permits the re-enrollment of a subject that has discontinued the study as a pre-treatment failure (i.e., subject has not been randomized/has not been treated). If re-enrolled, the subject must be re-consented.

Age and Reproductive Status
a) Men and women, ages ≥18 years at the time of informed consent
b) Women of childbearing potential (WOCBP) must use methods of contraception. For a teratogenic study drug and/or when there is insufficient information to assess teratogenicity (preclinical studies have not been done), 2 forms of contraception are required. One method must be highly effective (failure rate of less than 1% when used consistently and correctly) and the second method may also be highly effective. The individual methods of contraception should be determined in consultation with the Investigator. WOCBP must follow instructions for birth control for a total of 24 weeks after the last dose of investigational drug (a period of 30 days plus the time required for the investigational drug to undergo 5 half-lives). Women of childbearing potential (WOCBP) are defined as any female who have experienced menarche and who has not undergone surgical sterilization (hysterectomy or bilateral oophorectomy) and is not postmenopausal. Menopause is defined as 12 months of amenorrhea in a woman over age 45 in the absence of other biological or physiological causes. In addition, females under the age of 55 must have a documented serum follicle-stimulating hormone (FSH) level >40 mIU/mL to confirm menopause. Females treated with hormone replacement therapy, (HRT) are likely to have artificially suppressed FSH levels and may require a washout period in order to obtain a physiologic FSH level. The duration of the washout period is a function of the type of HRT used. The duration of the washout period below are suggested guidelines and the investigators should use their judgement in checking serum FSH levels. If the serum FSH level is >40 mIU/ml at any time during the washout period, the woman can be considered post-menopausal.

1 week minimum for vaginal hormonal products, (rings, creams, gels)

4 week minimum for transdermal products 8 week minimum for oral products

Other parenteral products may require washout periods as long as 6 months.

c) Women must have a negative serum or urine pregnancy test (minimum sensitivity of urine pregnancy test of 25 IU/L of either total human chorionic gonadotropin (hCG) or the beta fraction) within 24 hours prior to the start of investigational product.
d) Women must not be breastfeeding.
e) Men who are sexually active with WOCBP must use methods of contraception. For a teratogenic study drug and/or when there is insufficient information to assess teratogenicity (preclinical studies have not been done), 2 forms of contraception are required. One method must be highly effective (failure rate of less than 1% when used consistently and correctly) and the second method may also be highly effective. Men who are sexually active with WOCBP must follow instructions for birth control for a total of 33 weeks after the last dose of investigational drug (a period of 90 days plus the time required for the investigational drug to undergo 5 half-lives).

Women who are not of childbearing potential (i.e., who are postmenopausal or surgically sterile; and permanently azoospermic men (e.g., bilateral orchiectomy) do not require contraception. Women of childbearing potential (WOCBP) are defined as females who have experienced menarche and who have not undergone surgical sterilization (hysterectomy or bilateraloophorectomy) or are not postmenopausal. Menopause is defined clinically as 6 months of amenorrhea in a woman over age 45 in the absence of other biological or physiological causes. In addition, women under the age of 55 must have a documented serum follicle-stimulating hormone (FSH) level >40 mIU/mL to confirm menopause.

7. Exclusion Criteria

Target Disease Exceptions

Subjects with known or suspected CNS metastases or with the CNS as the only site of active disease are excluded with the following exceptions:
  i) Subjects with controlled brain metastases are allowed to enroll. Controlled brain metastases are defined as those with no radiographic progression for at least 4 weeks after radiation and/or surgical treatment at the time of consent. Subjects must have been off of steroids for at least 2 weeks prior to informed consent, and have no new or progressive neurological signs and symptoms.
  ii) Subjects with signs or symptoms of brain metastases are not eligible unless brain metastases are ruled out by computed tomography (CT) or magnetic resonance imaging (MRI).

Participation in any prior clinical study with BMS-936558, including subjects in comparator arms, in which overall survival is listed as the primary or co-primary endpoint and which has not completed analysis based on the primary endpoint.

Medical History and Concurrent Diseases

Subjects with a prior malignancy are excluded, except adequately treated basal cell or squamous cell skin cancer, localized prostate cancer, carcinoma in situ of the cervix or carcinoma in situ of the bladder, or in situ ductal or lobular carcinoma of the breast. Subjects with other prior malignancies diagnosed more than 2 years previously (at the time of informed consent) who have received therapy with curative intent with no evidence of disease during the interval who are considered to present a low risk for recurrence are eligible.

Subjects with any active autoimmune disease or history of known or suspected autoimmune disease with the exception of subjects with isolated vitiligo, resolved childhood asthma/atopy, controlled hypoadrenalism or hypopituitarism, and euthyroid patients with a history of Grave's disease (subjects with controlled hyperthyroidism must be negative for thyroglobulin and thyroid peroxidase antibodies and thyroid-stimulating immunoglobulin prior to study drug administration).

A known or underlying medical condition that could make the administration of study drug hazardous to the subject or could adversely affect the ability of the subject to comply with or tolerate study.

Requirement for Daily Supplemental Oxygen.

Uncontrolled or significant cardiovascular disease including, but not limited to, any of the following: Myocardial infarction or stroke/transient ischemic attack (TIA) within the 6 months prior to consent, uncontrolled angina within the 3 months prior to consent, any history of clinically significant arrhythmias (such as ventricular tachycardia, ventricular fibrillation, or torsades de pointes), QTc prolongation >480 msec, history of other clinically significant heart disease (i.e., cardiomyopathy, congestive heart failure with New York Heart Association [NYHA] functional classification pericarditis, significant pericardial effusion).

Cardiovascular disease-related requirement for daily supplemental oxygen.

A confirmed history of encephalitis, meningitis, or uncontrolled seizures in the year prior to informed consent.

Positive blood screen for human immunodeficiency virus (HIV) or known acquired immunodeficiency syndrome (AIDS).

History of any chronic hepatitis as evidenced by positive test for hepatitis A antibody (HepA IgM) (Note: history of resolved hepatitis A virus infection is not an exclusion criterion), positive test for hepatitis B surface antigen (HBsAg) and/or hepatitis B core antigen, positive test for qualitative hepatitis C viral load (by PCR).

Evidence of active infection that requires systemic antibacterial, antiviral, or antifungal therapy ≤7 days prior to initiation of study drug therapy.

Any other significant acute or chronic medical illness.

Subjects who are unable to undergo venipuncture and/or tolerate venous access.

Any other sound medical, psychiatric, and/or social reason.

Any of the following procedures or medications:

Within 2 weeks prior to time of informed consent: systemic or topical corticosteroids at immunosuppressive doses 7.5 mg/day of prednisone or equivalent), palliative radiation and gamma knife radiosurgery in CNS, or medicinal herbal preparations.

Within 4 weeks prior to study drug administration: any investigational drug or placebo, any anticancer therapy (chemotherapy, biologics, therapeutic vaccines, radiotherapy, or hormonal treatment), non-oncology vaccines containing live virus, allergen hyposensitization therapy, growth factors, e.g., granulocyte-colony stimulating factor (G-CSF), granulocyte macrophage-colony stimulating factor (GM-CSF), erythropoietin, major surgery, or biphosphonates.

Within 10 weeks prior to study drug administration: receptor activator of nuclear factor kappa-B ligand (RANK-L) inhibitors.

Allergies and Adverse Drug Reaction

History of allergy to anti-PD-1 or anti-PD-L1 antibody therapy or to other monoclonal antibodies or related compounds or to any of their components (e.g., history of severe hypersensitivity reactions to drugs formulated with polysorbate 80).

Other Exclusion Criteria

Prisoners or subjects who are involuntarily incarcerated.

Subjects who are compulsorily detained for treatment of either a psychiatric or physical (e.g., infectious disease) illness.

Inability to comply with restrictions and prohibited activities and treatments.

8. Guidelines for Dose Modification

Intrasubject dose escalation of BMS-986016 or BMS-936558 is not permitted in this study. With the possible exception of subjects being treated at a dose level that is subsequently deemed to exceed the MTD, intrasubject dose reduction of BMS-986016 or BMS-936558 is not permitted.

In some cases, the natural history of select adverse events associated with immunotherapy can differ from and be more severe than adverse events caused by other therapeutic classes. Early recognition and management mitigates severe toxicity.

Additionally, management algorithms can assist with select toxicities. Toxicities for which management algorithms have been developed include:
  Pulmonary
  Gastrointestinal
  Hepatic
  Endocrine
  Renal
  Dermatologic
  Neurologic Subjects who experience the following must have all study drug(s) held:

DLTs (per definition, are related to study drug)
Select drug-related adverse events and drug-related laboratory abnormalities:
≥Grade 1 pneumonitis
≥Grade 2 abnormality in AST, ALT, total bilirubin, amylase, or lipase
≥Grade 2 creatinine
≥Grade 2 diarrhea or colitis
≥Grade 2 neurological adverse event
Adverse event, laboratory abnormality, or concurrent illness that, in the judgment of the Investigator, warrants delaying the dose of study drug.
Dose delays >7 days are considered missed and is not be replaced.

9. Safety Assessments

Adverse events are assessed continuously during the study and for 135 days after the last treatment. Adverse events are evaluated according to the NCI CTCAE version 4.0. Adverse events are coded using the most current version of Medical Dictionary for Regulatory Activities (MedDRA) and reviewed for potential significance and importance.

10. Other Analyses

Various serologic tumor markers, gene mutation status, and additional analyses are required dependent upon the subject's tumor type as listed below in Table 4. With the exception of the serologic tumor markers, the assessments are not performed if the lab results from previous testing are available.

Additional measures, including non-study-required laboratory tests, are performed as clinically indicated. Results of all laboratory tests required by this protocol are recorded.

11. Efficacy Assessments

Efficacy is evaluated in Parts A and B (dose escalation), as well as in Part C (cohort expansion). Changes in tumor measurements and tumor response at the time of each assessment are determined. The baseline assessment during the screening period requires CT or MRI scans of the chest, abdomen, and pelvis, and other anatomic regions as indicated by individual subject's tumor type and/or disease history. Subsequent timepoints require scans of the chest, abdomen, and pelvis, as well as other anatomic regions that were scanned at baseline based on the individual subject's tumor type and/or disease history. Scans of the brain are otherwise required as clinically indicated.

Analysis of response endpoints are performed according to immune-related response criteria, irRECIST that reflect the clinical experience with other T cell-directed immunotherapies in which objective and durable responses were observed in subjects following progression and without intervening alternative anticancer therapy (Wolchok J D, et al., *Clin. Can. Res.* 2009; 15(23):7412-7420). Individual subject's best overall response (BOR), duration of progression-free survival (PFS), and duration of response (DOR) is calculated as appropriate.

Tumor status are assessed at baseline, during treatment (every 8 weeks) for up to twelve 8-week cycles of therapy,

TABLE 4

Biomarkers by Tumor Type

| Tumor Type | Study Part | Matrix | Lab Test | Assessment | Timepoint |
|---|---|---|---|---|---|
| Colorectal | Parts A, B ONLY | Blood | Serologic Tumor Marker | CEA[a] | Multiple |
|  | Parts A, B ONLY | Tumor Tissue | Gene Mutation Status | EGFR[b] K-RAS MSI[c] | Screening |
| Gastric | Parts A, B, C | Blood | Serologic Tumor Marker | CEA[a] | Multiple |
|  | Parts A, B, C | Tumor Tissue | Gene Mutation Status | HER-2[d] | Screening |
|  | Parts A, B, C | Tumor Tissue | Real Time qPCR[e] | EBV[f] | Screening |
| Germ Cell | Parts A, B ONLY | Blood | Serologic Tumor Marker | βhCG[g] AFP[h] | Multiple |
| Head and Neck | Part C ONLY | Tumor Tissue | IHC and/or ISH[i] | HPV[j] | Screening (Eligibility) |
| Melanoma | Parts A, B, C | Tumor Tissue | Gene Mutation Status | BRAF | Screening |
| NSCLC | Parts A, B, C | Tumor Tissue | Gene Mutation Status | ALK[k] K-RAS EGFR[b] | Screening |
| Ovarian | Parts A, B ONLY | Blood | Serologic Tumor Marker | CA125[l] | Multiple |
| Prostate | Parts A, B ONLY | Blood | Serologic Tumor Marker | PSA[m] | Multiple |

[a] CEA: carcinoembryonic antigen
[b] EGFR: epidermal growth factor receptor
[c] MSI: microsatellite instability
[d] HER-2: human epidermal growth factor receptor 2 status via IHC and/or ISH
[e] Real time qPCR: real time quantitative polymerase chain reaction for BamH1-A Reading Frame-1(BARF1) gene
[f] EBV: Epstein-Barr virus
[g] βhCG: beta-human chorionic gonadotrophin
[h] AFP: alpha-fetoprotein
[i] IHC and/or ISH: p16 immunohistochemistry (IHC) and/or HPV-16 in situ hybridization (ISH)
[j] HPV: human papilloma virus
[k] ALK: anaplastic lymphoma kinase
[l] CA125: cancer antigen 125
[m] PSA: prostate specific antigen and once during follow-up. CT and MRI scans re read and assessed locally per RECIST v1.1. All imaging scans are de-identified and archived in their native Digital Imaging and Communications in Medicine (DICOM) format as part of the subject's study file.

The efficacy assessments include the ORR (e.g., PR+CR), DOR, and PFSR at landmark timepoints (e.g., 24 weeks), based on assessment of tumor response using irRECIST and RECIST v1.1. Landmark 2-year overall survival (OS).

12. Pharmacokinetic Assessments

Serum samples for BMS-986016 pharmacokinetics and anti-drug antibody (ADA) assessments are collected for all subjects. Serum samples for BMS-936558 pharmacokinetics and ADA assessments re collected for all subjects enrolled in Part B and C. The serum samples are analyzed for BMS-986016 and BMS-936558 by a validated immunoassay. In addition, selected serum samples are analyzed by an exploratory orthogonal method (e.g., liquid chromatography [LC]-mass spectrometry [MS]/MS) that measures total BMS-986016 and/or BMS-936558.

13. Exploratory Biomarker Assessment

The pharmacodynamics of BMS-986016 treatment administered alone or in combination with BMS-936558 is assessed by quantifying biomarkers in peripheral blood and tumor tissue in the first 3 subjects enrolled at each dose level during the dose escalation (Parts A and B) and in subjects with melanoma and head and neck cancers during cohort expansion (Part C) phases of the study. Detailed schedules of pharmacodynamic evaluations are provided below in Tables 5-6. Details regarding the tumor tissues requirements for subjects in Parts A, B, and C of the study are provided below in Table 7.

TABLE 5A

Part A & B (Dose Escalation) - Biomarker Sampling Schedule
(ONLY for First 3 Subjects in each Dose Level)

| Collection Timing Study Day | Serum Soluble Biomarkers (Serum Biomarkers) | PBMC | | | Tumor Archival Tissue[a] | Whole Blood | |
| --- | --- | --- | --- | --- | --- | --- | --- |
| | | Immuno-phenotyping/ Tetramer (Flow Cytometry/ PBMC) | Ex vivo Functional Assay (Cellular Assay) | | | Gene Expression (Whole Blood mRNA) | SNP |
| Screening | | | | | X | | |
| Cycle 1 | | | | | | | |
| Day 1 | X | X | X | | | X | X |
| Day 5[a] | X | | | | | | |
| Day 8 | X | X | | | | | |
| Day 15 | X | X | | | | X | |
| Day 29 | X | X | | | | X | |
| Day 43 | X | X | X | | | X | |
| Cycle 2 | | | | | | | |
| Day 29 | X | X | X | | | X | |
| Upon Progression | | | | | | | |
| Upon Progression[b] | X | X | X | | X | X | |

[a]Day 5 visit can occur on Day 3 or Day 4
[b]Optional; collected upon confirmation of PD
NOTE:
All samples are drawn pre-dose

TABLE 5B

Part A & B (Dose Escalation) - Biomarker Sampling Schedule
(ONLY for First 3 Subjects in each Dose Level)

| Collection Timing Study Day | Serum Soluble Biomarkers (Serum Biomarkers) | PBMC | | | Tumor Archival Tissue | Whole Blood | |
| --- | --- | --- | --- | --- | --- | --- | --- |
| | | Immuno-phenotyping/ Tetramer (Flow Cytometry/ PBMC) | Ex vivo Functional Assay (Cellular Assay) | | | Gene Expression (Whole Blood mRNA) | SNP |
| Screening | | | | | X | | |
| Cycle 1 | | | | | | | |
| Day 1 | X | X | X | | | X | X |
| Day 5[b] | X | | | | | | |
| Day 8 | X | X | | | | | |

TABLE 5B-continued

Part A & B (Dose Escalation) - Biomarker Sampling Schedule
(ONLY for First 3 Subjects in each Dose Level)

| Collection Timing Study Day | Serum Soluble Biomarkers (Serum Biomarkers) | PBMC Immuno-phenotyping/ Tetramer (Flow Cytometry/ PBMC) | PBMC Ex vivo Functional Assay (Cellular Assay) | Tumor Archival Tissue | Whole Blood Gene Expression (Whole Blood mRNA) | SNP |
|---|---|---|---|---|---|---|
| Day 15 | X | X | | | X | |
| Day 29 | X | X | | | X | |
| Day 43 | X | X | X | | X | |
| Cycle 2 | | | | | | |
| Day 29 | X | X | X | | X | |
| Upon Progression | | | | | | |
| Upon Progression[b] | X | X | X | X | X | |
| Upon Drug-related AE | | | | | | |
| Upon occurrence of ≥ Grade 2 drug related pneumonitis or neurological AE | X | X | X | | | | a Day 5 visit can occur on Day 3 or Day 4. Day 8 visit can occur on Day 7 or Day 9.
[b]Optional; collected upon confirmation of PD
NOTE:
All samples are drawn pre-dose

TABLE 6A

Part C (Cohort Expansion) - Biomarker Sampling Schedule (ONLY for Subjects with Melanoma and Head and Neck Cancer)

| Collection Timing Study Day | Serum Soluble Biomarkers (Serum Biomarkers) | PBMC Immuno-phenotyping/ Tetramer (Flow Cytometry/ PBMC) | PBMC Ex vivo Functional Assay (Cellular Assay) | Tumor "Fresh" Tumor Biopsy | Whole Blood Gene Expression (Whole Blood mRNA) | SNP |
|---|---|---|---|---|---|---|
| Screening | | | | X[a] | | |
| Cycle 1 | | | | | | |
| Day 1 | X[b] | X | X | | X | X |
| Day 5[c] | X | | | | | |
| Day 8 | X | X | | | | |
| Day 15 | X | X | | | X | |
| Day 29 | X | X | | | X | |
| Day 43 | X | X | X | | X | |
| Day 50-56 | | | | X[d] | | |
| Cycle 2 | | | | | | |
| Day 29 | X | X | X | | X | |
| Upon Progression | | | | | | |
| Upon Progression[e] | X | X | X | X | X | |

NOTE:
All samples are drawn pre-dose
[a]Fresh tumor biopsy is mandatory for subjects with melanoma and head and neck cancer in Part C.
[b]Serum and plasma at Cycle 1 Day 1. Serum only at all other timepoints.
[c]Day 5 visit can occur on Day 3 or Day 4
[d]Fresh tumor biopsy is mandatory for subjects with melanoma and head and neck cancer in Part C. Biopsy is obtained at anytime during Cycle 1, Week 8 (Days 50-56) at the same time as diagnostic imaging.
[e]Optional; collected upon confirmation of PD

TABLE 6B

Part C (Cohort Expansion) - Biomarker Sampling Schedule (ONLY for Subjects with Melanoma and Head and Neck Cancer)

| Collection Timing Study Day | Serum Soluble Biomarkers | Plasma (Serum Biomarkers) | Immuno-phenotyping/ Tetramer (Flow Cytometry/ PBMC) | Ex vivo Functional Assay (Cellular Assay) | Tumor "Fresh" Tumor Biopsy | Gene Expression (Whole Blood mRNA) | SNP |
|---|---|---|---|---|---|---|---|
| Screening | | | | | X[a] | | |
| Cycle 1 | | | | | | | |
| Day 1 | X | X | X | X | | X | X |
| Day 5[c] | X | | | | | | |
| Day 8[c] | X | | X | | | | |
| Day 15 | X | | X | | | X | |
| Day 29 | X | X | X | | | X | |
| Day 36 | X | | X | | | X | |
| Day 43 | X | X | X | X | | X | |
| Day 50-56 | | | | | X[d] | | |
| Cycle 2 | | | | | | | |
| Day 29 | X | | X | X | | X | |
| Upon Progression | | | | | | | |
| Upon Progression[e] | X | | X | X | X | X | |
| Upon Drug-related AE | | | | | | | |
| Upon occurrence of ≥ Grade 2 drug related pneumonitis o neurological AE | X | | X | X | | | |

[a] Fresh tumor biopsy is mandatory for subjects with melanoma and head and neck cancer Part C.
[b] PBMC samples only to be collected for subjects in the US, not required for subjects Ex-US.
[c] Day 5 visit can occur on Day 3 or Day 4. Day 8 visit can occur on Day 7 or Day 9.
[d] Fresh tumor biopsy is mandatory for subjects with melanoma and head and neck cancer in Part C. Biopsy can be obtained at anytime during Cycle 1, Week 8 (Days 50-56) at same time as diagnostic imaging.
e Optional; to be collected upon confirmation of PD.

TABLE 7

Tumor Tissue Requirements for Parts A, B, and C

| Study Part | Part A and B (Dose Escalation) | Part C (Cohort Expansion) | |
|---|---|---|---|
| Subjects | ALL subjects in Part A or B | Subjects with melanoma or head and neck tumors ONLY | Subjects with NSCLC or gastric adenocarcinoma ONLY |
| Type of Specimen | Archived tumor tissue. If archived sample is not available, must obtain a "fresh" pre-treatment tumor biopsy | Mandatory "fresh" biopsies (pre- and on-treatment) | Archived tumor tissue. If archived sample is not available, must obtain a "fresh" pre-treatment tumor biopsy |
| Upon Progression | Optional "fresh" biopsy upon confirmation of PD | Optional "fresh" biopsy upon confirmation of PD | Optional "fresh" biopsy upon confirmation of PD |

Soluble Biomarkers (Serum Biomarkers)—Parts A, B, and C

Pre-treatment and on-treatment serum levels of chemokines, cytokines, and tumor-associated soluble proteins is assessed by techniques that include, but are not limited to, ELISA or multiplex assays. Analytes include markers of inflammation, immune activation, host tumor growth factors, and tumor-derived proteins.

Antitumor Antibodies (Serum Biomarkers)—Parts A, B, and C

Treatment with BMS-986016 and BMS-936558 may result in the generation of novel, or an increase in existing, antibodies to tumor-associated antigens. An assessment of antibodies to a panel of >8000 proteins is performed using pre-treatment and on-treatment serum in multiplex and ELISAs. These data are used to explore if antitumor antibodies are associated with clinical response and safety parameters, as well as inform pharmacodynamics of drug administration.

Immunophenotyping (Flow Cytometry/PBMC)—Parts A, B, and C

Peripheral blood mononuclear cells (PBMCs) are used to characterize and quantify the activation and regulatory status of myeloid and lymphoid cells by polychromatic flow cytometry. Subsets of cells characterized by immunophenotyping include naive, activated, and exhausted effector and memory T cell populations, regulatory T cells, and myeloid-derived suppressor cells.

Ex vivo Functional Assays (Cellular Assay)—Parts A, B, and C

To assess whether BMS-986016 and BMS-936558 restores T cell activation and function, PBMCs are isolated and cryopreserved. The functional status of effector T cells, including, but not limited to, IFN-γ and granzyme B, is assessed by flow cytometric staining.

Peripheral Blood Gene Expression (Whole Blood mRNA) and Tumor Gene Expression—Parts A, B, and C The expression level of genes related to response to BMS-986016±BMS-936558 is quantified by microarray and/or quantitative reverse transcription polymerase chain reaction (RT-PCR) analysis in whole blood and tumor samples. Analysis includes, but is not necessarily be limited to, genes encoding BMS-986016-stimulated effector functions (perforin, granzyme B, and IFN-γ) and genes encoding T cell co-stimulatory receptors (PD-1, PD-L1, and CTLA-4).

Circulating Tumor DNA Analysis (Serum (plasma) Biomarkers)—Part C

The presence of cell-free DNA in circulating blood is a well-documented phenomenon. Fragments of DNA are shed into the blood stream from dividing cells during cell proliferation or cell death. In patients with cancer, a fraction of this DNA is tumor-derived and is termed circulating tumor DNA (ctDNA). Albeit small, fragments of DNA average between 180 to 200 bp and specific genomic regions can be amplified with PCR. Moreover, several studies have detected mutations in ctDNA that exactly correspond to mutations from the parent tumor. Using tissue and plasma from patients with known driver mutations in melanoma or head and neck cancer, BEAMing technology is utilized to count the frequency of mutations in circulation.

Single Nucleotide Polymorphism Analysis (SNP)—Parts A, B, and C

In order to identify potential polymorphisms associated with the safety and efficacy of BMS-986016 selected genes are evaluated for single nucleotide polymorphisms (SNPs). Genes of interest include, but are not limited to, PD-1, PD-L1, MHC class II, LAG-3, and CTLA-4.

Tumor Biopsy Analysis—Parts A and B

Tumor tissue is collected from all subjects in the dose escalation portion of the protocol. Immunohistochemistry is used to assess the number and composition of immune infiltrates to define the immune cell subsets present within FFPE tumor tissue before and potentially after exposure to BMS-986016 and BMS-936558. These IHC analyses include, but are not necessarily be limited to, the following markers: CD4, CD8, LAG-3, MHC II, PD-1, PD-L1, and PD-L2. Correlations between gene expression and IHC expression are made between assays performed if deemed to be informative.

Tumor-Based Biomarker Measures—Part C

Paired pre- and on-treatment tumor biopsies are mandatory for all subjects with melanoma or head and neck cancer who are enrolled in Part C (cohort expansion). Subjects for whom adequate paired pre- and on-treatment biopsies are not collected may be replaced.

Subjects have at least one lesion large enough to undergo repeated biopsies (pre- and on-treatment biopsies) via core needle (minimum size 18 gauge) or have at least 2 distinct lesions eligible for core needle or excisional biopsies. The expected core needle length should be greater than 5 mm. A punch biopsy is acceptable for cutaneous lesions. Fine needle aspirate biopsies are not accepted. At least two core biopsies are taken at each timepoint, but collection of additional cores is strongly encouraged if deemed clinically safe by the investigator. An assessment of biopsy quality by a pathologist is strongly encouraged at the time of the procedure. All biopsies collected must have a detailed pathology report submitted with the specimen.

Tumor biopsy specimens are obtained from consenting subjects prior to and during treatment with BMS-986016 and BMS-936558 to characterize immune cell populations and expression of selected tumor markers. Biopsy samples are used for the following assessments:

Characterization of TILs and tumor antigens. Immunohistochemistry is used to assess the number and composition of immune infiltrates to define the immune cell subsets present within FFPE tumor tissue before and after exposure to BMS-986016 and nivolumab. These IHC analyses include, but are not necessarily limited to, the following markers: CD4, CD8, LAG-3, MHC II, PD-1, PD-L1, and PD-L2. Correlations between gene expression and IHC expression are made between assays performed if deemed to be informative.

Laser capture microdissection. Isolation of tumor and/or TIL on FFPE sections is performed by laser capture microdissection (LCM) for high-throughput profiling of molecular events within the tumor microenvironment.

Characterization of T cell repertoire. DNA sequencing is performed on pre- and post-treatment FFPE tumor tissue to assess the composition of the T cell repertoire. Low T cell receptor diversity may be a poor prognostic factor of overall survival in metastatic breast cancer patients. Currently, there is a poor understanding of T cell receptor diversity as a predictor factor of response to immunotherapy, given that the major mechanism of BMS-936558 and BMS-986016 is hypothesized to be the functional restoration of T cell antitumor immunity. Therefore, a characterization of the diversity of the T cell compartment in the periphery, and within the tumor, at baseline and on-treatment is performed by T cell receptor next-generation DNA sequencing. T cell repertoire analysis is also performed from DNA isolated from peripheral blood to compare the status of tumor and peripheral T cell repertoire pre and post treatment.

Gene expression profiling. Tumor biopsies that are collected in RNAlater or similar reagent are examined for mRNA gene expression by Affymetrix gene array technology and/or quantitative real-time polymerase chain reaction (qPCR) to detect expression of selected immune-related genes.

In situ cytokine and negative regulator expression. Tumors biopsies are quantitatively evaluated for RNA, including CD3, IFN-γ, LAG-3, and PD-1.

Subjects whose screening biopsy yields inadequate tissue quantity or quality are allowed to continue in the study. If on-treatment biopsy is not successful, subjects also continue on study. Such subjects are replaced in order to obtain 48 subjects with adequate paired tumor biopsies. If subjects have a response to treatment, on-treatment biopsies might not be possible. In this case, subjects also continue on study.

The tumor tissue that is obtained from these biopsies is divided equally into FFPE and frozen samples, which can be used for histologic confirmation of melanoma, as well as for the assays listed above.

Biopsies are done with local anesthesia or conscious sedation. Institutional guidelines for the safe performance of biopsies are followed. Excisional biopsies are performed to obtain tumor biopsy samples. Invasive procedures that require general anesthesia are not performed to obtain a biopsy specimen. However, if a surgical procedure is performed for a clinical indication, excess tumor tissue is used for research purposes with the consent of the subject.

14. Immunogenicity Assessments

Serum samples collected at timepoints are analyzed by a validated immunogenicity assay. Selected serum samples are analyzed by an exploratory orthogonal method that measures anti-BMS-986016 or anti-BMS-936558. Potential results generated from any orthogonal method are intended as informational for technology exploration purposes and re not reported.

In addition, ad hoc serum samples designated for pharmacokinetic or biomarker assessments are used for immunogenicity analysis if required (e.g., insufficient volume for complete immunogenicity assessment or to follow up on suspected immunogenicity related adverse event).

15. Adverse Events

An adverse event (AE) is defined as any new untoward medical occurrence or worsening of a preexisting medical condition in a clinical investigation subject administered an investigational (medicinal) product and that does not necessarily have a causal relationship with this treatment. An AE is therefore any unfavorable and unintended sign (such as an abnormal laboratory finding), symptom, or disease temporally associated with the use of investigational product, whether or not considered related to the investigational product.

The causal relationship to study drug is determined by a physician and used to assess all adverse events (AE). The casual relationship can be one of the following:

Related: There is a reasonable causal relationship between study drug administration and the AE.

Not related: There is not a reasonable causal relationship between study drug administration and the AE.

The term "reasonable causal relationship" means there is evidence to suggest a causal relationship.

Serious Adverse Events

A serious adverse event (SAE) is any untoward medical occurrence that at any dose:

results in death is life-threatening (defined as an event in which the subject was at risk of death at the time of the event; it does not refer to an event which hypothetically might have caused death if it were more severe)

requires inpatient hospitalization or causes prolongation of existing hospitalization results in persistent or significant disability/incapacity is a congenital anomaly/birth defect is an important medical event (defined as a medical event(s) that may not be immediately life-threatening or result in death or hospitalization but, based upon appropriate medical and scientific judgment, may jeopardize the subject or may require intervention (e.g., medical, surgical) to prevent one of the other serious outcomes listed in the definition above). Examples of such events include, but are not limited to, intensive treatment in an emergency room or at home for allergic bronchospasm; blood dyscrasias or convulsions that do not result in hospitalization.) Potential drug induced liver injury (DILI) is also considered an important medical event.

Suspected transmission of an infectious agent (e.g., pathogenic or nonpathogenic) via the study drug is an SAE. Although pregnancy, overdose, cancer, and potential drug induced liver injury (DILI) are not always serious by regulatory definition, these events must be handled as SAEs. Any component of a study endpoint that is considered related to study therapy (e.g., death is an endpoint, if death occurred due to anaphylaxis, anaphylaxis must be reported) is reported as SAE.

The following hospitalizations are not considered SAEs:

a visit to the emergency room or other hospital department <24 hours, that does not result in admission (unless considered an important medical or life-threatening event)

elective surgery, planned prior to signing consent admissions as per protocol for a planned medical/surgical procedure routine health assessment requiring admission for baseline/trending of health status (e.g., routine colonoscopy)

medical/surgical admission other than to remedy ill health and planned prior to entry into the study. Appropriate documentation is required in these cases admission encountered for another life circumstance that carries no bearing on health status and requires no medical/surgical intervention (e.g., lack of housing, economic inadequacy, caregiver respite, family circumstances, administrative reason).

Following the subject's written consent to participate in the study, all SAEs, whether related or not related to study drug, are collected, including those thought to be associated with protocol-specified procedures. All SAEs are collected that occur during the screening period and within 135 days of discontinuation of dosing. If applicable, SAEs are collected that relate to any later protocol-specified procedure (e.g., a follow-up skin biopsy). All SAEs are followed to resolution or stabilization.

Nonserious Adverse Events

A nonserious adverse event is an AE not classified as serious. The collection of nonserious AE information begins at initiation of study drug and continues for 135 days after discontinuation of dosing. Nonserious AEs are followed to resolution or stabilization, or reported as SAEs if they become serious. Follow-up is also required for nonserious AEs that cause interruption or discontinuation of study drug and for those present at the end of study treatment as appropriate. All identified nonserious AEs are recorded and described on the nonserious AE page of the CRF (paper or electronic).

Completion of supplemental CRFs are requested for AEs and/or laboratory abnormalities that are reported/identified during the course of the study.

16. Statistical Considerations

Sample Size Determination

Dose Escalation (Parts A and B): Sample size at each dose depends on observed toxicity and cannot be precisely determined. Part A and Part B have 3 to 9 subjects in each cohort.

Cohort Expansion (Part C): Cohort expansion allows for better estimation of the toxicity rate and provide better precision around preliminary estimates of efficacy. If ≤5 of 16 subjects (i.e., ~30% of in a cohort) experience a toxicity, there is at least 90% confidence that the true toxicity rate is not greater than 50.4% (based on Clopper-Pearson exact binomial 1-sided 90% confidence interval). A sample size of 16 subjects per cohort also allows for estimation of the proportion of subjects with objective response (i.e., CR+PR) within a cohort such that the maximum distance between the estimated rate and either limit of the exact 2-sided 95% Clopper-Pearson confidence interval is 27.4%.

Populations for Analyses

All Enrolled Subjects Analysis Set: This analysis set contains all subjects (including screen failures) who signed an informed consent for the study.

All Treated Subjects-Analysis set: This analysis set includes all subjects who receive either drug.

Response-Evaluable Subjects: This analysis set includes all subjects who receive either study drug, have a baseline tumor assessment with measurable disease, and one of the following: (1) at least one evaluable on-treatment tumor assessment, (2) clinical progression, or (3) death prior to the first on-treatment tumor evaluation.

BMS-986016 Pharmacokinetic Analysis Set: This analysis set includes all subjects who receive BMS-986016 and have at least one valid PK parameter to be included in statistical analyses of BMS-986016 PK data.

BMS-986016 Immunogenicity Analysis Set: This analysis set includes all subjects who receive BMS-986016 and have at least one BMS-986016 immunogenicity sample available.

BMS-936558 Immunogenicity Analysis Set: This analysis set includes all subjects who receive BMS-936558 and have at least one BMS-936558 immunogenicity sample available.

Pharmacodynamic Analysis Set: This analysis set includes all treated subjects for whom pharmacodynamic measurements are available at baseline and at least one other timepoint.

Endpoints

The primary endpoint of this Phase 1 study is safety as measured by the rate of AEs, serious adverse events (SAEs), deaths, and laboratory abnormalities (e.g., Grade 3 or higher per CTCAE v 4), assessed during treatment and for up to 135 days of follow-up. All subjects who receive at least one dose of BMS-986016 or BMS-936558 are analyzed for safety.

The PK of BMS-986016 administered both alone and in combination with BMS-936558 is assessed as a secondary objective using the following endpoints derived from serum concentration versus time data in Cycle 1 and Cycle 3:

Cmax Maximum observed serum concentration

Tmax Time of maximum observed serum concentration

Ctrough Trough observed serum concentration

Ctau Concentration at the end of a dosing interval (e.g., concentration at 336 hours)

Css,avg Average concentration over a dosing interval ([AUC(TAU)/tau]

AUC(TAU) Area under the concentration-time curve in one dosing interval

CLT Total body clearance

Vss Volume of distribution at steady state

T-HALFeff AUC Effective elimination half-life that explains the degree of AUC accumulation observed T-HALFeff Cmax Effective elimination half-life that explains the degree of Cmax accumulation observed AI_AUC Accumulation index; ration of AUC(TAU) at steady state to AUC(TAU) after the first dose AI_Cmax Cmax accumulation index; ratio of Cmax at steady state to Cmax after the first dose AI_Ctau Ctau accumulation index; ratio of Ctau at steady state to Ctau after the first dose DF Degree of fluctuation or fluctuation index ([Cmax−Ctau]/Css,avg)

Individual subject PK parameter values are derived by noncompartmental methods by a validated PK analysis program. Actual times are used for the analyses.

Efficacy

Efficacy is assessed as a secondary objective using the endpoints described below for irRECIST and RECIST v1.1. For the purposes of patient management, clinical decision making is based on RECIST. Statistical analysis and reporting are based on both criteria.

Best overall response (BOR) is the best response designation recorded from the start of the study treatment until the last protocol specified tumor assessment (e.g., 30 day follow-up visit) taking into account any requirement for confirmation, based on RECIST v1.1 or irRECIST criteria. CR or PR determinations included in the BOR assessment are confirmed by a consecutive second (confirmatory) evaluation meeting the criteria for response and performed at least 4 weeks after the criteria for response are first met.

Objective response rate (ORR) is defined as the total number of subjects whose BOR is either CR or PR divided by the total number of subjects in the population of interest.

Duration of response (DOR) computed only for subjects with a BOR of CR or PR is defined as the number of days between the date of first response and the subsequent date of objectively documented disease progression based on the criteria (RECIST v1.1 or irRECIST) or death, whichever occurs first. For those subjects who remain alive and have not progressed or received subsequent therapy, duration of response is censored on the date of last protocol specified tumor assessment. Subjects who receive subsequent therapy are censored at the start of subsequent therapy.

Progression free survival (PFS) is defined as the probability of a subject remaining progression-free and surviving. The probability is computed based on the number of days between the first dose of study drug and progressive disease (as defined by RECIST or irRECIST) or death. For those subjects who remain alive and have not progressed, PFS is censored on the date of the last protocol specified tumor assessment.

These endpoints are determined based on tumor measurements occurring every 8 weffeks during the Treatment Period (up to twelve 8-week cycles), and once during the Clinical Follow-up period (30 days), for a total of ~1.9 years.

Immunogenicity

At the sample level, individual samples are characterized as ADA-positive or ADA-negative. A subject is considered to have a positive sample at baseline if the last sample prior to the initiation of treatment is ADA-positive. For example, a post-baseline sample from a subject who is ADA-negative at baseline is considered ADA-positive if ADA is detected. A post-baseline sample from a subject who is ADA-positive at baseline is considered ADA-positive if there is a relevant increase in titer (magnitude of the increase in titer considered relevant may vary by drug and assay, and is delineated in the statistical analysis plan). At the subject level, relevant ADA endpoints may include:

- Proportion of subjects with an ADA-positive sample at baseline
- Proportion of ADA-positive subjects (on treatment and overall)
- Proportion of subjects who are persistently positive (e.g., 2 or more sequential ADA-positive samples with an adequate elapse of time in-between)
- Proportion of subjects who have neutralizing antibodies detected in one or more samples Centrally Read ECGs (Parts A and B)

In Part A and Part B, QTc is assessed by a central reader at follow-up visit 1, and on day 1 of Cycle 1 and Cycle 3 (pre-dose and 4 hour post-dose time points). These assessments are used to address the secondary objective of assessing the effect of BMS-986016 administered alone and in combination with BMS-936558 on QTc. ECGs assessed locally by the investigator are also collected at the start of each cycle.

Biomarker Endpoints

Biomarker endpoints from peripheral blood are generally measured at multiple timepoints, and evaluated as both predictive and pharmacodynamic markers in the context of the exploratory biomarker objectives. These may include measures such as levels and change from baseline in levels of the following at each scheduled timepoint:

- Serum soluble factors
- The proportion of specific lymphocyte subsets/expression levels of T cell co-stimulatory markers assessed using flow cytometry
- Expression of genes encoding BMS-986016—stimulated effector functions (perforin, granzyme B, and IFN-γ) and genes encoding T cell co-stimulatory receptors (PD-1, PD-L1, and CTLA-4).
- Percent of subjects expressing single nucleotide polymorphisms linked to PD-1 genes (per SNP)
- Measures of the quantity and diversity of antibodies observed to tumor-associated antigens (Part C only)

Biomarker endpoints from tumor biopsies are explored predominantly in an effort to identify baseline markers predictive of efficacy, since they are only measured at baseline for most subjects. For the subset of subjects who have both pre-treatment and on-treatment biopsies, pharmacodynamic associations are explored. Endpoints may include measures, such as pre-treatment levels and change in levels observed on-treatment of:

- Functional status of lymphocytes measured as the percent of CD8+ T-cells positive for IFN-γ and granzyme B expression, and the geometric mean intensity (log-scale) of CD8+ cells that are positive for IFN-γ and granzyme B expression (via ex vivo functional assay)
- Expression of genes encoding BMS-986016-stimulated effector functions (perforin, granzyme B, and IFN-γ) and genes encoding T cell co-stimulatory receptors (PD-1, PD-L1, and CTLA-4)
- IHC assessment of the presence/absence and intensity (measured using a discrete scale: such as 0, 1, 2, 3, 4) of expression of LAG-3, MHC class II, PD-1, PD-L1, and PD-L2.

Appropriate functional transformation of these exploratory measures are applied as necessary.

Pharmacokinetics

BMS-936558 concentration-time data at scheduled trough (Ctrough) and end-of-infusion timepoints is evaluated as an exploratory endpoint. Measurements are collected on treatment (up to 12 cycles) and for up to 135 days during the post-treatment follow-up.

PK parameters for BMS-986016 are calculated using noncompartmental analyses. Summary statistics are tabulated for the PK parameters of BMS-986016 by dose and study day/cycle. To describe the association of these parameters with dose of BMS-986016, scatter plots of Cmax and AUC(TAU) versus dose are provided for each day/cycle measured. Dose proportionality of BMS-986016 when administered alone or co-administered with BMS-936558 is also assessed based on a power model. Trough concentrations of BMS-986016 re plotted versus study day and cycle. BMS-936558 end-of-infusion and trough (Ctrough) concentrations are tabulated using summary statistics.

SEQUENCE SUMMARY

| SEQ ID NO: | SEQUENCE |
|---|---|
| 1 | Heavy Chain Amino Acid Sequence Anti-LAG-3 mAb (BMS-986016) (variable region underlined; constant region bold) QVQLQQWGAGLLKPSETLSLTCAVYGGSFSDYYWNWIRQPPGKGLEWIGE INHRGSTNSNPSLKSRVTLSLDTSKNQFSLKLRSVTAADTAVYYCAFGYS DYEYNWFDPWGQGTLVTVSSASTKGPSVPPLAPCSRSTSESTAALGCLVK DYFPEPVTVSWNSGALTSGVHTFPAVLQSSGLYSLSSVVTVPSSSLGTKT YTCNVDHKPSNTKVDKRVESKYGPPCPPCPAPEFLGGPSVFLFPPKPKDT LMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK* |

SEQUENCE SUMMARY

| SEQ ID NO: | SEQUENCE |
|---|---|
| 2 | Light Chain Amino Acid Sequence<br>Anti-LAC-3 mAb (BMS-986016)<br>(variable region underlined; constant region bold)<br>EIVLTQSPATLSLSPGERATLSCRASQSISSYLAWYQQKPGQAPRLLIYD<br><br>ASNRATCIPARFSGSGSCTDFTLTISSLEPEDFAVYYCQQRSNWPLTFGQ<br><br>GINLEIKRTVAAPSVPIFPPSDEQLKSGTASVVCLLNNFYPREAKVQWKV<br><br>DNALQSGNSQESVTEQDSKDSTYSLSSTLTLSKADYEKHKVYACEVTHQG<br><br>LSSPVTKSFNRGEC* |
| 3 | Heavy Chain Variable Region (VH) Amino Acid Sequence<br>Anti-LAG-3 mAb (BMS-986016)<br>QVQLQQWGAGLLKPSETLSLTCAVYGGSFSDYYWNWIRQPPGKGLEWI<br><br>GEINHRCSTNSNPSLKSRVILSLDTSKNQFSLKLRSVTAADTAVYYCAFC<br><br>YSDYEYNWFDPWGQGTLVTVSS |
| 4 | Heavy Chain Variable Region (VH) Nucleotide Sequence<br>Anti-LAG-3 mAb (BMS-986016)<br>caggtgcagctacagcagtggggcgcaggactgttgaagccttggagaccct<br><br>gtccctcacctgcgctgtctatggtgggtccttcagtgattactactggaact<br><br>ggatccgccagccccagggaaggggctggagtggattggggaaatcaatcat<br><br>cgtggaagcaccaactccaacccgtccctcaagagtcgagtcaccctatcact<br><br>agacacgtccaagaaccagttctccctgaagctgaggtctgtgaccgccgcgg<br><br>acacggctgtgtattactgtgcgtttgqatatagtgactacgagtacaactgg<br><br>ttcgacccctggggccagggaaccctggtcaccgtctcctca |
| 5 | Light Chain Variable Region (VL) Amino Acid Sequence<br>Anti-LAG-3 mAb (BMS-986016)<br>EIVLTQSPATLSLSPGERATLSCRASQSISSYLAWYQQKPCQAPRLLIYD<br><br>ASNRATGIPARFSGSGSGTDFTLTISSLEPEDFAVYYCQQRSNWPLTFGQ<br><br>GTNLEIK |
| 6 | Light Chain Variable Region (VL) Nucleotide Sequence<br>Anti-LAG-3 mAb (BMS-986016)<br>gaaattgtgttgacacagtctccagccaccctgtctttgtctccaggggaaag<br><br>agccaccctctcctgcagggccagtcagagtattagcagctacttagcctggt<br><br>accaacagaaacctggccaggctcccaggctcctcatctatgatgcatccaac<br><br>agggccactggcatcccagccaggttcagtggcagtgggtctgggacagactt<br><br>cactctcaccatcagcagcctagagcctgaagattttgcagtttattactgtc<br><br>agcagcgtagcaactggcctctcacttttggccaggggaccaacctggagatc<br><br>aaa |
| 7 | Heavy Chain CDR1 Amino Acid Sequence<br>Anti-LAG-3 mAb (BMS-986016)<br>DYYWN |
| 8 | Heavy Chain CDR2 Amino Acid Sequence<br>Anti-LAG-3 mAb (BMS-986016)<br>EINHRGSTNSNPSLKS |
| 9 | Heavy Chain CDR3 Amino Acid Sequence<br>Anti-LAG-3 mAb (BMS-986016)<br>GYSDYEYNWFDP |

-continued

```
                         SEQUENCE SUMMARY
SEQ
ID NO: SEQUENCE

10   Light Chain CDR1 Amino Acid Sequence
       Anti-LAG-3 mAb (BMS-986016)
       RASQSISSYLA 11   Light Chain CDR2 Amino Acid Sequence
       Anti-LAG-3 mAb (BMS-986016)
       DASNRAT 12   Light Chain CDR3 Amino Acid Sequence
       Anti-LAG-3 mAb (BMS-986016)
       QQRSNWPLT 13   Human LAG-3 Amino Acid Sequence
       MWEAQFLGLLFLQPLWVAPVKPLQPGAEVPVVWAQEGAPAQLPCSPTIPLQD

LSLLRRAGVTWQHQPDSGPPAAAPGHPLAPGPHPAAPSSWGPRPRRYTVLSVG

PGGLRSGRLPLQPRVQLDERGRQRGDFSLWLRPARRADAGEYRAAVHLRDR

ALSCRLRLRLGQASMTASPPGSLRASDWVILNCSFSRPDRPASVHWFRNRGQ

GRVPVRESPHHHLAESFLFLPQVSPMDSGPWGCILTYRDGFNVSIMYNLTVLG

LEPPTPLIVYAGAGSRVGLPCRLPAGVGIRSFLTAKWIPPGGGPDLLVTGDN

GDFTLRLEDVSQAQAGTYTCHIHLQEQQLNATVTLAIITVTPKSFGSPGSLGKL

LCEVTPVSGQERFVWSSLDTPSQRSFSGPWLEAQEAQLLSQPWQCQLYQGERL

LGAAVYFTELSSPGAQRSGRAPGALPAGHLLLFLTLGVLSLLLLVTGAFGFHLW

RRQWRPRRFSALEQGIHPPQAQSKIEELEQEPEPEPEPEPEPEPEPEPEPEQL*

14   LAG-3 Epitope
       PGHPLAPG

15   LAG-3 Epitope
       HPAAPSSW

16   LAG-3 Epitope
       PAAPSSWG

17   Heavy Chain Amino Acid Sequence
       Anti-PD-1 mAb (BM5936558; 5C4 in WO 2006/121168)
       (variable region underlined; constant region bold)
       QVQLVESGGGVVQPGRSLRLDCKASGITFSNSGMHWVRQAPGKGL

EWVAVIWYDGSKRYYADSVKGRFTISRDNSKNTLFLQMNSLRAEDT

AVYYCATNDDYWGQGTLVTVSSASTKGPSVFPLAPCSRSTSESTAA

LGCLVKDYFPEPVTVSWNSGALTSGVHTFPAVLQSSGLYSLSSVVT

VPSSSLGTKTYTCNVDHKPSNTKVDKRVESKYGPPCPPCPAPEFLG

GPSVFLFPPKPKDTLMISRTPEVTCVVVDVSQEDPEVQFNWYVDGV

EVHNAKTKPREEQFNSTYRVVSVLTVLHQDWLNGKEYKCKVSNKG

LPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNV

FSCSVMHEALHNHYTQKSLSLSLGK

18   Light Chain Amino Acid Sequence
       Anti-PD-1 mAb (BM5936558; 5C4 in WO 2006/121168)
       (variable region underlined; constant region bold)
       EIVLTQSPATLSLSPGERATLSCRASQSVSSYLAWYQQKPGQAPRLLI

YDASNRATGIPARFSGSGSGTDFTLTISSLEPEDFAVYYCQQSSNWPR

TFGQGTKVEIKRTVAAPSVFIFPPSDEQLKSGTASVVCLLNNFYPREA
```

SEQUENCE SUMMARY

| SEQ ID NO: | SEQUENCE |
|---|---|
| | KVQWKVDNALQSGNSQESVTEQDSKDSTYSLSSTLTLSKADYEKHK |
| | VYACEVTHQGLSSPVTKSFNRGEC |
| 19 | Heavy Chain Variable Region (VH) Amino Acid Sequence Anti-PD-1 mAb (BMS936558; 5C4 in WO 2006/121168) (SEQ ID NO: 4 from WO 2006/121168)<br>QVQLVESGGGVVQPGRSLRLDCKASGITFSNSGMHWVRQAPGKGLEWVAV<br>IWYDGSKRYYADSVKGRFTISRDNSKNTLFLQMNSLRAEDTAVYYCATND<br>DYWGQGTLVTVSS |
| 20 | Heavy Chain Variable Region (VH) Nucleotide Sequence Anti-PD-1 mAb (BMS936558; 5C4 in WO 2006/121168) (SEQ ID NO: 60 from WO 2006/121168)<br>cag gtg cag ctg gtg gag tct ggg gga ggc gtg gtc cag cct ggg<br>agg tcc ctg aga ctc gac tgt aaa gcg tct gga atc acc ttc agt<br>aac tct ggc atg cac tgg gtc cgc cag gct cca ggc aag ggg ctg<br>gag tgg gtg gca gtt att tgg tat gat gga agt aaa aga tac tat<br>gca gac tcc gtg aag ggc cga ttc acc atc tcc aga gac aat tcc<br>aag aac acg ctg ttt ctg caa atg aac agc ctg aga gcc gag gac<br>acg gct gtg tat tac tgt gcg aca aac gac gac tac tgg ggc cag<br>gga acc ctg gtc acc gtc tcc tca |
| 21 | Light Chain Variable Region (VL) Amino Acid Sequence Anti-PD-1 mAb (BMS936558; 5C4 in WO 2006/121168) (SEQ ID NO: 11 from WO 2006/121168)<br>EIVLTQSPATLSLSPGERATLSCRASQSVSSYLAWYQQKPGQAPRLLIYD<br>ASNRATGIPARFSGSGSGTDFTLTISSLEPEDFAVYYCQQSSNWPRTFGQ<br>GTKVEIK |
| 22 | Light Chain Variable Region (VL) Nucleotide Sequence Anti-PD-1 mAb (BMS936558; 5C4 in WO 2006/121168) (SEQ ID NO: 67 from WO 2006/121168)<br>gaa att gtg ttg aca cag tct cca gcc acc ctg tct ttg tct cca<br>ggg gaa aga gcc acc ctc tcc tgc agg gcc agt cag agt gtt agt<br>agt tac tta gcc tgg tac caa cag aaa cct ggc cag gct ccc agg<br>ctc ctc atc tat gat gca tcc aac agg gcc act ggc atc cca gcc<br>agg ttc agt ggc agt ggg tct ggg aca gac ttc act ctc acc atc<br>agc agc cta gag cct gaa gat ttt gca gtt tat tac tgt cag cag<br>agt agc aac tgg cct cgg acg ttc ggc caa ggg acc aag gtg gaa<br>atc aaa |
| 23 | Heavy Chain CDR1 Amino Acid Sequence Anti-PD-1 mAb (BMS936558; 5C4 in WO 2006/121168) (SEQ ID NO: 18 from WO 2006/121168)<br>NSGMH |
| 24 | Heavy Chain CDR2 Amino Acid Sequence Anti-PD-1 mAb (BMS936558; 5C4 in WO 2006/121168) (SEQ ID NO: 25 from WO 2006/121168)<br>VIWYDGSKRYYADSVKG |
| 25 | Heavy Chain CDR3 Amino Acid Sequence Anti-PD-1 mAb (BMS936558; 5C4 in WO 2006/121168) (SEQ ID NO: 32 from WO 2006/121168)<br>NDDY |

SEQUENCE SUMMARY

| SEQ ID NO: | SEQUENCE |
|---|---|
| 26 | Light Chain CDR1 Amino Acid Sequence<br>Anti-PD-1 mAb (BMS936558; 5C4 in WO 2006/121168)<br>(SEQ ID NO: 39 from WO 2006/121168)<br>RASQSVSSYLA |
| 27 | Light Chain CDR2 Amino Acid Sequence<br>Anti-PD-1 mAb (BMS936558; 5C4 in WO 2006/121168)<br>(SEQ ID NO: 46 from WO 2006/121168)<br>DASNRAT |
| 28 | Light Chain CDR3 Amino Acid Sequence<br>Anti-PD-1 mAb (BMS936558; 5C4 in WO 2006/121168)<br>(SEQ ID NO: 53 from WO 2006/121168)<br>QQSSNWPRT |
| 29 | Complete PD-1 sequence (GenBank Accession No.: U64863)<br>agtttccctt ccgctcacct ccgcctgagc agtggagaag gcggcactct<br>ggtggggctg ctccaggcat gcagatccca caggcgccct ggccagtcgt<br>ctgggcggtg ctacaactgg gctggcggcc aggatggttc ttagactccc<br>cagacaggcc ctggaacccc cccaccttct tcccagccct gctcgtggtg<br>accgaagggg acaacgccac cttcacctgc agcttctcca acacatcgga<br>gagcttcgtg ctaaactggt accgcatgag ccccagcaac cagacggaca<br>agctggccgc cttccccgag gaccgcagcc agccggcca ggactgccgc<br>ttccgtgtca cacaactgcc aacgggcgt gacttccaca tgagcgtggt<br>cagggcccgg cgcaatgaca gcggcaccta cctctgtggg gccatctccc<br>tggcccccaa ggcgcagatc aaagagagcc tgcgggcaga gctcagggtg<br>acagagagaa gggcagaagt gcccacagcc caccccagcc cctcacccag<br>gccagccggc cagttccaaa ccctggtggt tggtgtcgtg ggcggcctgc<br>tgggcagcct ggtgctgcta gtctgggtcc tggccgtcat ctgctcccgg<br>gccgcacgag ggacaatagg agccaggcgc accggccagc ccctgaagga<br>ggaccctca gccgtgcctg tgttctctgt ggactatggg gagctggatt<br>tccagtggcg agagaagacc ccggagcccc ccgtgccctg tgtccctgag<br>cagacggagt atgccaccat tgtctttcct agcggaatgg gcacctcatc<br>ccccgcccgc aggggctcag ccgacggccc tcggagtgcc cagccactga<br>ggcctgagga tggacactgc tcttggcccc tctgaccggc ttccttggcc<br>accagtgttc tgcagaccct ccaccatgag cccgggtcag cgcatttcct<br>caggagaagc aggcagggtg caggccattg caggccgtcc aggggctgag<br>ctgcctgggg gcgaccgggg ctccagcctg cacctgcacc aggcacagcc<br>ccaccacagg actcatgtct caatgcccac agtgagccca ggcagcaggt<br>gtcaccgtcc cctacaggga gggccagatg cagtcactgc ttcaggtcct<br>gccagcacag agctgcctgc gtccagctcc ctgaatctct gctgctgctg<br>ctgctgctgc tgctgctgcc tgcggcccgg ggctgaaggc gccgtggccc<br>tgcctgacgc ccggagcct cctgcctgaa cttggggct ggttggagat<br>ggccttggag cagccaaggt gcccctggca gtggcatccc gaaacgccct<br>ggacgcaggg cccaagactg ggcacaggag tgggaggtac atggggctgg |

SEQUENCE SUMMARY

SEQ ID NO: SEQUENCE ggactcccca ggagttatct gctccctgca ggcctagaga agtttcaggg aaggtcagaa gagctcctgg ctgtggtggg cagggcagga aaccccctccc acctttacac atgcccaggc agcacctcag gccctttgtg gggcagggaa gctgaggcag taagcgggca ggcagagctg gaggcctttc aggccagcca gcactctggc ctcctgccgc cgcattccac cccagcccct cacaccactc gggagaggga catcctacgg tcccaaggtc aggagggcag ggctggggtt gactcaggcc cctcccagct gtggccacct gggtgttggg agggcagaag tgcaggcacc tagggccccc catgtgccca ccctgggagc tctccttgga acccattcct gaaattattt aaaggggttg gccgggctcc caccagggcc tgggtgggaa ggtacaggcg ttcccccggg gcctagtacc cccgcgtggc ctatccactc ctcacatcca cacactgcac ccccactcct ggggcagggc caccagcatc caggcggcca gcaggcacct gagtggctgg acaagggat ccccccttccc tgtggttcta ttatattata attataatta aatatgagag catgct Heavy Chain Nucleotide Sequence
Anti-LAG-3 mAb (BMS-986016)
caggtgcagctacagcagtggggcgcaggactgttgaagccttcggagaccctgtccct cacctgcgctgtctatggtgggtccttcagtgattactactggaactggatccgccag cccccagggaaggggctggagtggattgggaaatcaatcatcgtggaagcaccaact ccaacccgtccctcaagagtcgagtcaccctatcactagacacgtccaagaaccagtt ctccctgaagctgaggtctgtgaccgccgcggacacggctgtgtattactgtgcgtttg gatatagtgactacgagtacaactggttcgaccccctgggggccagggaaccctggtcacc gtctcctcagctagcaccaagggcccatccgtcttccccctggcgccctgctccaggagc acctccgagagcacagccgccctgggctgcctggtcaaggactacttccccgaaccggtg acggtgtcgtggaactcaggcgccctgaccagcggcgtgcacaccttcccggctgtccta cagtcctcaggactctactccctcagcagcgtggtgaccgtgccctccagcagcttgggc acgaagacctacacctgcaacgtagatcacaagcccagcaacaccaaggtggacaagaga gttgagtccaaatatggtcccccatgcccaccatgcccagcacctgagttcctggggggga ccatcagtcttcctgttccccccaaaacccaaggacactctcatgatctcccggacccct gaggtcacgtgcgtggtggtggacgtgagccaggaagaccccgaggtccagttcaactgg tacgtggatggcgtggaggtgcataatgccaagacaaagccgcgggaggagcagttcaa cagcacgtaccgtgtggtcagcgtcctcaccgtcctgcaccaggactggctgaacggcaa ggagtacaagtgcaaggtctccaacaaaggcctcccgtcctccatcgagaaaaccatctc caaagccaaagggcagccccgagagccacaggtgtacaccctgcccccatcccaggagga gatgaccaagaaccaggtcagcctgacctgcctggtcaaaggcttctaccccagcgacat cgccgtggagtgggagagcaatgggcagccggagaacaactacaagaccacgcctcccgt gctggactccgacggctccttcttcctctacagcaggctaaccgtggacaagagcaggtg

SEQUENCE SUMMARY

SEQ ID NO: SEQUENCE gcaggaggggaatgtcttctcatgctccgtgatgcatgaggctctgcacaaccactacac acagaagagcctctccctgtctctgggtaaatga Light Chain Nucleotide Sequence
Anti-LAG-3 mAb (BMS-986016)
gaaattgtgttgacacagtctccagccaccctgtctttgtctccaggggaaagagccacc ctctcctgcagggccagtcagagtattagcagctacttagcctggtaccaacagaaacct ggccaggctcccaggctcctcatctatgatgcatccaacagggccactggcatcccag ccaggttcagtggcagtgggtctgggacagacttcactctcaccatcagcagcctagagc ctgaagattttgcagtttattactgtcagcagcgtagcaactggcctctcacttttggcc aggggaccaacctggagatcaaacgtacggtggctgcaccatctgtcttcatcttcccgc catctgatgagcagttgaaatctggaactgcctctgttgtgtgcctgctgaataacttct atcccagagaggccaaagtacagtggaaggtggataacgccctccaatcgggtaactccc aggagagtgtcacagagcaggacagcaaggacagcacctacagcctcagcagcaccctga cgctgagcaaagcagactacgagaaacacaaagtctacgcctgcgaagtcacccatcagg gcctgagctcgcccgtcacaaagagcttcaacaggggagagtgttag

---

What is claimed is:

1. A pharmaceutical composition comprising: (a) 80 mg of an anti-LAG-3 antibody comprising CDR1, CDR2 and CDR3 domains of the heavy chain variable region having the sequence set forth in SEQ ID NO: 3, and CDR1, CDR2 and CDR3 domains of the light chain variable region having the sequence set forth in SEQ ID NO: 5; and (b) 240 mg of an anti-PD-1 antibody comprising CDR1, CDR2 and CDR3 domains of the heavy chain variable region having the sequence set forth in SEQ ID NO: 19, and CDR1, CDR2 and CDR3 domains of the light chain variable region having the sequence set forth in SEQ ID NO: 21.

2. The pharmaceutical composition of claim 1, wherein the anti-LAG-3 antibody comprises:
   (a) a heavy chain variable region CDR1 comprising the sequence set forth in SEQ ID NO: 7;
   (b) a heavy chain variable region CDR2 comprising the sequence set forth in SEQ ID NO: 8;
   (c) a heavy chain variable region CDR3 comprising the sequence set forth in SEQ ID NO: 9;
   (d) a light chain variable region CDR1 comprising the sequence set forth in SEQ ID NO: 10;
   (e) a light chain variable region CDR2 comprising the sequence set forth in SEQ ID NO: 11; and
   (f) a light chain variable region CDR3 comprising the sequence set forth in SEQ ID NO: 12.

3. The pharmaceutical composition of claim 1, wherein the anti-LAG-3 antibody comprises heavy and light chain variable regions comprising the sequences set forth in SEQ ID NOs: 3 and 5, respectively.

4. The pharmaceutical composition of claim 1, wherein the anti-LAG-3 antibody comprises heavy and light chains comprising the sequences set forth in SEQ ID NOs: 1 and 2, respectively.

5. The pharmaceutical composition of claim 1, wherein the anti-PD-1 antibody comprises:
   (a) a heavy chain variable region CDR1 comprising the sequence set forth in SEQ ID NO: 23;
   (b) a heavy chain variable region CDR2 comprising the sequence set forth in SEQ ID NO: 24;
   (c) a heavy chain variable region CDR3 comprising the sequence set forth in SEQ ID NO: 25;
   (d) a light chain variable region CDR1 comprising the sequence set forth in SEQ ID NO: 26;
   (e) a light chain variable region CDR2 comprising the sequence set forth in SEQ ID NO: 27; and
   (f) a light chain variable region CDR3 comprising the sequence set forth in SEQ ID NO: 28.

6. The pharmaceutical composition of claim 2, wherein the anti-PD-1 antibody comprises:
   (a) a heavy chain variable region CDR1 comprising the sequence set forth in SEQ ID NO: 23;
   (b) a heavy chain variable region CDR2 comprising the sequence set forth in SEQ ID NO: 24;
   (c) a heavy chain variable region CDR3 comprising the sequence set forth in SEQ ID NO: 25;
   (d) a light chain variable region CDR1 comprising the sequence set forth in SEQ ID NO: 26;
   (e) a light chain variable region CDR2 comprising the sequence set forth in SEQ ID NO: 27; and (f) a light chain variable region CDR3 comprising the sequence set forth in SEQ ID NO: 28.

7. The pharmaceutical composition of claim 1, wherein the anti-PD-1 antibody comprises heavy and light chain variable regions comprising the sequences set forth in SEQ ID NOs: 19 and 21, respectively.

8. The pharmaceutical composition of claim 3, wherein the anti-PD-1 antibody comprises heavy and light chain variable regions comprising the sequences set forth in SEQ ID NOs: 19 and 21, respectively.

9. The pharmaceutical composition of claim 1, wherein the anti-PD-1 antibody comprises heavy and light chains comprising the sequences as set forth in SEQ ID NOs: 17 and 18, respectively.

10. The pharmaceutical composition of claim 4, wherein the anti-PD-1 antibody comprises heavy and light chains comprising the sequences as set forth in SEQ ID NOs: 17 and 18, respectively.

11. The pharmaceutical composition of claim 1, wherein the anti-LAG-3 and anti-PD-1 antibodies are formulated for intravenous administration.

12. A kit for treating a solid tumor in a human patient, comprising:
  (a) 80 mg of an anti-LAG-3 antibody comprising CDR1, CDR2 and CDR3 domains of the heavy chain variable region having the sequence set forth in SEQ ID NO: 3, and CDR1, CDR2 and CDR3 domains of the light chain variable region having the sequence set forth in SEQ ID NO: 5;
  (b) 240 mg of an anti-PD-1 antibody comprising CDR1, CDR2 and CDR3 domains of the heavy chain variable region having the sequence set forth in SEQ ID NO: 19, and CDR1, CDR2 and CDR3 domains of the light chain variable region having the sequence set forth in SEQ ID NO: 21; and
  (c) instructions for using the anti-LAG-3 antibody and the anti-PD-1 antibody in a method for treating a solid tumor in a human patient.

* * * * *

SEQUENCE LISTING

<160> NUMBER OF SEQ ID NOS: 32

<210> SEQ ID NO 1
<211> LENGTH: 447
<212> TYPE: PRT
<213> ORGANISM: Artificial Sequence
<220> FEATURE:
<223> OTHER INFORMATION: Synthetic: Heavy Chain Amino Acid Sequence;
      Anti-LAG-3 mAb (BMS-986016)

<400> SEQUENCE: 1

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Synthetic: Light Chain Amino Acid Sequence;
      Anti-LAG-3 mAb (BMS-986016)

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 120
<212> TYPE: PRT
<213> ORGANISM: Artificial Sequence
<220> FEATURE:
<223> OTHER INFORMATION: Synthetic: Heavy Chain Variable Region (VH)
      Amino Acid Sequence; Anti-LAG-3 mAb (BMS-986016)

<400> SEQUENCE: 3

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
                 20                  25                  30

Tyr Trp Asn Trp Ile Arg Gln Pro Pro Gly Lys Gly Leu Glu Trp Ile
             35                  40                  45

Gly Glu Ile Asn His Arg Gly Ser Thr Asn Ser Asn Pro Ser Leu Lys
 50                  55                  60

Ser Arg Val Thr Leu Ser Leu Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 4
<211> LENGTH: 360
<212> TYPE: DNA
<213> ORGANISM: Artificial Sequence
<220> FEATURE:
<223> OTHER INFORMATION: Synthetic: Heavy Chain Variable Region (VH)
      Nucleotide Sequence; Anti-LAG-3 mAb (BMS-986016)

<400> SEQUENCE: 4
caggtgcagc tacagcagtg gggcgcagga ctgttgaagc cttcggagac cctgtccctc    60
```

```
acctgcgctg tctatggtgg gtccttcagt gattactact ggaactggat ccgccagccc      120
ccagggaagg ggctggagtg gattggggaa atcaatcatc gtggaagcac caactccaac      180
ccgtccctca agagtcgagt caccctatca ctagacacgt ccaagaacca gttctccctg      240
aagctgaggt ctgtgaccgc cgcggacacg gctgtgtatt actgtgcgtt tggatatagt      300
gactacgagt acaactggtt cgaccccttgg ggccagggaa ccctggtcac cgtctcctca     360
```

<210> SEQ ID NO 5
<211> LENGTH: 107
<212> TYPE: PRT
<213> ORGANISM: Artificial Sequence
<220> FEATURE:
<223> OTHER INFORMATION: Synthetic: Light Chain Variable Region (VL)
      Amino Acid Sequence; Anti-LAG-3 mAb (BMS-986016)

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105

<210> SEQ ID NO 6
<211> LENGTH: 321
<212> TYPE: DNA
<213> ORGANISM: Artificial Sequence
<220> FEATURE:
<223> OTHER INFORMATION: Synthetic: Light Chain Variable Region (VL)
      Nucleotide Sequence; Anti-LAG-3 mAb (BMS-986016)

<400> SEQUENCE: 6

```
gaaattgtgt tgacacagtc tccagccacc ctgtctttgt ctccagggga aagagccacc      60
ctctcctgca gggccagtca gagtattagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac ttttggccag     300
gggaccaacc tggagatcaa a                                                321
```

<210> SEQ ID NO 7
<211> LENGTH: 5
<212> TYPE: PRT
<213> ORGANISM: Artificial Sequence
<220> FEATURE:
<223> OTHER INFORMATION: Synthetic: Heavy Chain CDR1 Amino Acid
      Sequence; Anti-LAG-3 mAb (BMS-986016)

<400> SEQUENCE: 7

Asp Tyr Tyr Trp Asn
1               5

```
<210> SEQ ID NO 8
<211> LENGTH: 16
<212> TYPE: PRT
<213> ORGANISM: Artificial Sequence
<220> FEATURE:
<223> OTHER INFORMATION: Synthetic: Heavy Chain CDR2 Amino Acid
      Sequence; Anti-LAG-3 mAb (BMS-986016)

<400> SEQUENCE: 8

Glu Ile Asn His Arg Gly Ser Thr Asn Ser Asn Pro Ser Leu Lys Ser
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Synthetic: Heavy Chain CDR3 Amino Acid
      Sequence; Anti-LAG-3 mAb (BMS-986016)

<400> SEQUENCE: 9

Gly Tyr Ser Asp Tyr Glu Tyr Asn Trp Phe Asp Pro
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic: Light Chain CDR1 Amino Acid
      Sequence; Anti-LAG-3 mAb (BMS-986016)

<400> SEQUENCE: 10

Arg Ala Ser Gln Ser Ile Ser Ser Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic: Light Chain CDR2 Amino Acid
      Sequence; Anti-LAG-3 mAb (BMS-986016)

<400> SEQUENCE: 11

Asp Ala Ser Asn Arg Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic: Light Chain CDR3 Amino Acid
      Sequence; Anti-LAG-3 mAb (BMS-986016)

<400> SEQUENCE: 12

Gln Gln Arg Ser Asn Trp Pro Leu Thr
1               5

<210> SEQ ID NO 13
<211> LENGTH: 525
<212> TYPE: PRT
<213> ORGANISM: Homo sapiens
<220> FEATURE:
<221> NAME/KEY: misc_feature
<223> OTHER INFORMATION: Human LAG-3 Amino Acid Sequence
```

<400> SEQUENCE: 13

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415
```

```
Gly Glu Arg Leu Leu Gly Ala Ala Val Tyr Phe Thr Glu Leu Ser Ser
                420                 425                 430

Pro Gly Ala Gln Arg Ser Gly Arg Ala Pro Gly Ala Leu Pro Ala Gly
            435                 440                 445

His Leu Leu Leu Phe Leu Thr Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Pro Glu Gln Leu
            515                 520                 525

<210> SEQ ID NO 14
<211> LENGTH: 8
<212> TYPE: PRT
<213> ORGANISM: Artificial Sequence
<220> FEATURE:
<223> OTHER INFORMATION: Synthetic: LAG-3 Epitope

<400> SEQUENCE: 14

Pro Gly His Pro Leu Ala Pro Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic: LAG-3 Epitope

<400> SEQUENCE: 15

His Pro Ala Ala Pro Ser Ser Trp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic: LAG-3 Epitope

<400> SEQUENCE: 16

Pro Ala Ala Pro Ser Ser Trp Gly
1               5

<210> SEQ ID NO 17
<211> LENGTH: 440
<212> TYPE: PRT
<213> ORGANISM: Artificial Sequence
<220> FEATURE:
<223> OTHER INFORMATION: Synthetic: Heavy Chain Amino Acid Sequence;
      Anti-PD-1 mAb (BMS936558)

<400> SEQUENCE: 17

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
```

```
                35                  40                  45
Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
                115                 120                 125

Arg Ser Thr Ser Glu Ser Thr Ala Ala Leu Gly Cys Leu Val Lys Asp
                130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
                195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
                275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
                370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440

<210> SEQ ID NO 18
```

<211> LENGTH: 214
<212> TYPE: PRT
<213> ORGANISM: Artificial Sequence
<220> FEATURE:
<223> OTHER INFORMATION: Synthetic: Light Chain Amino Acid Sequence;
      Anti-PD-1 mAb (BMS936558)

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 113
<212> TYPE: PRT
<213> ORGANISM: Artificial Sequence
<220> FEATURE:
<223> OTHER INFORMATION: Synthetic: Heavy Chain Variable Region (VH)
      Amino Acid Sequence; Anti-PD-1 mAb (BMS936558)

<400> SEQUENCE: 19

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110
Ser

<210> SEQ ID NO 20
<211> LENGTH: 339
<212> TYPE: DNA
<213> ORGANISM: Artificial Sequence
<220> FEATURE:
<223> OTHER INFORMATION: Synthetic: Heavy Chain Variable Region (VH)
      Nucleotide Sequence; Anti-PD-1 mAb (BMS936558)

<400> SEQUENCE: 20
caggtgcagc tggtggagtc tgggggaggc gtggtccagc ctggggaggtc cctgagactc    60 gactgtaaag cgtctggaat caccttcagt aactctggca tgcactgggt ccgccaggct   120
ccaggcaagg ggctggagtg ggtggcagtt atttggtatg atggaagtaa aagatactat   180
gcagactccg tgaagggccg attcaccatc tccagagaca attccaagaa cacgctgttt   240
ctgcaaatga acagcctgag agccgaggac acggctgtgt attactgtgc gacaaacgac   300
gactactggg gccagggaac cctggtcacc gtctcctca                          339

<210> SEQ ID NO 21
<211> LENGTH: 107
<212> TYPE: PRT
<213> ORGANISM: Artificial Sequence
<220> FEATURE:
<223> OTHER INFORMATION: Synthetic: Light Chain Variable Region (VL)
      Amino Acid Sequence; Anti-PD-1 mAb (BMS936558)

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 22
<211> LENGTH: 321
<212> TYPE: DNA
<213> ORGANISM: Artificial Sequence
<220> FEATURE:
<223> OTHER INFORMATION: Synthetic: Light Chain Variable Region (VL)
      Nucleotide Sequence; Anti-PD-1 mAb (BMS936558)

<400> SEQUENCE: 22
gaaattgtgt tgacacagtc tccagccacc ctgtctttgt ctccagggga aagagccacc    60
ctctcctgca gggccagtca gagtgttagt agttacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240

```
gaagattttg cagtttatta ctgtcagcag agtagcaact ggcctcggac gttcggccaa    300
gggaccaagg tggaaatcaa a                                              321
```

<210> SEQ ID NO 23
<211> LENGTH: 5
<212> TYPE: PRT
<213> ORGANISM: Artificial Sequence
<220> FEATURE:
<223> OTHER INFORMATION: Synthetic: Heavy Chain CDR1 Amino Acid
      Sequence; Anti-PD-1 mAb (BMS936558)

<400> SEQUENCE: 23

Asn Ser Gly Met His
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic: Heavy Chain CDR2 Amino Acid
      Sequence; Anti-PD-1 mAb (BMS936558)

<400> SEQUENCE: 24

Val Ile Trp Tyr Asp Gly Ser Lys Arg Tyr Tyr Ala Asp Ser Val Lys
1               5                   10                  15

Gly

<210> SEQ ID NO 25
<211> LENGTH: 4
<212> TYPE: PRT
<213> ORGANISM: Artificial Sequence
<220> FEATURE:
<223> OTHER INFORMATION: Synthetic: Heavy Chain CDR3 Amino Acid
      Sequence; Anti-PD-1 mAb (BMS936558)

<400> SEQUENCE: 25

Asn Asp Asp Tyr
1

<210> SEQ ID NO 26
<211> LENGTH: 11
<212> TYPE: PRT
<213> ORGANISM: Artificial Sequence
<220> FEATURE:
<223> OTHER INFORMATION: Synthetic: Light Chain CDR1 Amino Acid
      Sequence; Anti-PD-1 mAb (BMS936558)

<400> SEQUENCE: 26

Arg Ala Ser Gln Ser Val Ser Ser Tyr Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic: Light Chain CDR2 Amino Acid
      Sequence; Anti-PD-1 mAb (BMS936558)

<400> SEQUENCE: 27

Asp Ala Ser Asn Arg Ala Thr
1               5

<210> SEQ ID NO 28

```
<211> LENGTH: 9
<212> TYPE: PRT
<213> ORGANISM: Artificial Sequence
<220> FEATURE:
<223> OTHER INFORMATION: Synthetic: Light Chain CDR3 Amino Acid
      Sequence; Anti-PD-1 mAb (BMS936558)

<400> SEQUENCE: 28

Gln Gln Ser Ser Asn Trp Pro Arg Thr
1               5

<210> SEQ ID NO 29
<211> LENGTH: 2106
<212> TYPE: DNA
<213> ORGANISM: Homo sapiens
<220> FEATURE:
<221> NAME/KEY: misc_feature
<223> OTHER INFORMATION: Complete PD-1 sequence

<400> SEQUENCE: 29
agtttccctt ccgctcacct ccgcctgagc agtggagaag gcggcactct ggtggggctg     60
ctccaggcat gcagatccca caggcgccct ggccagtcgt ctgggcggtg ctacaactgg    120
gctggcggcc aggatggttc ttagactccc agacaggccc tggaacccc ccacccttct    180 tcccagccct gctcgtggtg accgaagggg acaacgccac cttcacctgc agcttctcca    240
acacatcgga gagcttcgtg ctaaactggt accgcatgag ccccagcaac cagacggaca    300
agctggccgc cttccccgag gaccgcagcc agcccggcca ggactgccgc ttccgtgtca    360
cacaactgcc caacgggcgt gacttccaca tgagcgtggt cagggcccgg cgcaatgaca    420
gcggcaccta cctctgtggg gccatctccc tggcccccaa ggcgcagatc aaagagagcc    480
tgcgggcaga gctcagggtg acagagagaa gggcagaagt gcccacagcc accccagcc    540 cctcacccag gccagccggc cagttccaaa ccctggtggt tggtgtcgtg gcggcctgc    600 tgggcagcct ggtgctgcta gtctgggtcc tggccgtcat ctgctcccgg gccgcacgag    660
ggacaatagg agccaggcgc accggccagc ccctgaagga ggacccctca gccgtgcctg    720
tgttctctgt ggactatggg gagctggatt ccagtggcg agagaagacc ccggagcccc    780
ccgtgccctg tgtccctgag cagacggagt atgccaccat tgtctttcct agcggaatgg    840
gcacctcatc cccgcccgc aggggctcag ccgacggccc tcggagtgcc cagccactga    900
ggcctgagga tggacactgc tcttggcccc tctgaccggc ttccttggcc accagtgttc    960
tgcagaccct ccaccatgag cccgggtcag cgcatttcct caggagaagc aggcagggtg   1020
caggccattg caggccgtcc aggggctgag ctgcctgggg cgaccggggc tccagcctg    1080 cacctgcacc aggcacagcc ccaccacagg actcatgtct caatgccac agtgagccca   1140 ggcagcaggt gtcaccgtcc cctacaggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gccgtggccc tgcctgacgc cccggagcct   1320
cctgcctgaa cttgggggct ggttggagat ggccttggag cagccaaggt gcccctggca   1380
gtggcatccc gaaacgccct ggacgcaggg cccaagactg gcacaggag tgggaggtac    1440 atggggctgg ggactcccca ggagttatct gctccctgca ggcctagaga agtttcaggg   1500
aaggtcagaa gagctcctgg ctgtggtggg caggcagga aacccctccc acctttacac    1560
atgcccaggc agcacctcag gcccttgtg gggcagggaa gctgaggcag taagcgggca   1620
ggcagagctg gaggcctttc aggccagcca gcactctggc ctcctgccgc cgcattccac   1680
```

```
cccagcccct cacaccactc gggagaggga catcctacgg tcccaaggtc aggagggcag    1740
ggctggggtt gactcaggcc cctcccagct gtggccacct gggtgttggg agggcagaag    1800
tgcaggcacc tagggccccc catgtgccca ccctgggagc tctccttgga acccattcct    1860
gaaattattt aaaggggttg gccgggctcc caccagggcc tgggtgggaa ggtacaggcg    1920
ttcccccggg gcctagtacc cccgcgtggc ctatccactc ctcacatcca cacactgcac    1980
ccccactcct ggggcagggc caccagcatc caggcggcca gcaggcacct gagtggctgg    2040
gacaagggat cccccttccc tgtggttcta ttatattata attataatta aatatgagag    2100
catgct                                                              2106

<210> SEQ ID NO 30
<211> LENGTH: 1344
<212> TYPE: DNA
<213> ORGANISM: Artificial Sequence
<220> FEATURE:
<223> OTHER INFORMATION: Synthetic: Heavy Chain Nucleotide Sequence;
      Anti-LAG-3 mAb (BMS-986016)

<400> SEQUENCE: 30
caggtgcagc tacagcagtg gggcgcagga ctgttgaagc cttcggagac cctgtccctc      60
acctgcgctg tctatggtgg gtccttcagt gattactact ggaactggat ccgccagccc     120
ccagggaagg gctggagtg gattggggaa atcaatcatc gtggaagcac caactccaac     180
ccgtccctca agagtcgagt caccctatca ctagacacgt ccaagaacca gttctccctg    240
aagctgaggt ctgtgaccgc cgcggacacg gctgtgtatt actgtgcgtt tggatatagt    300
gactacgagt acaactggtt cgacccctgg ggccagggaa ccctggtcac cgtctcctca    360
gctagcacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accatgccca gcacctgagt tcctgggggg accatcagtc    720
ttcctgttcc cccaaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa atga                                           1344

<210> SEQ ID NO 31
<211> LENGTH: 645
<212> TYPE: DNA
<213> ORGANISM: Artificial Sequence
<220> FEATURE:
```

<223> OTHER INFORMATION: Synthetic: Light Chain Nucleotide Sequence;
      Anti-LAG-3 mAb (BMS-986016)

<400> SEQUENCE: 31

```
gaaattgtgt tgacacagtc tccagccacc ctgtctttgt ctccagggga aagagccacc      60
ctctcctgca gggccagtca gagtattagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac ttttggccag     300
gggaccaacc tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacctgacg      540
ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 32
<211> LENGTH: 6
<212> TYPE: PRT
<213> ORGANISM: Artificial Sequence
<220> FEATURE:
<223> OTHER INFORMATION: Synthetic: Motif

<400> SEQUENCE: 32

Met Tyr Pro Pro Pro Tyr
1               5